United States Patent
Adams et al.

(10) Patent No.: US 10,316,020 B2
(45) Date of Patent: Jun. 11, 2019

(54) INDANE DERIVATIVES AND THE USE THEREOF AS SOLUBLE GUANYLATE CYCLASE ACTIVATORS

(71) Applicant: NOVARTIS AG, Basel (CH)

(72) Inventors: Christopher Adams, Arlington, MA (US); Takeru Ehara, Arlington, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/063,059

(22) PCT Filed: Dec. 16, 2016

(86) PCT No.: PCT/IB2016/057737
§ 371 (c)(1),
(2) Date: Jun. 15, 2018

(87) PCT Pub. No.: WO2017/103888
PCT Pub. Date: Jun. 22, 2017

(65) Prior Publication Data
US 2019/0002438 A1    Jan. 3, 2019

Related U.S. Application Data

(60) Provisional application No. 62/269,408, filed on Dec. 18, 2015, provisional application No. 62/269,435, filed on Dec. 18, 2015.

(51) Int. Cl.
| | |
|---|---|
| *C07D 401/14* | (2006.01) |
| *C07D 401/10* | (2006.01) |
| *A61K 31/454* | (2006.01) |
| *C07D 401/12* | (2006.01) |
| *A61P 27/06* | (2006.01) |

(52) U.S. Cl.
CPC ............ *C07D 401/14* (2013.01); *A61P 27/06* (2018.01); *C07D 401/10* (2013.01); *C07D 401/12* (2013.01)

(58) Field of Classification Search
CPC .. C07D 401/14; C07D 401/10; C07D 401/12; A61P 27/06; A61K 31/454
USPC .................. 514/333, 318; 546/194
See application file for complete search history.

(56) References Cited

U.S. PATENT DOCUMENTS

| | | |
|---|---|---|
| 2011/0028493 A1 | 2/2011 | Matsunga et al. |
| 2013/0158028 A1 | 6/2013 | Stasch et al. |
| 2017/0197940 A1* | 7/2017 | Adams ................. C07D 401/14 |

FOREIGN PATENT DOCUMENTS

| | | |
|---|---|---|
| EP | 2 594 270 A2 | 5/2013 |
| WO | 2009/032249 A1 | 3/2009 |
| WO | 2009/071504 A1 | 6/2009 |
| WO | 2011/095534 A1 | 8/2011 |
| WO | 2011/095553 A1 | 8/2011 |
| WO | 2011/147810 A1 | 12/2011 |
| WO | 2014/039434 A1 | 3/2014 |
| WO | 2014/157740 A1 | 10/2014 |
| WO | 2015/011086 A1 | 1/2015 |
| WO | 2015/033307 A1 | 3/2015 |
| WO | 2015/095515 A1 | 6/2015 |
| WO | 2016/001875 A1 | 1/2016 |
| WO | 2016/001876 A1 | 1/2016 |
| WO | 2016/001878 A1 | 1/2016 |

* cited by examiner

*Primary Examiner* — Niloofar Rahmani
(74) *Attorney, Agent, or Firm* — Asha K. Nadipuram

(57) ABSTRACT

The present invention provides a compound of formula (I) or a pharmaceutically acceptable salt thereof; a method for manufacturing the compounds of the invention, and its therapeutic uses. The present invention further provides a combination of pharmacologically active agents and a pharmaceutical composition.

(I)

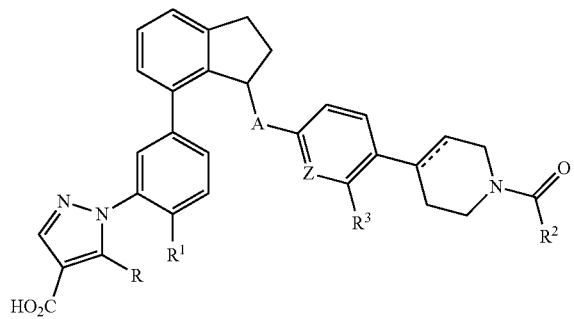

18 Claims, No Drawings

INDANE DERIVATIVES AND THE USE THEREOF AS SOLUBLE GUANYLATE CYCLASE ACTIVATORS

This application is a National Stage Entry of International application No. PCT/IB2016/057737, filed Dec. 16, 2016, which claims the benefit of U.S. Provisional Application No. 62/269,408, filed Dec. 18, 2015, and U.S. Provisional Application No. 62/269,435, filed Dec. 18, 2015, the disclosures of which are incorporated by reference herein.

FIELD OF THE INVENTION

The present invention is related generally to compounds which activate soluble guanylate cyclase (sGC). The invention further relates to the use of said sGC activators in the treatment of glaucoma and in the lowering intraocular pressure (IOP) such as that associated with glaucoma and ocular hypertension.

BACKGROUND OF THE INVENTION

The eye disease glaucoma is characterized by a permanent loss of visual function due to irreversible damage to the optic nerve. The several morphologically or functionally distinct types of glaucoma are typically characterized by an undesirable elevation of IOP, which is considered to be causally related to the pathological course of the disease. Continuously elevated IOP has been associated with the progressive loss of retinal ganglion cells and optic nerve damage ultimately resulting in the loss of visual function. In some cases, ocular hypertension, a condition in which IOP is elevated, can present without apparent loss of visual function. However, patients with ocular hypertension are considered to be at a high risk for eventually developing the visual loss associated with glaucoma. Therefore, lowering IOP is the current treatment objective for the of glaucoma patients and for patients with ocular hypertension in order to decrease the potential for, or severity of, glaucomatous retinopathy. Unfortunately, many individuals do not achieve or maintain desired level of IOP reduction when treated with existing glaucoma therapies.

Patients known as normotensive or low-tension glaucoma patients have relatively low IOP, yet present with glaucomatous visual field loss. These patients may benefit from agents that lower and control IOP, because glaucoma that is detected early and treated promptly may have reduced or delayed loss of visual function. Conventional therapeutic agents that have proven to be effective for the reduction of IOP include both agents that decrease aqueous humor production and agents that increase the outflow facility. Such agents are in general administered by one of two routes; topically by direct application to the eye, or orally. However, many of these agents have associated side effects which may render them undesirable as ocular therapeutic agents.

Soluble guanylate cyclase (sGC) is a receptor enzyme for the second messenger, nitric oxide (NO) in several cell types including muscle, epithelial, neuronal, and endothelial cells. In humans, functional sGC is a heterodimer composed of either an alpha 1 or alpha 2 subunit combined with the beta 1 subunit which has a heme prosthetic group. Under physiological conditions, NO binds to the prosthetic heme of sGC which activates the enzyme to catalyze the conversion of guanosine-5'-triphosphate (GTP) to cyclic guanosine monophosphate (cGMP). cGMP is a second messenger which in turn exerts its effects by activating cGMP dependent protein kinase (PKG) isoforms, phosphodiesterases, and cGMP gated ion channels. In doing so, sGC can thus modulate numerous pathways associated with diseases including hypertension (arterial and pulmonary), heart failure, atherosclerosis, erectile dysfunction, liver cirrhosis, and renal fibrosis. Under aforementioned pathologic conditions, prolonged oxidative stress can cause the oxidation of the heme group of sGC (from ferrous to ferric state) which is incapable of being activated by NO and can contribute to exacerbation of disease processes. As a consequence of sGC oxidation and unresponsiveness to NO, endothelial dysfunction, atherosclerosis, hypertension, stable or unstable angina pectoris, thromboses, myocardial infarction, strokes or erectile dysfunction are worsened. Therefore, pharmacological stimulation or activation of sGC offers a possibility to normalize cGMP production and therefore makes possible the treatment and/or prevention of such disorders.

To this effort, there are two classes of compounds have been identified, including NO-independent/reduced heme-dependent sGC stimulators and NO-independent/heme-independent sGC activators. sGC stimulators are dependent on heme, but they are not active once sGC become oxidized. sGC activators on the other hand can still activate the enzyme to generate cGMP even in the absence of nitric oxide (NO) and/or under oxidative stress induced oxidation of sGC in disease tissue. Thus, the activity of sGC in these situations will be corrected by sGC activators, but not by sGC stimulators, and will have the potential to provide benefit in many diseases caused by defective signaling in the NO pathway especially following oxidative stress.

SUMMARY OF THE INVENTION

The present invention in part relates to new activators of sGC and the use thereof in the treatment of disease. In one aspect the sGC activators provided herein are suitable for use in methods of treating glaucoma in human patients or other mammals. The present invention also relates to methods of lowering or controlling normal or elevated IOP in a human patient or other mammals. In particular, the invention provides methods of treating and/or preventing glaucoma by administration of a sGC activator compound described infra.

In the eye, the trabecular outflow pathway by which 70-80% of aqueous humor would normally leave the anterior chamber of the eye and lower intraocular pressure (IOP), is pathologically compromised in primary open angle glaucoma (POAG). Oxidative stress is thought to be an underlying factor that can adversely affect trabecular meshwork function, resulting from/in IOP elevation in POAG. Reactive oxygen species (ROS) not only decrease the bioavailability of nitric oxide (NO) but also shift the sGC redox equilibrium to its oxidized form, which as mentioned before is unresponsive to NO. Selective activation of the oxidized form of sGC should target only the diseased state of the target enzyme in the putative target tissue, trabecular meshwork/Schlemm's canal tissue, thus offering a highly innovative therapy for glaucoma that should work adjunctively with current therapies.

In one aspect of the invention, sGC activators, and salts thereof, are provided which have the structure of formula (I):

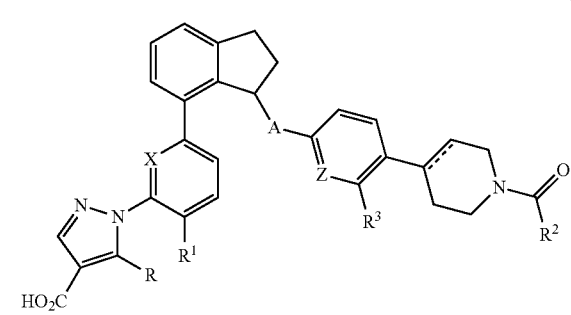

(I)

or a pharmaceutically acceptable salt thereof, wherein the variables are defined infra.

Certain embodiments of the present invention comprise compositions or methods which include or use compounds capable of activating sGC thereby modulating intraocular pressure in the eye. By activating sGC receptor activity, subject compounds according to certain embodiments of the present invention are accordingly useful for lowering and/or controlling IOP associated with normal-tension glaucoma, ocular hypertension, and glaucoma, including primary open-angle glaucoma in humans and other warm-blooded animals. When used in such applications, the compounds may be formulated in pharmaceutical compositions suitable for topical delivery to the eye.

The foregoing brief summary broadly describes the features and technical advantages of certain embodiments of the present invention. Additional features and technical advantages will be described in the detailed description of the invention that follows.

DESCRIPTION OF THE INVENTION

As the term is used herein, a "sGC activator" is a compound capable of modulating sGC activity to generate cGMP signaling which would otherwise be unresponsive to nitric oxide. In contrast, "sGC stimulators" refers to compounds that are capable of synergizing with nitric oxide and can directly stimulate cGMP production so long as the reduced heme domain is present in the enzyme.

In a first embodiment, the invention provides a compound according to Formula (I):

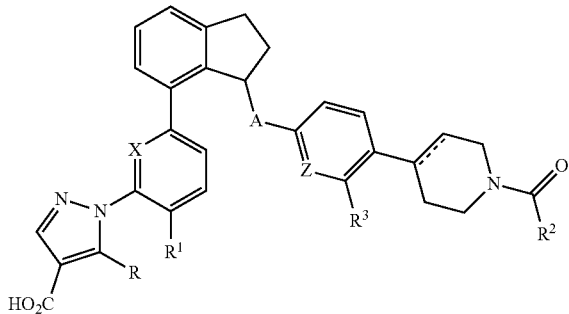

(I)

or a pharmaceutically acceptable salt thereof, wherein
X is CH or N;
\ is a single bond or a double bond;
A is $CH_2$, O or N(H);
Z is $CR^4$ or N with the proviso that A is not O when Z is N;
When X is CH then R is $C_1$-$C_4$alkoxy, amino, $C_1$-$C_4$alkylamino or di-$C_1$-$C_4$alkylamino; or
When X is N then R is $C_1$-$C_4$alkoxy or amino with the proviso that R is not $C_1$-$C_4$alkoxy, when A is NH and Z is CH;
$R^1$ is hydrogen, $C_1$-$C_4$alkyl or $C_1$-$C_4$alkoxy;
$R^2$ is $C_3$-$C_5$cycloalkyl, $C_1$-$C_4$alkyl or hydroxy$C_1$-$C_4$alkyl;
$R^3$ is hydrogen, halogen or $C_1$-$C_4$alkyl; and
$R^4$ is hydrogen, methyl or ethyl.

In a second embodiment, the invention provides a compound according to Formula (Ia)

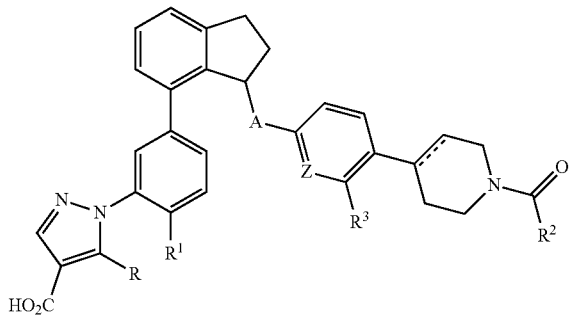

(Ia)

or a pharmaceutically acceptable salt thereof, wherein
the \ bond is a single bond or a double bond;
A is $CH_2$, O or N(H);
Z is $CR^4$ or N with the proviso that A is not O when Z is N;
R is $C_1$-$C_4$alkoxy, amino, $C_1$-$C_4$alkylamino or di-$C_1$-$C_4$alkylamino;
$R^1$ is hydrogen, $C_1$-$C_4$alkyl or $C_1$-$C_4$alkoxy;
$R^2$ is $C_3$-$C_5$cycloalkyl, $C_1$-$C_4$alkyl or hydroxy$C_1$-$C_4$alkyl;
$R^3$ is hydrogen, halogen or $C_1$-$C_4$alkyl; and
$R^4$ is hydrogen, methyl or ethyl.

In certain preferred compounds of the first or second embodiment, compounds of formula I are provided which are either racemic or enantiomerically enriched. In certain preferred aspects, compounds of formula I are enriched at the indanyl chiral center connected to variable A.

In a third embodiment, compounds of the first or second embodiment are provided in which R is methoxy, ethoxy, amino or methyl amino. In certain preferred aspects of the third embodiment, R is methoxy or amino.

In a fourth embodiment, compounds of any one of embodiments one to three are provided in which $R^1$ is hydrogen, methyl or methoxy. In certain preferred compounds of the fourth embodiment, $R^1$ is hydrogen. In other preferred compounds of the fourth embodiment, $R^1$ is methyl.

In a fifth embodiment, compounds of any one of embodiments one to four are provided in which Z is CH.

In a sixth embodiment, compounds of any one of embodiments two to four are provided in which Z is N; and A is $CH_2$ or N(H).

In a seventh embodiment, compounds of any one of embodiments one to five are provided in which A is O.

In a eighth embodiment, compounds of any one of embodiments one to six are provided in which A is N(H) or $CH_2$. In certain aspects of the eighth embodiment, A is N(H). In other aspects, A is $CH_2$. In certain preferred compounds of the eighth embodiment A is N(H) or $CH_2$ when Z is N. In other preferred compounds of the seventh embodiment, A is N(H) or $CH_2$ when Z is CH.

In a ninth embodiment, compounds of any one of embodiments one to eight are provided in which $R^2$ is cyclopropyl or 1-hydroxyethyl. In certain aspects of the ninth embodiment when $R^2$ is hydroxyethyl, the hydroxyethyl chiral center may be racemic or enantiomerically enriched in either the (R) or (S) isomer. In certain preferred aspects of the ninth embodiment, $R^2$ is cyclopropyl or (S)-1-hydroxyethyl.

In a tenth embodiment, compounds of any one of embodiments one to nine are provided in which $R^3$ is ethyl.

In an eleventh embodiment, compounds of any one of embodiments one to ten are provided in which the \ bond is a single bond.

In a twelfth embodiment, compounds of any one of embodiments one to ten are provided in which the \ bond is a double bond.

In a thirteenth embodiment, compounds are provided which are compounds of Formula (II):

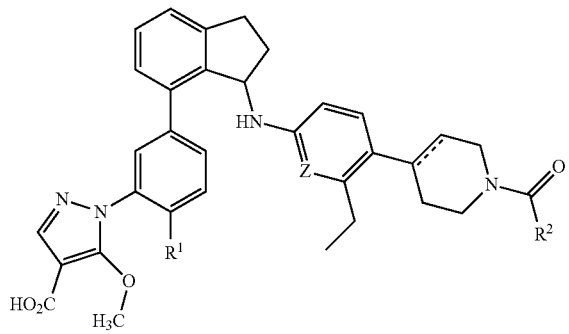

(II)

Or a pharmaceutically acceptable salt thereof wherein
Z is N or CH;
R¹ is hydrogen, methyl or methoxy; and
R² is cyclopropyl or 1-hydroxyethyl.

Preferred compounds of Formula (II) have the stereochemistry of the formula:

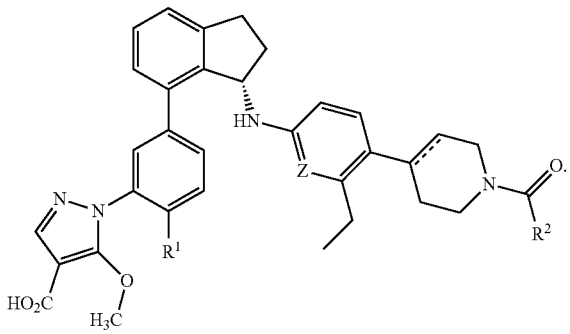

In a fourteenth embodiment, compounds of the thirteenth embodiment are provided which are compounds of Formula (IIa) or (IIb):

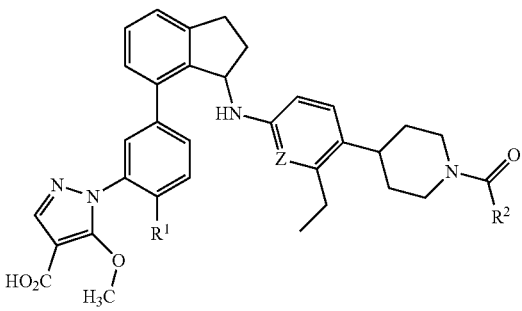

(IIa)

and

-continued

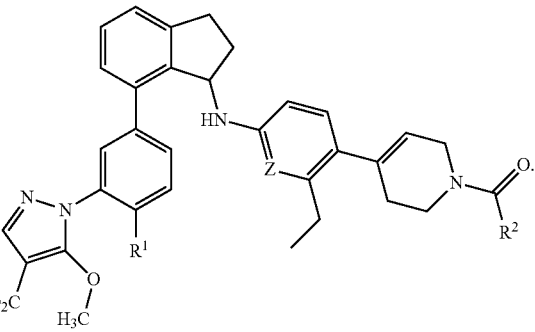

(IIb)

In certain aspects of the fourteenth embodiment, the compound is represented by Formula (IIa). In other aspects of the fourteenth embodiment, the compound is represented by Formula (IIb).

In a fifteenth embodiment, compounds are provided which are compounds of Formula (III):

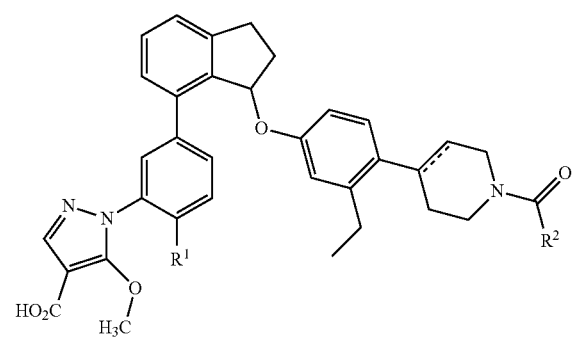

(III)

Or a pharmaceutically acceptable salt thereof wherein
R¹ is hydrogen, methyl or methoxy; and
R² is cyclopropyl or 1-hydroxyethyl.

Preferred compounds of Formula (III) have the stereochemistry of the formula:

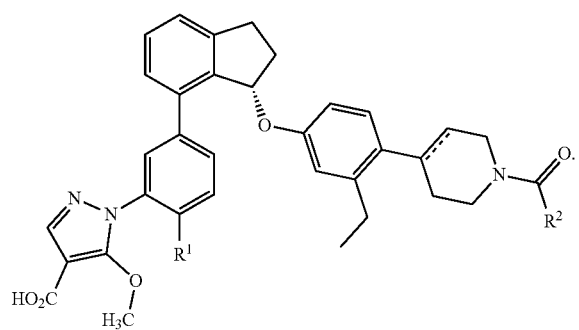

In a sixteenth embodiment, compounds of the fifteenth embodiment provided which are compounds of Formula (IIIa) or (IIIb):

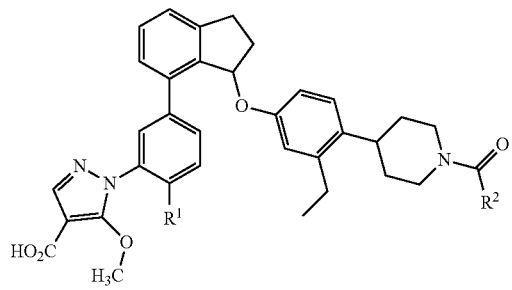

(IIIa)

or (IIIb)

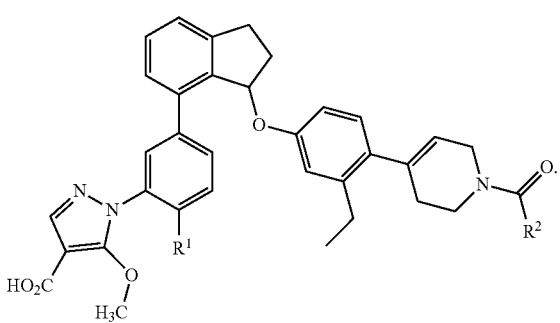

In certain aspects of the sixteenth embodiment, the compound is represented by Formula (IIIa). In other aspects of the sixteenth embodiment, the compound is represented by Formula (IIIb).

In a seventeenth embodiment, compounds are provided which are compounds of Formula (IV):

(IV)

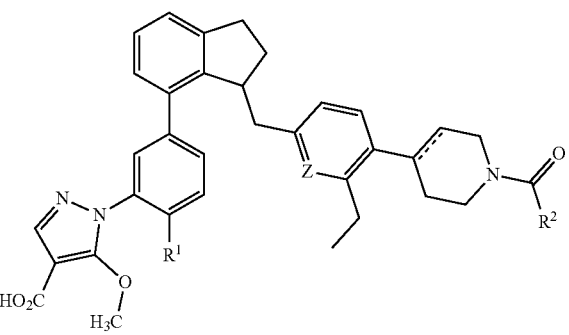

Or a pharmaceutically acceptable salt thereof wherein
Z is N or CH;
R¹ is hydrogen, methyl or methoxy; and
R² is cyclopropyl or 1-hydroxyethyl.
Preferred compounds of Formula (IV) have the stereochemistry of the formula:

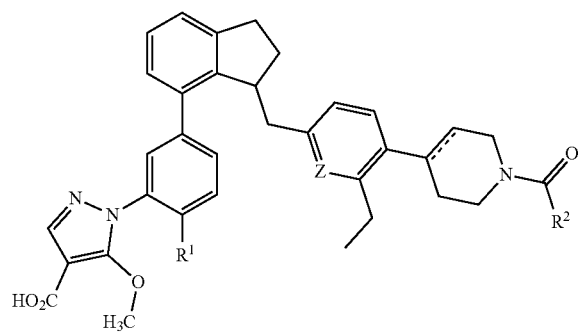

In an eighteenth embodiment, compounds are provided which are compounds of Formula (IVa) or (IVb):

(IVa)

or (IVb)

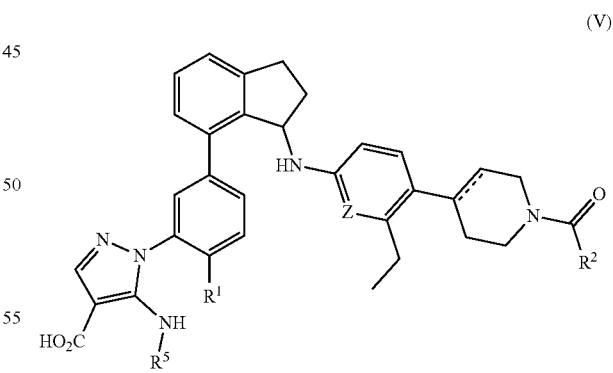

In certain aspects of the eighteenth embodiment, the compound is represented by Formula (IVa). In other aspects of the eighteenth embodiment, the compound is represented by Formula (IVb).

In a nineteenth embodiment, compounds of any one of embodiments one to twelve are provided which are compounds of Formula (V):

(V)

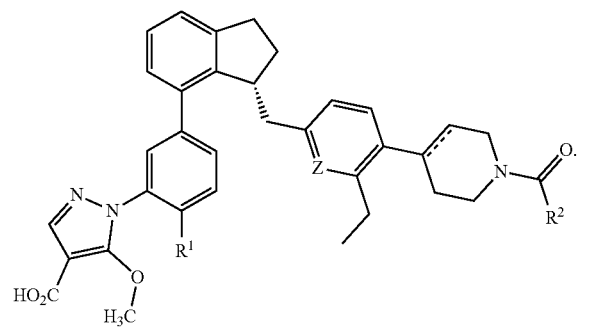

Or a pharmaceutically acceptable salt thereof wherein
Z is N or CH;
R¹ is hydrogen, methyl or methoxy;
R² is cyclopropyl or 1-hydroxyethyl; and
R⁵ is hydrogen or methyl.
Preferred compounds of Formula (V) have the stereochemistry of the formula:

(V)

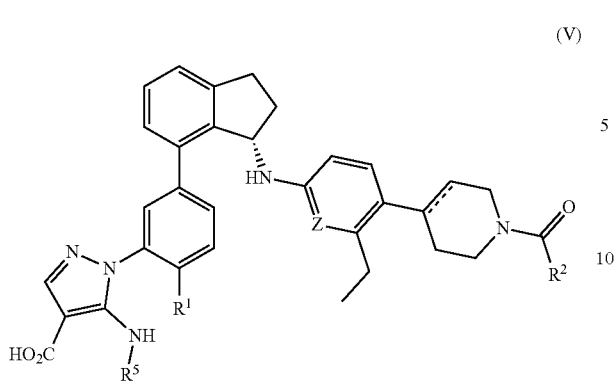

In a twentieth embodiment, compounds of the nineteenth embodiment provided which are compounds of Formula (Va) or (Vb):

(Va)

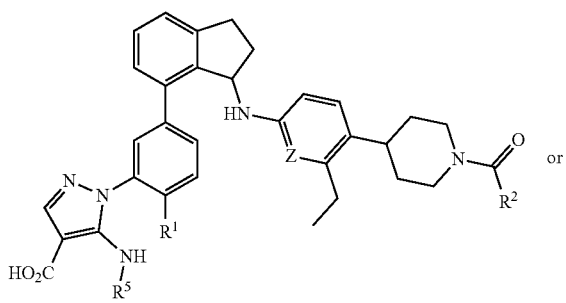

or (Vb)

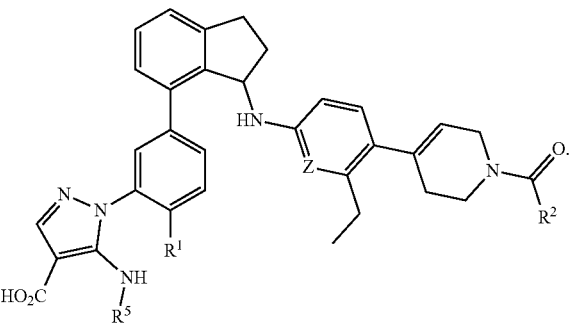

In certain aspects of the twentieth embodiment, the compound is represented by Formula (Va). In other aspects of the twentieth embodiment, the compound is represented by Formula (Vb).

In a twenty first embodiment, compounds of any one of embodiments one to twelve are provided which are compounds of Formula (VI):

(VI)

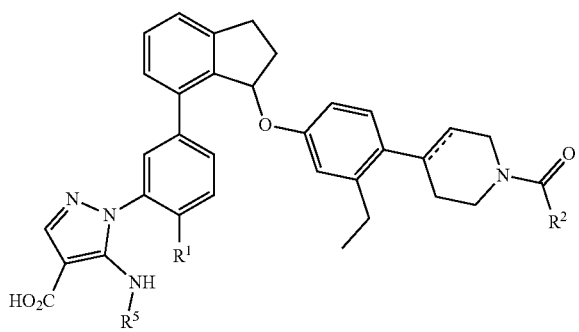

Or a pharmaceutically acceptable salt thereof wherein $R^1$ is hydrogen, methyl or methoxy;

$R^2$ is cyclopropyl or 1-hydroxyethyl; and $R^5$ is hydrogen or methyl.

Preferred compounds of Formula (VI) have the stereochemistry of the formula:

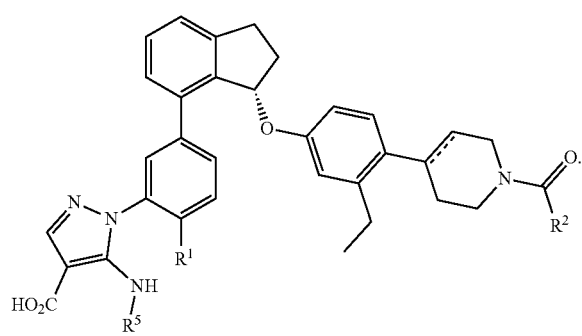

In a twenty second embodiment, compounds of the twenty first embodiment provided which are compounds of Formula (VIa) or (VIb):

(VIa)

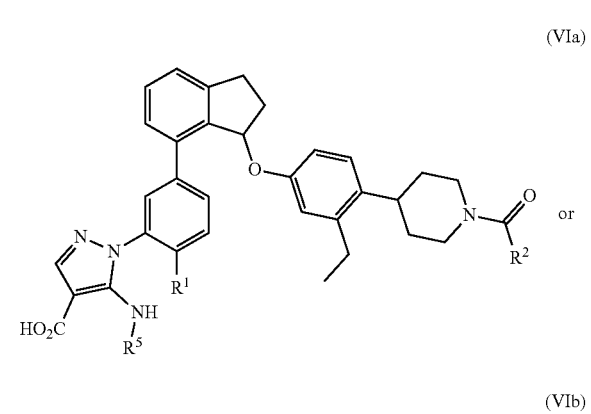

or (VIb)

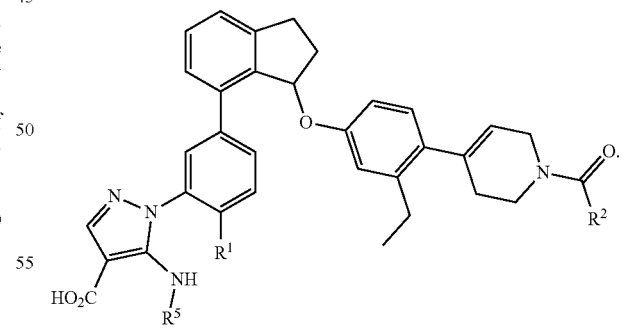

In certain aspects of the twenty second embodiment, the compound is represented by Formula (VIa). In other aspects of the twenty second embodiment, the compound is represented by Formula (VIb).

In a twenty third embodiment, compounds of any one of embodiments one to twelve are provided which are compounds of Formula (VII):

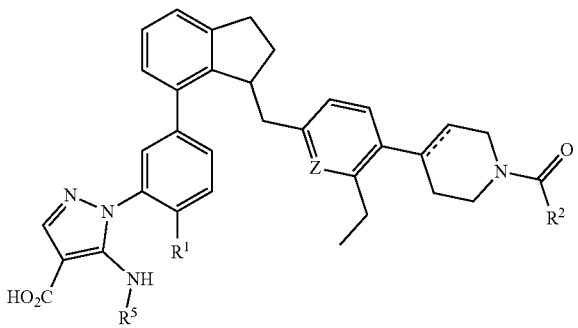

(VII)

Or a pharmaceutically acceptable salt thereof wherein
Z is N or CH;
R[1] is hydrogen, methyl or methoxy;
R[2] is cyclopropyl or 1-hydroxyethyl; and
R[5] is hydrogen or methyl.

Preferred compounds of Formula (VII) have the stereochemistry of the formula:

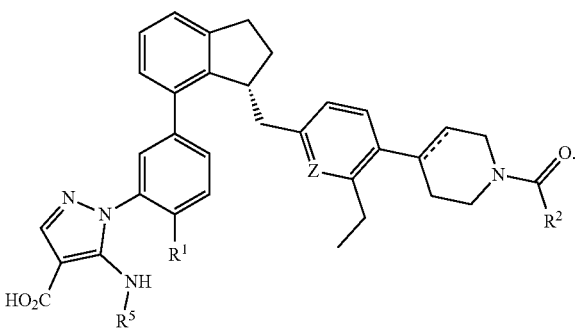

In a twenty fourth embodiment, compounds of the twenty third embodiment provided which are compounds of Formula (VIIa) or (VIIb):

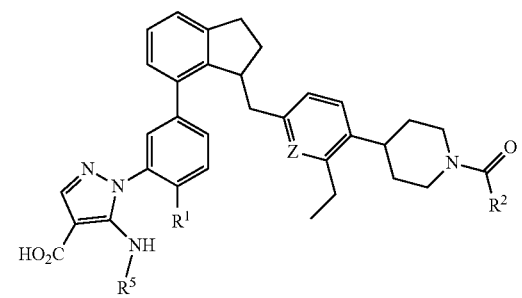

(VIIa)

or (VIIb)

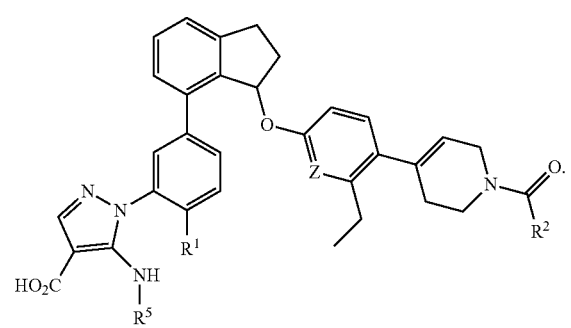

In certain aspects of the twenty fourth embodiment, the compound is represented by Formula (VIIa). In other aspects of the twenty fourth embodiment, the compound is represented by Formula (VIIb).

In certain aspects of any one of embodiments 13, 14, 17, 19, 20, 22 or 24, Z is CH.

In a twenty fifth embodiment, the invention provides compounds of the second embodiment, or a pharmaceutically acceptable salt thereof, wherein the compound is selected from the group consisting of:

(+)-(R)-1-(3-(3-(4-(1-(cyclopropanecarbonyl)piperidin-4-yl)-3-ethylbenzyl)-2,3-dihydro-1H-inden-4-yl)phenyl)-5-methoxy-1H-pyrazole-4-carboxylic acid;

(+)-1-(3-((R)-3-(3-ethyl-4-(1-((S)-2-hydroxypropanoyl)piperidin-4-yl)benzyl)-2,3-dihydro-1H-inden-4-yl)phenyl)-5-methoxy-1H-pyrazole-4-carboxylic acid;

(+)-(S)-1-(3-(3-((4-(1-(cyclopropanecarbonyl)piperidin-4-yl)-3-ethylphenyl)amino)-2,3-dihydro-1H-inden-4-yl)phenyl)-5-methoxy-1H-pyrazole-4-carboxylic acid;

(+)-1-(3-(3-((3-ethyl-4-(1-((S)-2-hydroxpropanoyl)piperidin-4-yl)phenyl)amino)-2,3-dihydro-1H-inden-4-yl)phenyl)-5-methoxy-1H-pyrazole-4-carboxylic acid;

(+)-(S)-1-(3-(3-(4-(1-(cyclopropanecarbonyl)piperidin-4-yl)-3-ethylphenoxy)-2,3-dihydro-1H-inden-4-yl)phenyl)-5-methoxy-1H-pyrazole-4-carboxylic acid;

1-(3-((S)-3-(3-ethyl-4-(1-((S)-2-hydroxypropanoyl)piperidin-4-yl)phenoxy)-2,3-dihydro-1H-inden-4-yl)phenyl)-5-methoxy-1H-pyrazole-4-carboxylic acid;

(+)-1-(5-(3-((4-(1-(cyclopropanecarbonyl)piperidin-4-yl)-3-ethylphenyl)amino)-2,3-dihydro-1H-inden-4-yl)-2-methylphenyl)-5-methoxy-1H-pyrazole-4-carboxylic acid;

(+)-1-(5-(3-((4-(1-(cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylic acid;

(+)-5-amino-1-(3-(3-((4-(1-(cyclopropanecarbonyl)piperidin-4-yl)-3-ethylphenyl)amino)-2,3-dihydro-1H-inden-4-yl)phenyl)-1H-pyrazole-4-carboxylic acid;

(+)-1-(3-(3-((1'-(cyclopropanecarbonyl)-2-ethyl-1',2',3',6-tetrahydro-[3,4'-bipyridin]-6-yl)amino)-2,3-dihydro-1H-inden-4-yl)phenyl)-5-methoxy-1H-pyrazole-4-carboxylic acid; and (enantiomer-2)-1-(3-(3-((4-(1-(Cyclopropanecarbonyl)piperidin-4-yl)-3-ethylphenyl)amino)-2,3-dihydro-1H-inden-4-yl)phenyl)-5-(methylamino)-1H-pyrazole-4-carboxylic acid.

(+)-(R)-5-Amino-1-(3-(3-(4-(1-(cyclopropanecarbonyl)piperidin-4-yl)-3-ethylbenzyl)-2,3-dihydro-1H-inden-4-yl)phenyl)-1H-pyrazole-4-carboxylic acid (R)-1-(3-(3-(4-(1-(cyclopropanecarbonyl)piperidin-4-yl)-3-ethylbenzyl)-2,3-dihydro-1H-inden-4-yl)phenyl)-5-(methylamino)-1H-pyrazole-4-carboxylic acid In a twenty sixth embodiment, the invention provides a compound according to Formula (VIII).

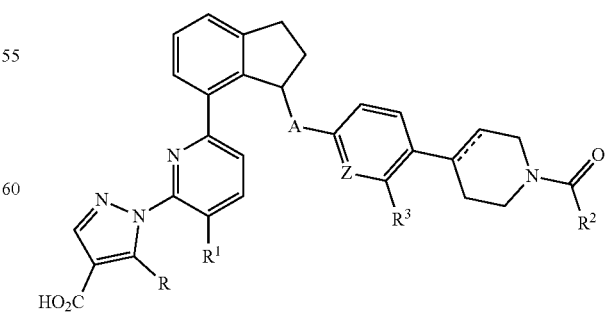

(VIII)

or a pharmaceutically acceptable salt thereof, wherein
⦀ is a single or double bond;

A is CH$_2$, O or N(H)

Z is CR$^4$ or N with the proviso that A is not O when Z is N;

R is C$_1$-C$_4$alkoxy or amino with the proviso that R is not C$_1$-C$_4$alkoxy, when A is NH and Z is CH;

R$^1$ is hydrogen, C$_1$-C$_4$alkyl or C$_1$-C$_4$alkoxy;

R$^2$ is C$_3$-C$_5$cycloalkyl, C$_1$-C$_4$alkyl or hydroxyC$_1$-C$_4$alkyl; and R$^3$ is hydrogen, halogen or C$_1$-C$_4$alkyl.

In certain preferred compounds of the twenty sixth embodiment, compounds of formula VIII are provided which are either racemic or enantiomerically enriched. In certain preferred aspects, compounds of formula VIII are enriched at the indanyl chiral center connected to variable A.

In a twenth seventh embodiment, compounds of the twenty sixth embodiment are provided in which R is methoxy, ethoxy, or amino. In certain preferred aspects of the twenth seventh embodiment, R is methoxy or amino.

In a twenty eighth embodiment, compounds of the twenty sixth or twenty seventh embodiment are provided in which R$^1$ is hydrogen or methyl. In certain preferred compounds of the twenty eighth embodiment, R$^1$ is hydrogen. In other preferred compounds of the twenty eighth embodiment, R$^1$ is methyl.

In a twenty ninth embodiment, compounds of any one of embodiments twenty six to twenty eight are provided in which Z is CH.

In a thirtieth embodiment, compounds of any one of embodiments twenty six to twenty eight are provided in which Z is N.

In a thirty first embodiment, compounds of any one of embodiments twenty six to twenty eight are provided in which A is O.

In a thirty second embodiment, compounds of any one of embodiments twenty six to twenty eight are provided in which A is N(H) or CH$_2$. In certain aspects of the thirty second embodiment, A is N(H). In other aspects, A is CH$_2$. In certain preferred compounds of the thirty second embodiment A is N(H) or CH$_2$ when Z is N. In other preferred compounds of the thirty second embodiment, A is N(H) or CH$_2$ when Z is CH.

In a thirty third embodiment, compounds of any one of embodiments twenty six to thirty two are provided in which R$^2$ is cyclopropyl or 1-hydroxyethyl. In certain aspects of the thirty third embodiment when R$^2$ is hydroxyethyl, the hydroxyethyl chiral center may be racemic or enantiomerically enriched in either the (R) or (S) isomer. In certain preferred aspects of the thirty third embodiment, R$^2$ is cyclopropyl or (S)-1-hydroxyethyl.

In a thirty fourth embodiment, compounds of any one of embodiments twenty six to thirty three are provided in which R$^3$ is ethyl.

In a thirty fifth embodiment, compounds of any one of embodiments twenty six to thirty four are provided in which the \ bond is a single bond.

In a thirty sixth embodiment, compounds of any one of embodiments twenty six to thirty four are provided in which the \ bond is a double bond.

In a thirty seventh embodiment, compounds of the twenty sixth embodiment are provided which are compounds of Formula (IX):

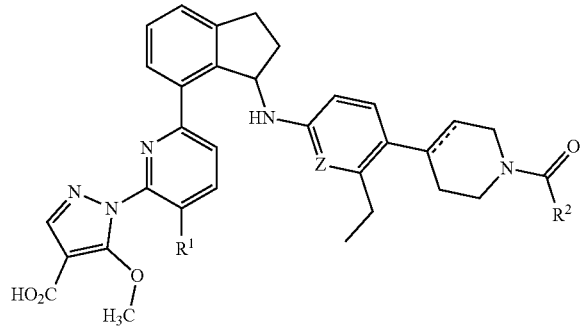

(IX)

Or a pharmaceutically acceptable salt thereof wherein

Z is N or CH;

R$^1$ is hydrogen or methyl; and

R$^2$ is cyclopropyl or 1-hydroxyethyl.

Preferred compounds of Formula (IX) have the stereochemistry of the formula:

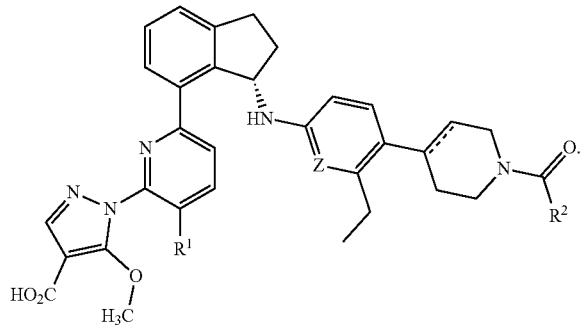

In a thirty eighty embodiment, compounds of embodiment twenty six are provided which are compounds of Formula (X):

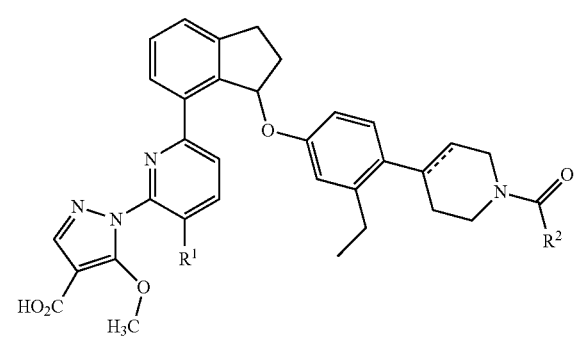

(X)

Or a pharmaceutically acceptable salt thereof wherein

R$^1$ is hydrogen or methyl; and

R$^2$ is cyclopropyl or 1-hydroxyethyl.

Preferred compounds of Formula (X) have the stereochemistry of the formula:

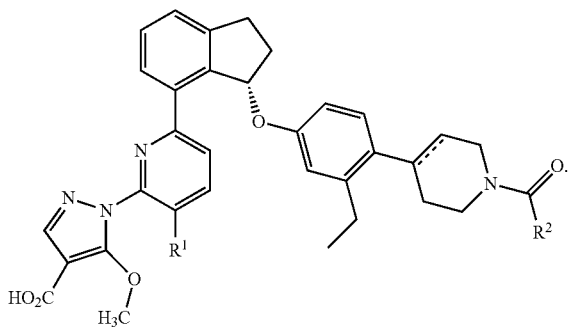

In a thirty ninth embodiment, compounds of embodiment thirty eighth are provided which are compounds of Formula (Xa) or (Xa):

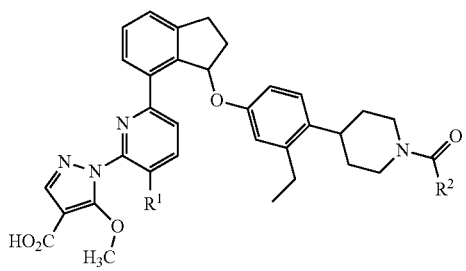

(Xa)

or

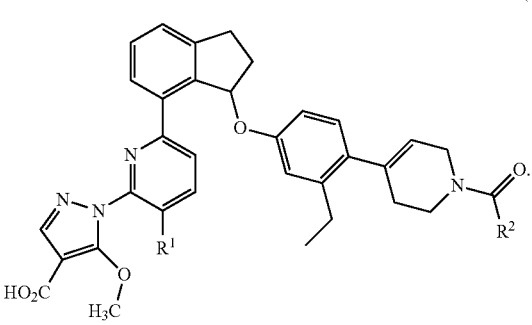

(Xb)

In certain aspects of the thirty ninth embodiment, the compound is represented by Formula (Xa). In other aspects of the fourteenth embodiment, the compound is represented by Formula (Xb).

In a fortieth embodiment, compounds of embodiment twenty six are provided which are compounds of Formula (XI):

(XI)

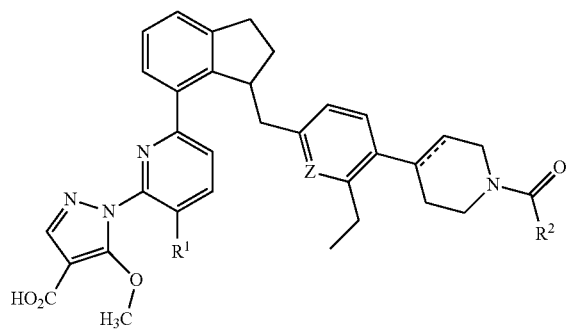

Or a pharmaceutically acceptable salt thereof wherein

Z is N or CH;

$R^1$ is hydrogen or methyl; and $R^2$ is cyclopropyl or 1-hydroxyethyl.

Preferred compounds of Formula (XI) have the stereochemistry of the formula:

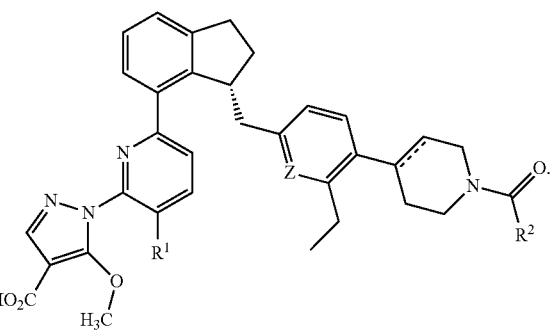

In a forty first embodiment, compounds of the fortieth embodiment provided which are compounds of Formula (XIa) or (XIb):

(XIa)

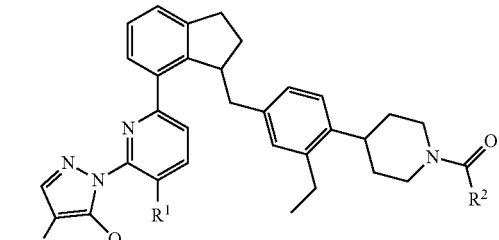

or (XIb)

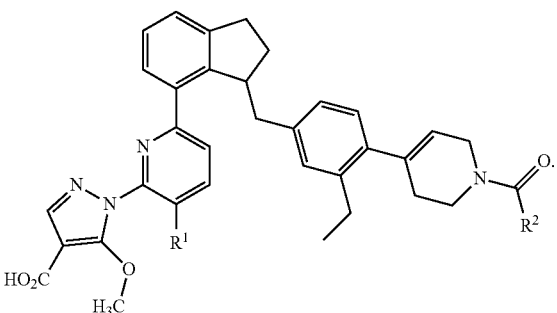

In certain aspects of the forty first embodiment, the compound is represented by Formula (XIa). In other aspects of the forty first embodiment, the compound is represented by Formula (XIb).

In a forty second embodiment, compounds of embodiment twenty six are provided are provided which are compounds of Formula (XII):

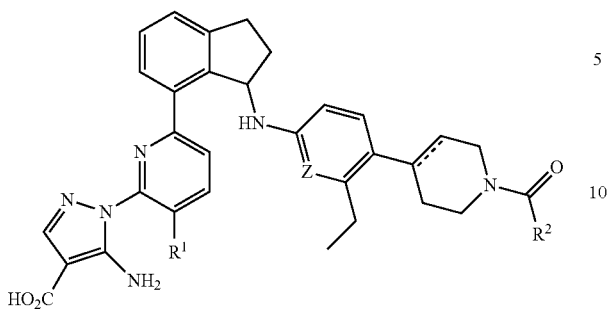

(XII)

Or a pharmaceutically acceptable salt thereof wherein
Z is N or CH;
R¹ is hydrogen or methyl; and
R² is cyclopropyl or 1-hydroxyethyl.

Preferred compounds of Formula (XII) have the stereochemistry of the formula:

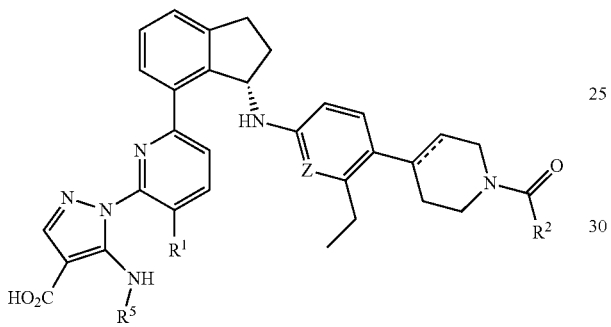

In a forty third embodiment, compounds of the forty second embodiment are provided which are compounds of Formula (XIIa) or (XIIb):

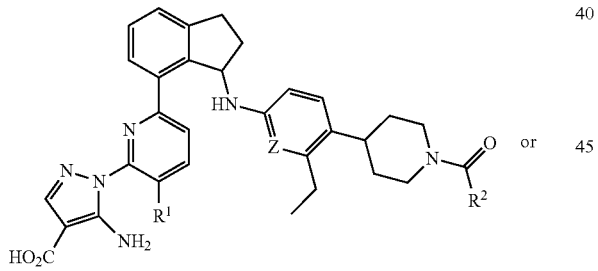

(XIIa)

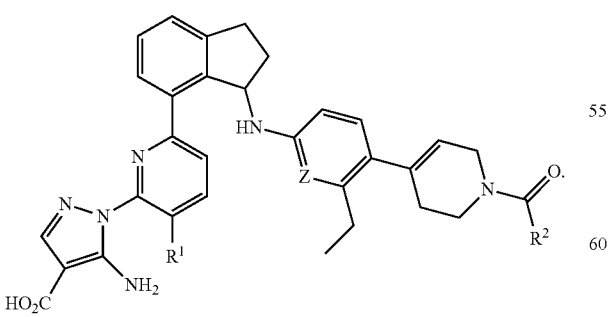

(XIIb)

In certain aspects of the forty third embodiment, the compound is represented by Formula (XIIa). In other aspects of the forty third embodiment, the compound is represented by Formula (XIIb).

In a forty fourth embodiment, compounds of embodiment twenty six are provided which are compounds of Formula (XIII):

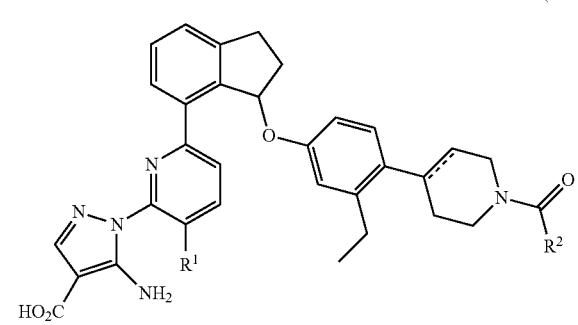

(XIII)

Or a pharmaceutically acceptable salt thereof wherein
R¹ is hydrogen or methyl; and
R² is cyclopropyl or 1-hydroxyethyl.

Preferred compounds of Formula (XIII) have the stereochemistry of the formula:

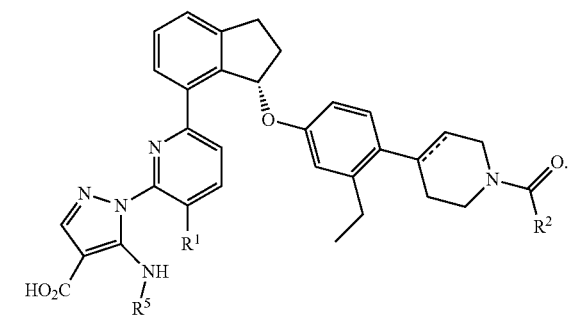

In a forty fifth embodiment, compounds of the forty fourth embodiment provided which are compounds of Formula (XIIIa) or (XIIIb):

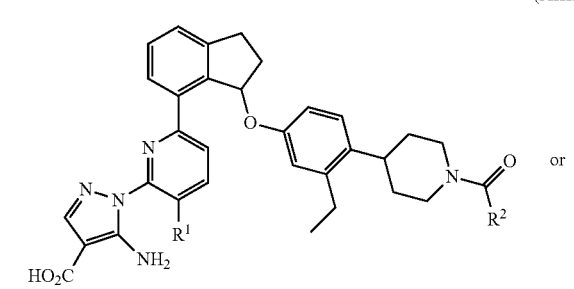

(XIIIa)

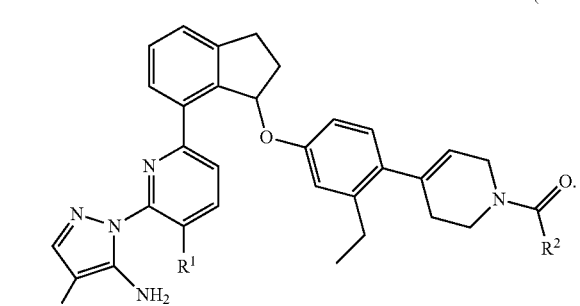

(XIIIb)

In certain aspects of the forty fifth embodiment, the compound is represented by Formula (XIIIa). In other aspects of the forty fifth embodiment, the compound is represented by Formula (XIIIb).

In a forty sixth embodiment, compounds of embodiment twenty six are provided which are compounds of Formula (XIV):

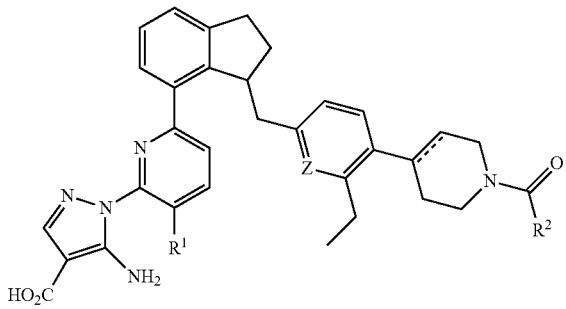

(XIV)

Or a pharmaceutically acceptable salt thereof wherein
Z is N or CH;
$R^1$ is hydrogen or methyl; and
$R^2$ is cyclopropyl or 1-hydroxyethyl.

Preferred compounds of Formula (XIV) have the stereochemistry of the formula:

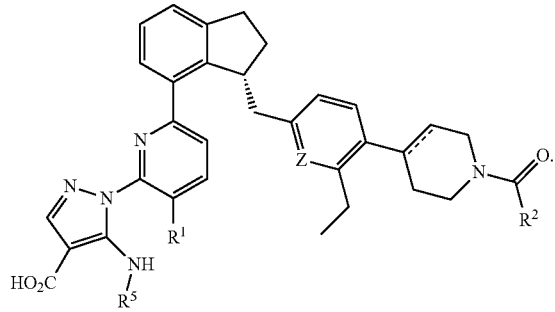

In a forty seventh embodiment, compounds of the forty sixth embodiment are provided which are compounds of Formula (XIVa) or (XIVb):

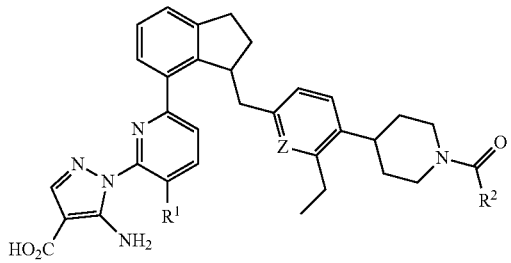

(XIVa)

or (XIVb)

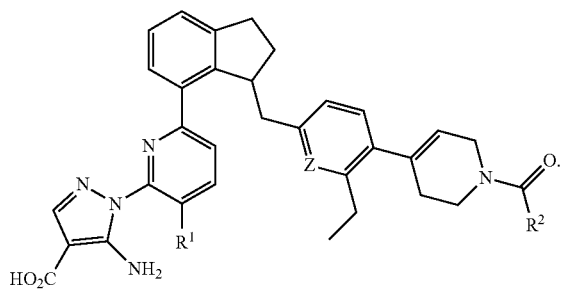

In certain aspects of the forthy seventh embodiment, the compound is represented by Formula (XIVa). In other aspects of the forty seventh embodiment, the compound is represented by Formula (XIVb).

In certain aspects of any one of embodiments 37, 40, 42, 43, 46, or 47, Z is CH.

In a forty eighth embodiment, the invention provides compounds of the twenty sixth embodiment, or a pharmaceutically acceptable salt thereof, wherein the compound is selected from the group consisting of:

(+)-1-(6-(3-(4-(1-(cyclopropanecarbonyl)piperidin-4-yl)-3-ethylbenzyl)-2,3-dihydro-1H-inden-4-yl)pyridin-2-yl)-5-methoxy-1H-pyrazole-4-carboxylic acid;

(S)-1-(6-(3-(4-(1-(cyclopropanecarbonyl)piperidin-4-yl)-3-ethylphenoxy)-2,3-dihydro-1H-inden-4-yl)pyridin-2-yl)-5-methoxy-1H-pyrazole-4-carboxylic acid;

1-(6-((S)-3-(3-ethyl-4-(1-((S)-2-hydroxpropanoyl)piperidin-4-yl)phenoxy)-2,3-dihydro-1H-inden-4-yl)pyridin-2-yl)-5-methoxy-1H-pyrazole-4-carboxylic acid;

(+)-5-amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylic acid;

(S)-5-amino-1-(6-(3-(4-(1-(cyclopropanecarbonyl)piperidin-4-yl)-3-ethylphenoxy)-2,3-dihydro-1H-inden-4-yl)pyridin-2-yl)-1H-pyrazole-4-carboxylic acid;

(+)-1-(6-(3-(((1'-(cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylic acid;

1-(6-((S or R)-3-((2-ethyl-1'-((S)-2-hydroxypropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylic acid (Example 17B);

(R)-5-Amino-1-(6-(3-(4-(1-(cyclopropanecarbonyl)piperidin-4-yl)-3-ethylbenzyl)-2,3-dihydro-1H-inden-4-yl)pyridin-2-yl)-1H-pyrazole-4-carboxylic acid; and (+)-1-(6-(3-(3-ethyl-4-(1-((S)-2-hydroxypropanoyl)piperidin-4-yl)benzyl)-2,3-dihydro-1H-inden-4-yl)pyridin-2-yl)-5-methoxy-1H-pyrazole-4-carboxylic acid.

Certain particularly preferred synthetic intermediates suitable for making compounds of the instant invention include those compounds of the formula:

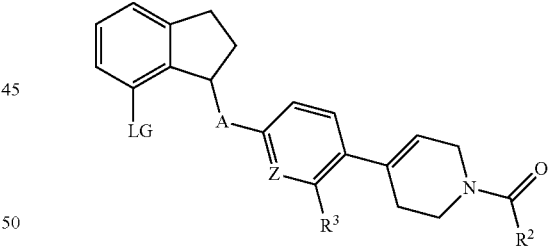

Where A, Z, $R^2$, and $R^3$ are substituents as defined in embodiment 1. LG is a moiety suitable for transition metal mediated cross coupling reactions. In preferred intermediates, LG is a sulfonic acid ester (such as triflate ($OSO_2CF_3$), mesylate ($OSO_2CH_3$), or tosylate ($OSO_2C_6H_4Me$)) or LG is a halide suitable for Pd-mediated cross coupling reactions (preferably Iodo, Bromo or Chloro). In certain intermediates suitable for preparation of compounds of Formula (I), LG is triflate, mesylate, tosylate, iodo, bromo or chloro.

Certain particularly preferred intermediates suitable for use in the preparation of some of the compounds of the invention include, tert-butyl 6-((7-bromo-2,3-dihydro-1H-inden-1-yl)amino)-2-ethyl-3',6'-dihydro-[3,4'-bipyridine]-1'(2'H)-carboxylate;

(6-((7-bromo-2,3-dihydro-1H-inden-1-yl)amino)-2-ethyl-3',6'-dihydro-[3,4'-bipyridin]-1'(2'H)-yl)(cyclopropyl)methanone; and (S)-(6-((7-bromo-2,3-dihydro-1H-inden-1-yl)amino)-2-ethyl-3',6'-dihydro-[3,4'-bipyridin]-1'(2'H)-yl)(cyclopropyl)methanone.

In a forty ninth embodiment, the present invention relates to a method of treating or preventing glaucoma or reducing intraocular pressure comprising administering to a subject in need thereof a sGC activator selected from the compounds of any one of embodiments one to forty eight. The invention has surprisingly shown that administration of sGC activators to a patient in need of therapy has desirable sustained efficacy in reducing IOP and in the treatment of glaucoma. The compounds of Formula (I) provide reduced systemic exposure when administered ocularly, e.g., as an eye drop. In particular compounds of formula I exhibit rapid systemic clearance compared to other sGC compounds disclosed in PCT/IB2015/055006 filed Jul. 2, 2015 which include a 1H-pyrazole-4-carboxylic acid fragment that is unsubstituted at the 5 position of the pyrazole ring or substituted with $C_1$-$C_4$alkyl, monofluoromethyl, difluoromethyl or trifluoromethyl. The compounds of the instant invention are systemically cleared faster than the compounds of the '006 application. This may be desirable for localized ocular therapy, e.g., for treatment of glaucoma by topical ocular administration.

Unless specified otherwise, the term "compounds of the present invention" refers to compounds of formula (I) and subformulae thereof, and salts thereof, as well as all stereoisomers (including diastereoisomers and enantiomers), rotamers, tautomers and isotopically labeled compounds (including deuterium substitutions), as well as inherently formed moieties.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula I in acetate, ascorbate, ad ipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{123}I$, $^{124}I$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, activation of soluble guanylate cyclase activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by activation of sGC, or (ii) associated with decreased sGC activity, or (iii) characterized by activity (normal or abnormal) of sGC. In another non-limiting embodiment, the term "a therapeutically effective amount" refers to the amount of the compound of the present invention that, when administered to a cell, or a tissue, or a non-cellular biological material, or a medium, is effective to at least partially increasing the activity of sGC.

As used herein, the term "subject" refers to an animal. Typically the animal is a mammal. A subject also refers to for example, primates (e.g., humans, male or female), cows, sheep, goats, horses, dogs, cats, rabbits, rats, mice and the like. In certain embodiments, the subject is a primate. In yet other embodiments, the subject is a human. In certain other embodiments, the compounds of the invention may be suitable for use in the treatment of glaucoma or reduction of IOP in dogs.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "activate", "activation" or "activating" refers to the significant increase in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent or supercritical fluid chromatography using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Typically, the compounds of formula (I) can be prepared according to the Schemes provided infra General Synthetic Aspects Typically, the compounds of Formula (I) can be prepared according to the Schemes provided below. The following Examples serve to illustrate the invention without limiting the scope thereof.

Compounds of type 1e; wherein $R^a$ is H, $C_1$-$C_4$ alkyl, or $C_1$-$C_4$ alkoxy; $R^b$ is $C_1$-$C_4$ alkyl; $R^z$ is methyl or ethyl; $X^a$ is a halide that is suitable for palladium mediated couplings can be synthesized according to Scheme 1.

Scheme 1

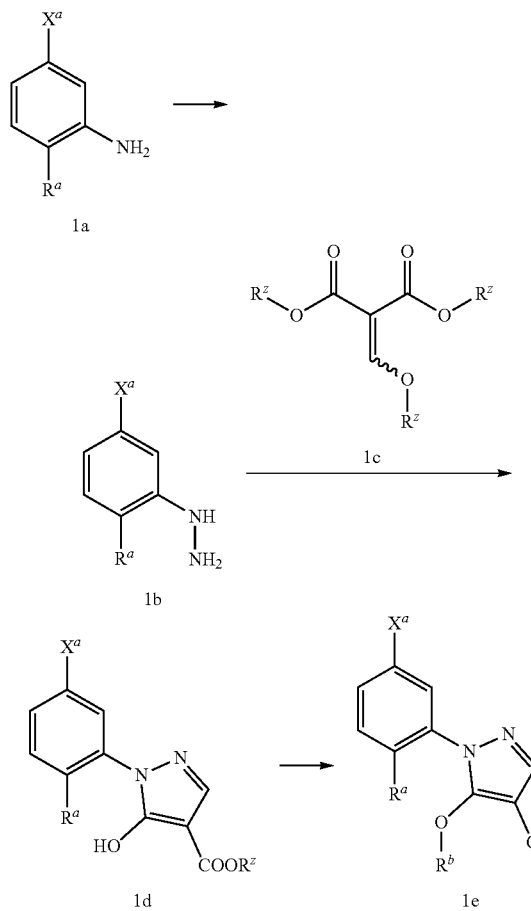

Aryl hydrazines 1b are either commercially available or can be prepared by treating anilines 1a with sodium nitrite under aqueous acidic conditions, such as 6N HCl in water, followed by reduction with reagents such as stannous chloride. Malonate derivatives 1c such as diethyl 2-(ethoxymethylene)malonate ($R^z$=Et, CAS #87-13-8) or dimethyl 2-(methoxymethylene)malonate ($R^z$=Me, CAS #22398-14-7) can be reacted with aryl hydrazines 1b in aqueous alcoholic solvents such as EtOH and water, in the presence of an appropriate base, such as $K_2CO_3$, at temperatures between room temperature and at reflux to give pyrazoles of type 1d. Pyrazoles 1d can be treated with (trimethylsilyl)diazomethane ($TMSCHN_2$, CAS #18107-18-1) in mixed solvent systems such as toluene and MeOH to give 1e (where $R^b$ is Me). Alternatively, compounds 1e can be prepared by subjecting pyrazoles 1d to an alcohol, such as EtOH, with triaryl- or trialkyl-phosphines such as triphenylphosphine and an azodicarboxylate such as DIAD in suitable solvents such as THF at temperatures between 0° C. to room temperature.

Compounds of types 2b and 2c can be synthesized according to Scheme 2.

Scheme 2

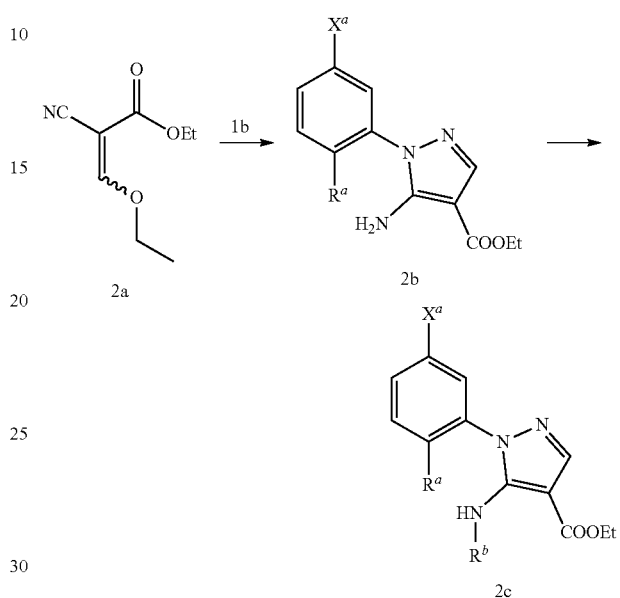

Amino pyrazoles of type 2b can be prepared by mixing ethyl 2-cyano-3-ethoxyacrylate (2a, CAS #94-05-3) and aryl hydrazines 1b with an aqueous organic acid, such as AcOH in water, at temperatures between 50° C. and 100° C. Compounds of type 2c can then be prepared by treating 2b with an approriate base, such as sodium hydride, followed by an alkyl halide such as iodomethane, in a suitable solvent such as DMF.

Compounds of type 3d; wherein $R^c$ is H or $C_1$-$C_4$ alkyl; $R^d$ is H or $C_1$-$C_4$ alkyl; $X^b$ is a halide suitable for palladium mediated coupling; and $W^a$ is —$NH_2$ or —OH can be synthesized according to Scheme 3.

Scheme 3

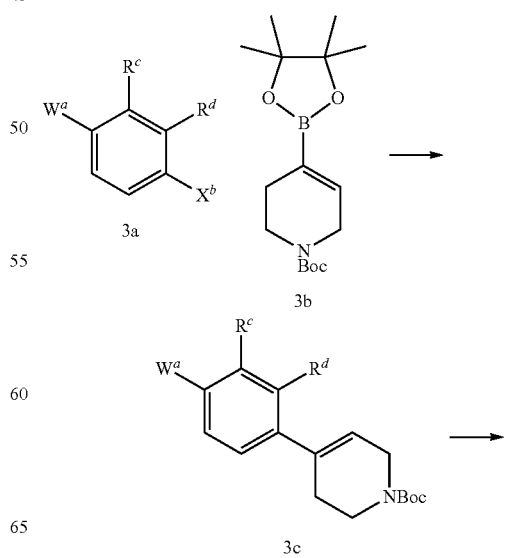

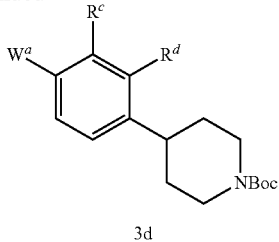

3d 3a can be transformed to 3c utilizing Suzuki-type coupling conditions such as Pd(dppf)Cl$_2$ with boronate 3b (CAS #286961-14-6) in a suitable solvent such as dioxane, and an aqueous base such as sodium carbonate at temperatures between 50° C. and 120° C. Hydrogenation of 3c over catalysts such as palladium on carbon (Pd/C) or platinum oxide, in an appropriate solvent such as MeOH, can provide compounds of type 3d.

Compounds of type 4d can be prepared according to Scheme 4.

Scheme 4

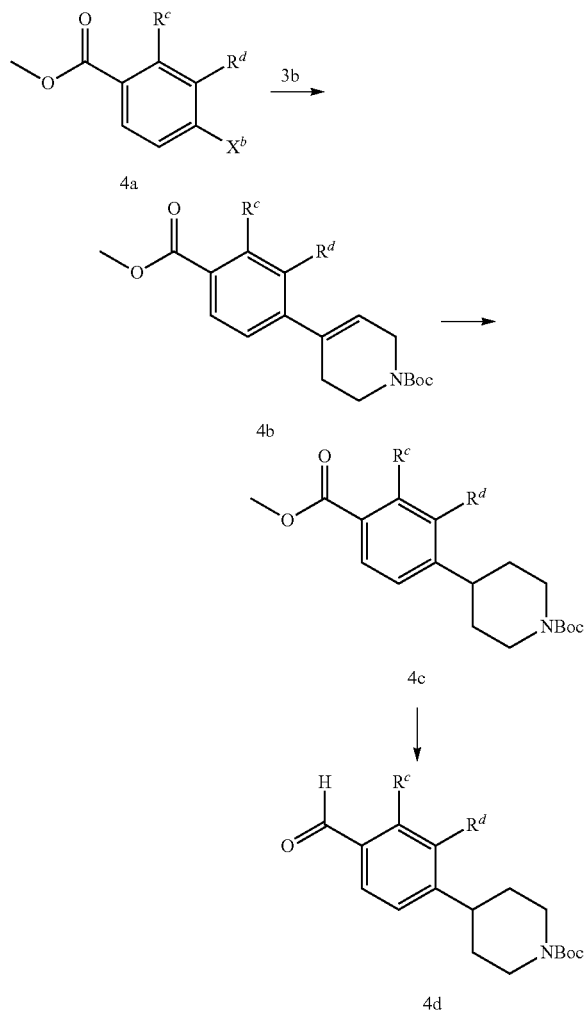

4a can be transformed to esters of type 4b by utilizing Suzuki-type coupling conditions similar to those used to make 3c, with boronate 3b. Esters 4b can undergo hydrogenation over catalysts such as Pd/C or platinum oxide to furnish compounds of type 4c. The compounds 4c can then be reduced by an appropriate reducing reagent such as LiAlH$_4$ in solvents such as THF, preferably at 0° C., to afford the corresponding alcohol, which can be treated under oxidative conditions, such as Dess-Martin periodinane in DCM, can provide aldehydes of the type 4d.

Racemic compounds of type 5b; wherin X$^a$ is a halide suitable to enable a Pd-mediated cross-coupling reaction can be synthesized according to Scheme 5, Scheme 5

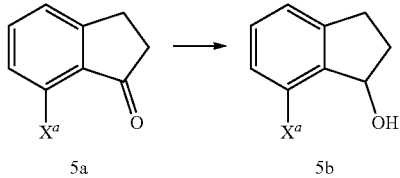

The ketone 5a can be reduced by an appropriate hydride source such as NaBH$_4$ in a suitable solvent such as MeOH at temperatures between 0° C. and room temperature to generate racemic alcohols such as 5b.

Enantiomerically enriched compounds of type 6a can be synthesized according to Scheme 6.

Scheme 6

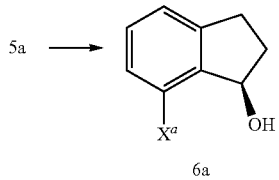

Ketone 5a can be reduced to afford enantiomerically enriched 6a via reaction under transfer hydrogenation conditions, preferably by employing a trimethylamine/formic acid mixture, in the presence of a chiral catalyst such as RuCl[(R,R)-Tsdpen](p-cymene) (CAS #192139-92-7) at temperatures between room temperature and 60° C. in suitable solvent, preferably DMF.

Compounds such as 7a and 7c; wherein R$^e$ is C$_1$-C$_4$ alkyl or C$_3$-C$_5$ cycloalkyl, or hydroxy C$_1$-C$_4$ alkyl can be synthesized according to Scheme 7.

Scheme 7

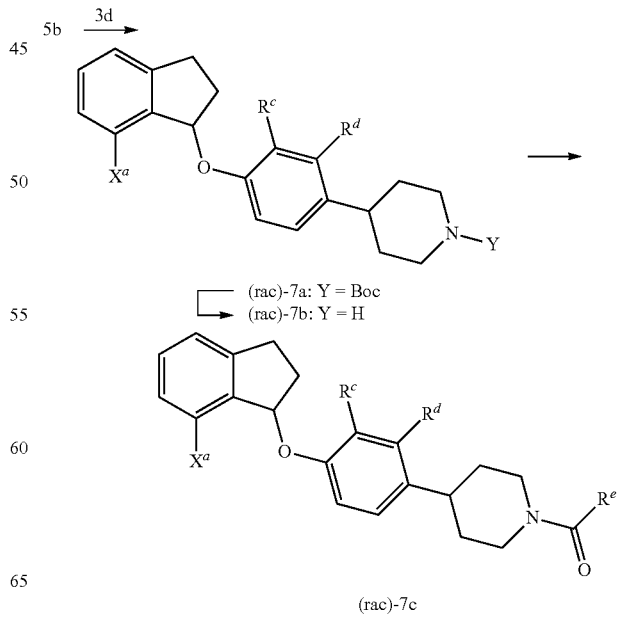

-continued

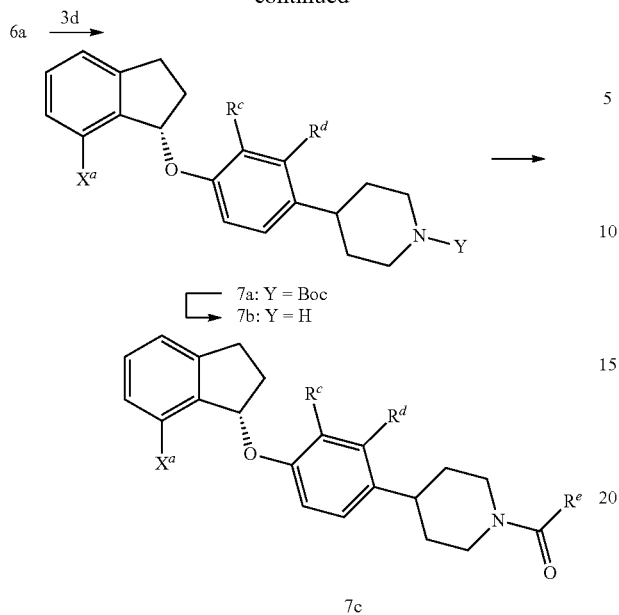

Racemic alcohol 5b can be reacted with a variety of phenol derivatives, such as 3d (where $W^a$=OH), by employing triaryl- or trialkyl-phosphines, preferably tri-n-butyl phosphine, and an azodicarboxylate such as DIAD in suitable solvents such as THF at temperatures between 0° C. to room temperature to afford compounds of the type (rac)-7a. In certain cases, the Boc group of (rac)-7a can then be removed using trimethylsilyl trifluoromethanesulfonate (TMSOTf, CAS #27607-77-8), buffered by a trialkylamine such as DIPEA, in a solvent such as DCM to afford compounds such as (rac)-7b. Finally, (rac)-7b can be transformed into compounds of the type (rac)-7c using carboxylic acids such as cyclopropanecarboxylic acid, under peptide coupling conditions (e.g. HATU and DIPEA).

Alternatively, the enantiomerically enriched compounds of type 7c can be obtained starting from 6a by employing the reaction conditions as outlined above (i.e. 5b→(rac)-7c).

Compounds such as 8a and 8c can be synthesized according to Scheme 8.

Scheme 8

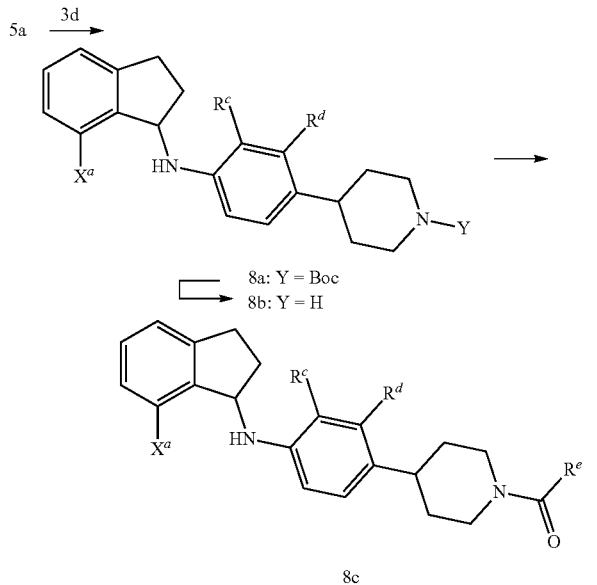

Reaction of ketones of type 5a with anilines of type 3d ($W^a$=NH$_2$) in the presence of acid such as p-toluenesulfonic acid (TsOH), in solvents such as toluene, or a solvent mixture of toluene and dimethylacetaminde, under azeotropic reflux conditions with a Dean-Stark distillation apparatus can provide the corresponding imine. The subsequent imine reduction can be achieved by an appropriate hydride source such as NaB(OAc)$_3$H in the presence of an appropriate acid such as AcOH in solvents such as CH$_2$Cl$_2$ or mixture of CH$_2$Cl$_2$ and alcoholic solvents at temperatures between 0° C. and room temperature to obtain compounds such as 8a. In certain cases, treatment of 8a (when Y=Boc) with an appropriate acid such as TFA in an appropriate solvent such as CH$_2$Cl$_2$ can provide compounds of type 8b. Finally, 8b can be transformed into compounds of type 8c by reaction with carboxylic acids, such as cyclopropanecarboxylic acid, under peptide coupling conditions (e.g., HATU and DIPEA).

Compounds such as 9d can be synthesized according to Scheme 9.

Scheme 9

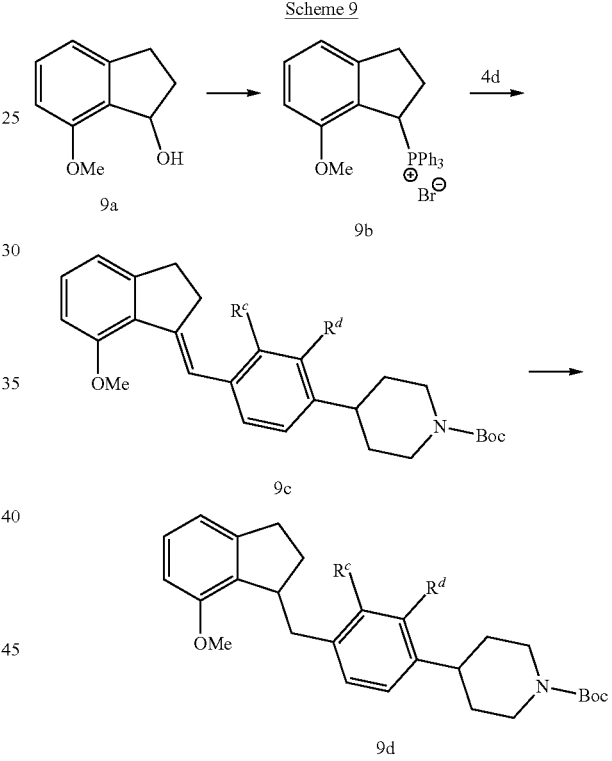

Salt 9b can be prepared from 9a, 7-methoxy-2,3-dihydro-1H-inden-1-ol (CAS #34985-44-9), by reaction with triphenylphosphine hydrobromide in toluene at elevated temperatures, preferably 90° C. Subsequently, the salt 9b can undergo a Wittig-type reaction with aldehydes of type 4d in the presence of a suitable base, such as potassium tert-butoxide, in a mixed solvent system, preferably a mixture of THF and EtOH, at elevated temperatures, preferably at 70° C., to furnish olefins of type 9c. The resulting olefin can be reduced by methods such as a catalytic hydrogenation over Pd/C to afford compounds of type 9d.

Compounds such as 10c, 10d, 10f and 10g can be synthesized according to Scheme 10a and Scheme 10b.

Scheme 10a.

9d →

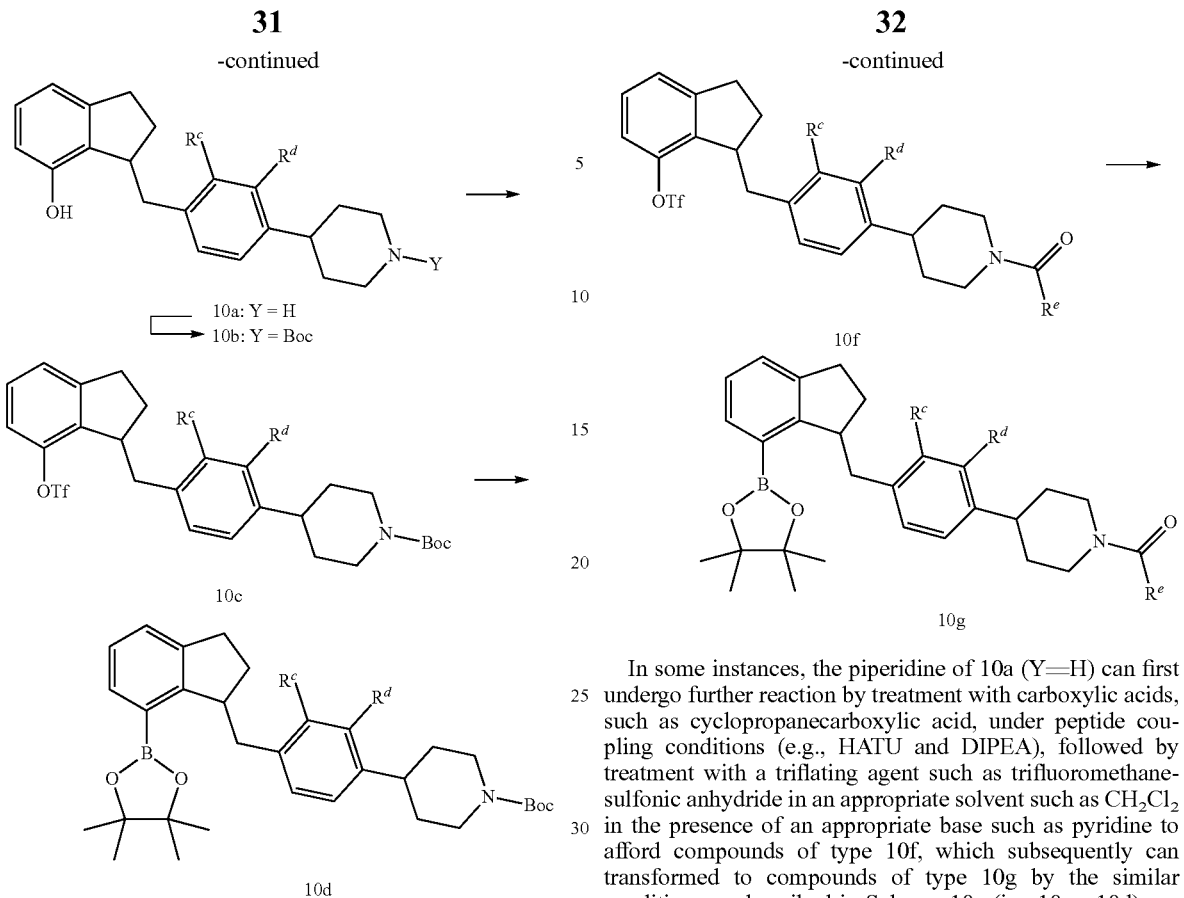

Compounds of type 9d can be treated with a Lewis acid such as BBr₃ at temperatures between −78° C. and 0° C., to afford phenols of type 10a, which can go on to be reacted with Boc₂O in a solvent such as THF with a base such as TEA to obtain phenols of type 10b. The phenols 10b can be transformed to trifluoromethanesulfonates of type 10c by treatment with a triflating agent such as trifluoromethanesulfonic anhydride in an appropriate solvent such as CH₂Cl₂ in the presence of an appropriate base such as pyridine. Subsequent Miyaura-type borylation with 10c can be achieved by reacting with bis(pinacolato)diboron in the presence of catalysts such as Pd(dppf)Cl₂ and a suitable base such as potassium acetate in appropriate solvent such as dioxane at elevated temperatures, preferably 100° C. to afford boronic esters of type 10d.

Scheme 10b

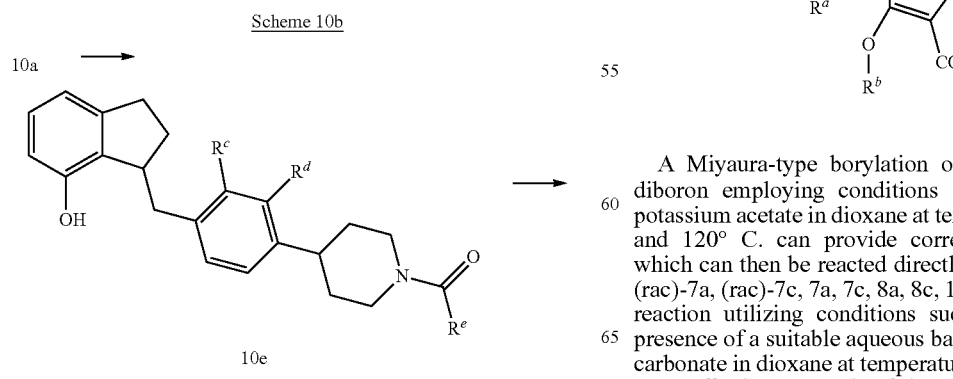

In some instances, the piperidine of 10a (Y=H) can first undergo further reaction by treatment with carboxylic acids, such as cyclopropanecarboxylic acid, under peptide coupling conditions (e.g., HATU and DIPEA), followed by treatment with a triflating agent such as trifluoromethanesulfonic anhydride in an appropriate solvent such as CH₂Cl₂ in the presence of an appropriate base such as pyridine to afford compounds of type 10f, which subsequently can transformed to compounds of type 10g by the similar conditions as described in Scheme 10a (i.e. 10c→10d).

Compounds such as 11a; wherein $W^b$ is O, NH, or CH₂; and $Q^1$ is Boc or C(O)R$^e$ where R$^e$ is C₁-C₄ alkyl, C₃-C₅ cycloalkyl or hydroxyl C₁-C₄ alkyl; can be synthesized according to Scheme 11.

Scheme 11

A Miyaura-type borylation of 1e with bis(pinacolato)diboron employing conditions such as Pd(dppf)Cl₂ and potassium acetate in dioxane at temperatures between 60° C. and 120° C. can provide corresponding boronic esters, which can then be reacted directly with compounds of type (rac)-7a, (rac)-7c, 7a, 7c, 8a, 8c, 10c or 10f by a Suzuki-type reaction utilizing conditions such as Pd(dppf)Cl₂ in the presence of a suitable aqueous base such as aqueous sodium carbonate in dioxane at temperatures between 80° C. to 110° C. to afford compounds of the type 11a.

Compounds such as 12a; wherein $Q^1$ is Boc or $C(O)R^e$ where $R^e$ is $C_1$-$C_4$ alkyl, $C_3$-$C_5$ cycloalkyl, or hydroxy $C_1$-$C_4$ alkyl can be synthesized according to Scheme 12.

Scheme 12

10d or 10g $\xrightarrow{1e}$

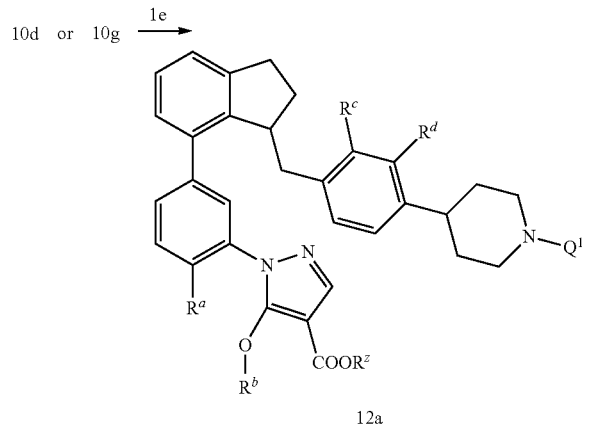

12a

Compounds of type 12a can be obtained by a Suzuki-type reaction of compounds of type 1e with compounds of type 10d or 10g under a variety of the Suzuki-type coupling conditions employing such catalysts as $Pd(PPh_3)_4$ or $Pd(dppf)Cl_2$, in the presence of a suitable aqueous base such as aqueous sodium carbonate in dioxane at temperatures between 80° C. to 110° C.

Compounds such as 13c; wherein $W^c$ is O, NH, or $CH_2$; $R^e$ is $C_1$-$C_4$ alkyl, $C_3$-$C_5$ cycloalkyl, or hydroxy $C_1$-$C_4$ alkyl can be synthesized according to Scheme 13.

Scheme 13

11a or 12a $\longrightarrow$
($Q^1$ = Boc)

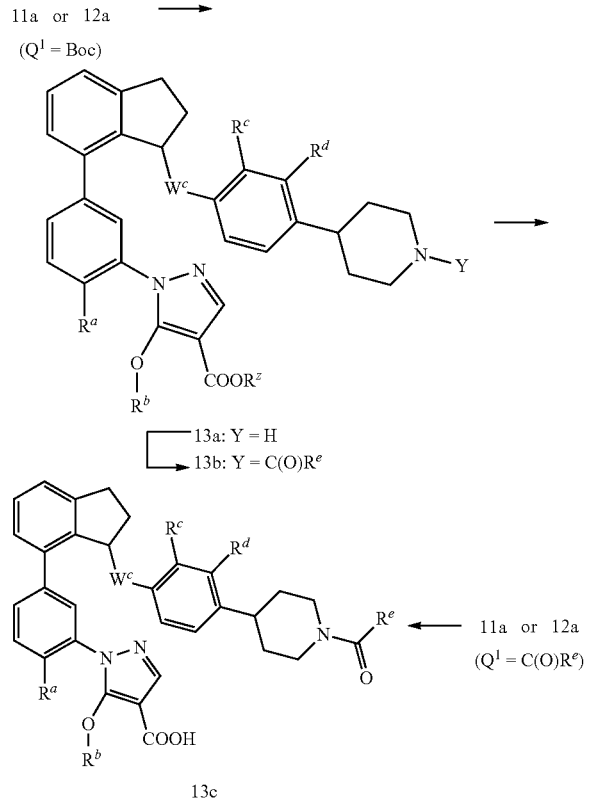

13a: Y = H
13b: Y = C(O)$R^e$ $\longleftarrow$ 11a or 12a
($Q^1$ = C(O)$R^e$)

13c

Treatment of 11a or 12a (when $Q^1$=Boc and $W^c$=NH or $CH_2$) with suitable acids, such as HCl in dioxane, in solvents such as $CH_2Cl_2$ or dioxane at temperatures between 0° C. to room temperature can provide compounds such as 13a. In certain cases, treatment of 11a (when $Q^1$=Boc and $W^c$=O) with a Lewis acid, preferably trimethylsilyl trifluoromethanesulfonate (TMSOTf), and a base such as TEA, in a solvent such as $CH_2Cl_2$ preferably at 0° C. can provide compounds such as 13a. Compounds 13a can then be transformed to compounds of type 13b by reactions with carboxylic acids, such as cyclopropanecarboxylic acid, under peptide coupling conditions (e.g., HATU and DIPEA). Saponification of 13b can be accomplished employing conditions such as aqueous LiOH in a solvent mixture of MeOH and THF at temperatures between room temperature to 70° C. to afford compounds of the type 13c. Alternatively, 11a or 12a ($Q^1$=C(O)$R^e$) can be saponified directly, using the above described conditions, to afford compounds of the type 13c.

Compounds such as 14b; wherein $R^f$ is H or $C_1$-$C_4$ alkyl; $W^c$ is O, NH, or $CH_2$; can be synthesized according to Scheme 14.

Scheme 14

7c or 8c $\xrightarrow{\text{Miyaura Borylation}}$ $\xrightarrow{\text{2b or 2c}}$ 10g $\xrightarrow{\text{2b or 2c}}$

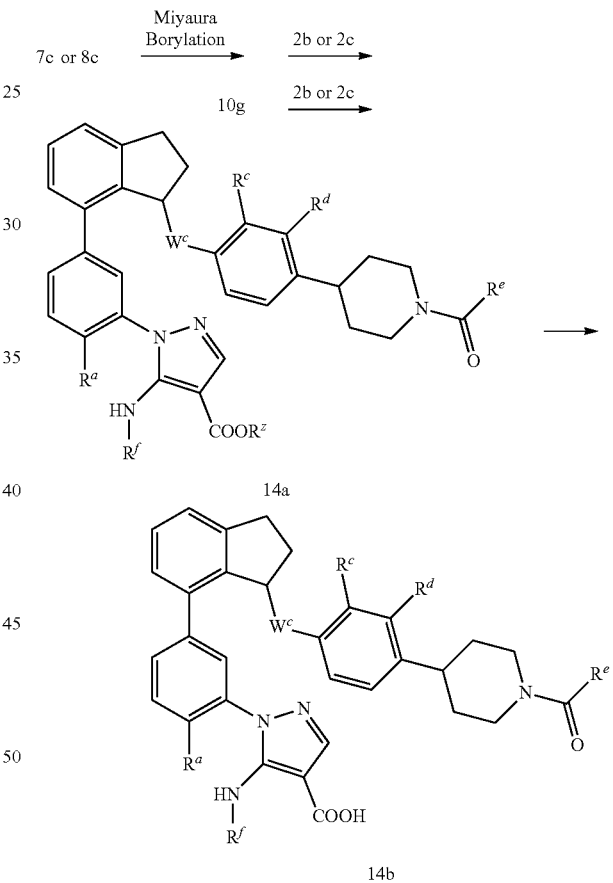

14a

14b

A Miyaura-type borylation of amides of the type 7c or 8c ($W^c$=O or NH) with bis(pinacolato)diboron employing conditions such as $Pd(dppf)Cl_2$ and potassium acetate in dioxane at temperatures between 60° C. and 120° C. can provide corresponding boronic ester, which can then be reacted directly with compounds of the type 2b or 2c by a Suzuki-type reaction utilizing conditions such as $Pd(dppf)Cl_2$ in the presence of a suitable aqueous base such as aqueous sodium carbonate in dioxane at temperatures between 80° C. to 110° C. to afford compounds such as 14a. Saponification of 14a can be accomplished employing conditions such as aqueous LiOH in a solvent mixture of MeOH and THF at temperatures between room temperature to 70° C. to afford compounds of the type 14b.

Alternatively, boronic ester 10g (W$^c$=CH$_2$), can undergo a Suzuki-type reaction with halides, such as 2b or 2c, to afford compounds type 14a, which subsequently can be saponified to afford 14b in accordance with the method described above.

Compounds of type 15d; wherein R$^g$ is C$_1$-C$_4$ alkyl can be synthesized according to Scheme 15.

of an appropriate source of hydride, preferably NaBH$_3$CN at temperatures between 90° C. and 130° C., to obtain compounds such as 16a. Coupling of 16a and N-oxides such as 15d can be accomplished using bromotripyrrolidinophosphonium hexafluorophosphate (PyBroP®, CAS #132705-51-2) and a suitable trialkyl amine base such as DIPEA in dioxane at temperatures between room temperature and 45° C. to afford compounds of type 16b.

Enantiomerically enriched compounds such as 17e can be synthesized according to Scheme 17 and can be used in place of the racemic variant, 16b.

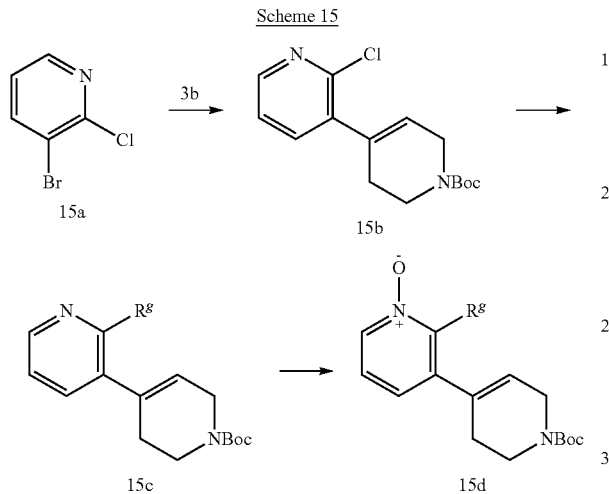

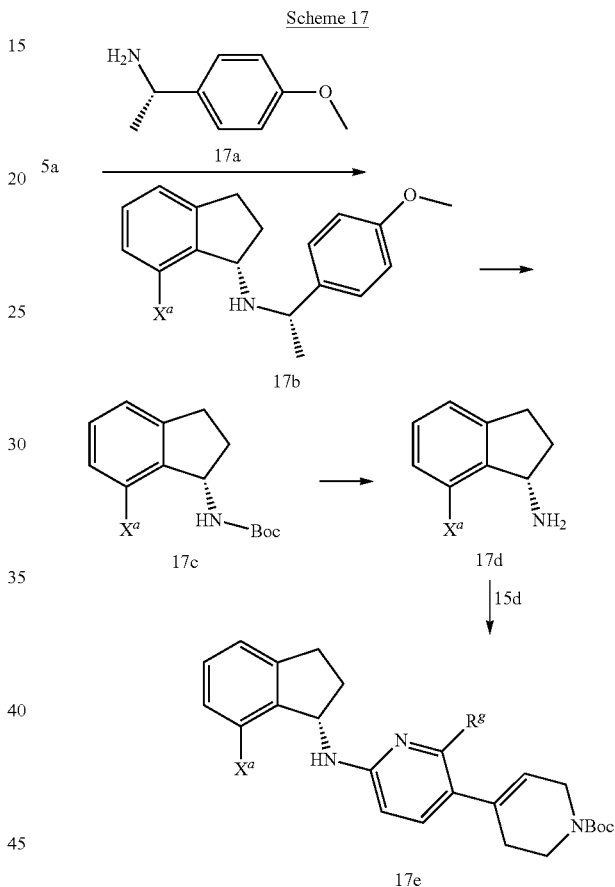

15a can be transformed to 15b utilizing a Suzuki-type coupling with boronate 3b. 15b can then be treated with dialkylzinc (where R$^g$ is alkyl) under Negishi-type coupling conditions employing a catalyst such as Pd(dppf)Cl$_2$ and a base such as potassium carbonate in an appropriate solvent such as THF at temperatures between 0° C. and 50° C. to provide compounds of type 15c, which subsequently can be treated with m-CPBA to obtain N-oxides 15d.

Compounds of type 16b wherein X$^a$ is a halide that is suitable for palladium mediated couplings can be synthesized according to Scheme 16.

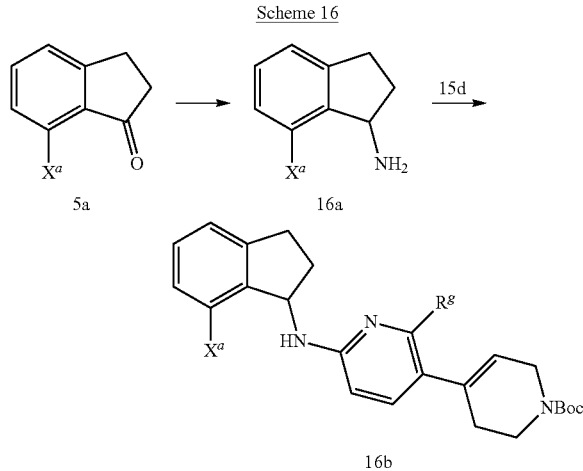

Indanones such as 5a can be treated with ammonium acetate in an alcoholic solvent such as EtOH in the presence Indanones such as 5a can be treated with the enantiomerically enriched (S)-1-(4-methoxyphenyl)ethan-1-amine (CAS #41851-59-6, 17a) in the presence of a catalytic acid such as TsOH in a solvent such as toluene at reflux employing azeotropic conditions using a Dean-Stark distillation apparatus. The resulting imine can then be subjected to an appropriate source of hydride such as sodium triacetoxyborohydride in the presence of an acid such as AcOH in a solvent such as CH$_2$Cl$_2$ at temperatures between 0° C. and room temperature, to obtain diastereomerically enriched 17b. The diastereomeric enrichment of 17b can be further enhanced by silica gel chromatography. Treatment of 17b under suitable conditions, such as cerium ammonium nitrate (CAN) in an aqueous organic solvent, such as ACN and water, can result in the corresponding amine which can be directly treated with Boc-anhydride and a base such as NaHCO$_3$, leading to compounds such as 17c. Boc deprotection can be accomplished using an acid such as HCl in dioxane, which can provide enantiomerically enriched compounds such as 17d. Enantiomerically enriched 17e can be prepared from 17d and 15d as described in Scheme 16 (16a→16b).

Compounds such as 18d; wherein $W^d$ is $C_1$-$C_4$ alkoxy; $R^e$ is $C_1$-$C_4$ alkyl, $C_3$-$C_5$ cycloalkyl, or hydroxy $C_1$-$C_4$ alkyl can be synthesized according to Scheme 18.

$X^a$ is a halide that is suitable for palladium mediated couplings can be synthesized according to Scheme 19.

Scheme 19

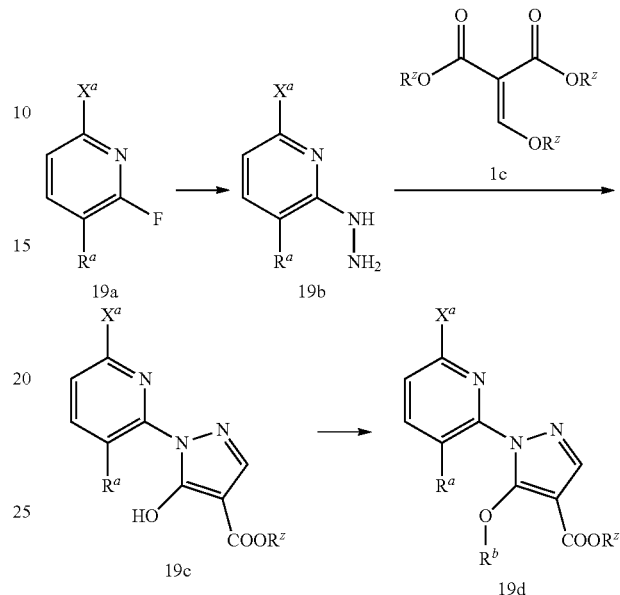

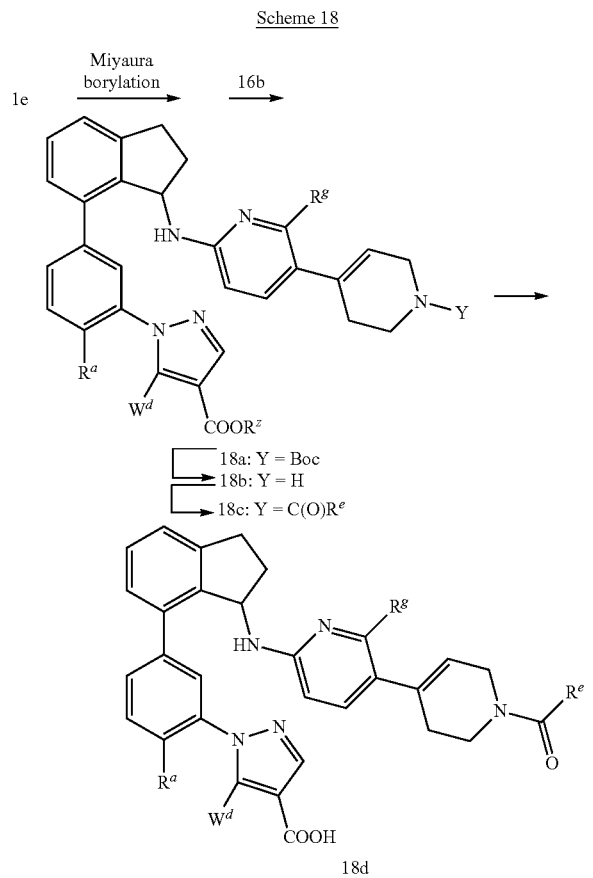

Hydrazines 19b are either commercially available or can be prepared by treating fluoropyridines such as 19a with hydrazine hydrate in EtOH at temperatures between 80° C. and 100° C. Malonate derivatives 1c can be reacted with hydrazines 19b in aqueous alcoholic solvents such as EtOH and water, in the presence of an appropriate base, such as $K_2CO_3$, at temperatures between room temperature and at reflux to give pyrazoles of type 19c. Pyrazoles 19c can be treated with (trimethylsilyl)diazomethane (TMSCHN$_2$) in mixed solvent systems such as toluene and MeOH to give 19d. Alternatively, compounds 19d can be prepared by subjecting pyrazoles 19c to an alcohol, such as EtOH, with triaryl- or trialkyl-phosphines such as triphenylphosphine and an azodicarboxylate such as DIAD in suitable solvents such as THF at temperatures between 0° C. to room temperature.

Compounds such as 20a can be synthesized according to Scheme 20.

A Miyaura-type borylation of compounds such as 1e with bis(pinacolato)diboron employing conditions such as Pd(dppf)Cl$_2$ and potassium acetate in dioxane at temperatures between 60° C. and 120° C. can provide corresponding boronic ester, which can then be reacted directly with racemic compounds 16b by a Suzuki-type reaction utilizing conditions such as Pd(dppf)Cl$_2$ in the presence of a suitable aqueous base such as aqueous sodium carbonate in dioxane at temperatures between 80° C. to 110° C. to afford compounds such as 18a. 18a can be transformed to amides such as 18c by treatment with a suitable acid such as TFA in a solvent such as CH$_2$Cl$_2$, followed by reaction with a carboxylic acid such as cyclopropanecarboxylic acid under peptide coupling conditions (e.g. HATU and DIPEA) to provide 18c. Saponification of 18c can be effected using an aqueous base such as LiOH in a solvent mixture of MeOH and THF at temperatures between room temperature and 70° C. to afford racemic compounds of the type 18d.

Alternatively, enantiomerically enriched compounds of type 18d can be prepared starting from compounds of type 17e instead of 16b by employing the method described above.

Compounds such as 19e; wherein $R^a$ is H, $C_1$-$C_4$ alkyl, or $C_1$-$C_4$ alkoxy; $R^b$ is $C_1$-$C_4$ alkyl; $R^z$ in methyl or ethyl; and Scheme 20

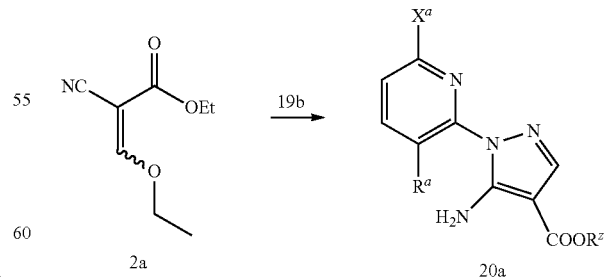

Amino pyrazoles such as 20a can be prepared by mixing ethyl 2-cyano-3-ethoxyacrylate (2a) and hydrazines such as 19b with an aqueous organic acid, such as AcOH in water, at temperatures between 50° C. and 100° C.

Compounds such as 21b; wherein $R^a$ is H, $C_1$-$C_4$ alkyl, or $C_1$-$C_4$ alkoxy; $R^c$ is H or $C_1$-$C_4$ alkyl; $R^d$ is H or $C_1$-$C_4$ alkyl; and $R^z$ is methyl or ethyl can be synthesized according to Scheme 21.

Scheme 21

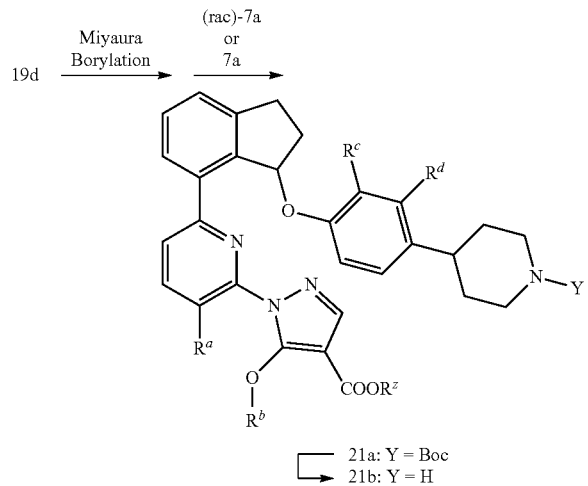

21a: Y = Boc
21b: Y = H

A Miyaura-type borylation of 19d with bis(pinacolato) diboron employing conditions such as Pd(dppf)Cl$_2$ and potassium acetate in dioxane at temperatures between 60° C. and 120° C. can provide corresponding boronic esters, which can then be reacted directly with (rac)-7a by a Suzuki-type reaction utilizing conditions such as Pd(dppf)Cl$_2$ in the presence of a suitable aqueous base such as aqueous sodium carbonate in dioxane at temperatures between 80° C. to 110° C. to afford racemic compounds such as 21a. Treatment of 21a with trimethylsilyl trifluoromethanesulfonate (TMSOTf) in the presence of a base such as DIPEA, in a solvent such as CH$_2$Cl$_2$ at temperatures, preferably at 0° C., can provide racemic compounds such as 21b.

Alternatively, the enantiomerically enriched compounds of type 21b can be obtained starting from 19d and enantiomerically enriched 7a by employing the reaction conditions as outlined above.

Compounds such as 22b and 22c can be synthesized according to Scheme 22a and Scheme 22b.

Scheme 22a

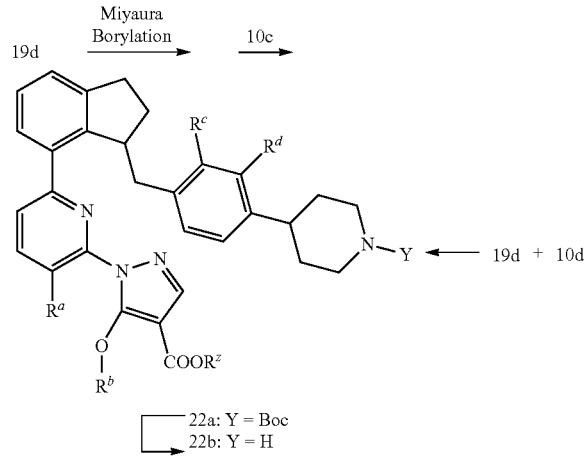

22a: Y = Boc
22b: Y = H

A Miyaura-type borylation of 19d followed by Suzuki-type coupling conditions with 10c, under conditions similar to the sequence described in Scheme 21 can afford compounds of the type 22a. Alternatively, 19d and 10d can be coupled using Suzuki-type conditions, such as Pd(PPh$_3$)$_4$ in the presence of a suitable aqueous base such as aqueous sodium carbonate in dioxane at temperatures between 80° C. to 110° C., to obtain compounds of the type 22a. Treatment of 22a with suitable acids, such as TFA in solvents such as CH$_2$Cl$_2$ at temperatures between 0° C. to room temperature can provide compounds such as 22b.

Scheme 22b

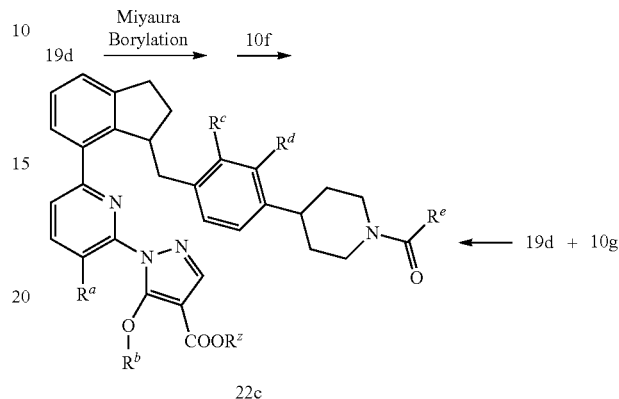

Compounds of the type 22c can be prepared by a Miyaura-type borylation of 19d followed by Suzuki-type coupling conditions with 10f, under conditions similar to the sequence described in Scheme 21. Alternatively, 19d and 10g can be coupled using Suzuki-type conditions as described in Scheme 22a to obtain 22c.

Compounds such as 23b; wherein $W^e$ is O or CH$_2$; $R^e$ is $C_1$-$C_4$ alkyl, $C_3$-$C_5$ cycloalkyl, or hydroxy $C_1$-$C_4$ alkyl can be synthesized according to Scheme 23.

Scheme 23

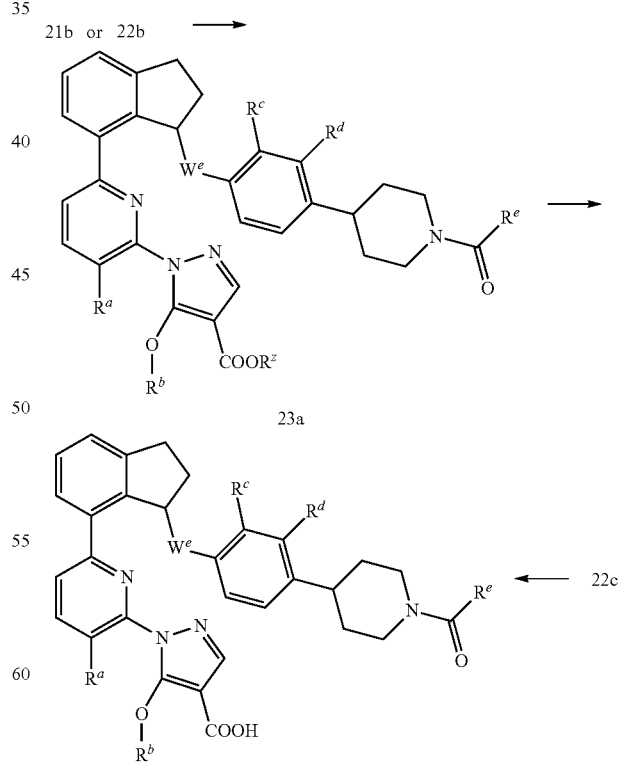

Compounds 21b or 22b can be transformed to compounds such as 23a by reactions with carboxylic acids, such as cyclopropanecarboxylic acid, under peptide coupling conditions (e.g., HATU and DIPEA). Saponification of 23a can be accomplished employing conditions such as aqueous LiOH in a solvent mixture of MeOH and THF at temperatures between room temperature to 70° C. to afford compounds of the type 23b. Alternatively, 22c can be saponified directly using the above conditions to obtain 23b.

Compounds such as 24b wherein $W^e$ is O, $CH_2$, or NH can be synthesized according to Scheme 24.

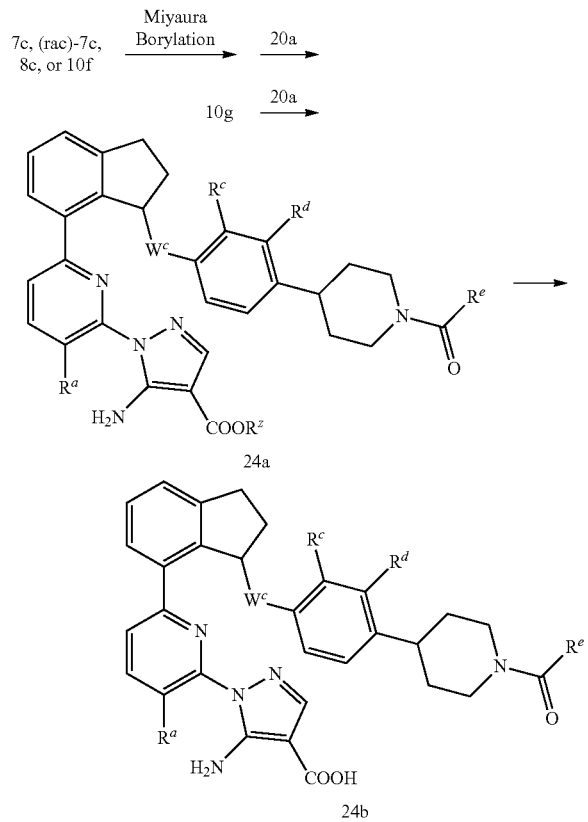

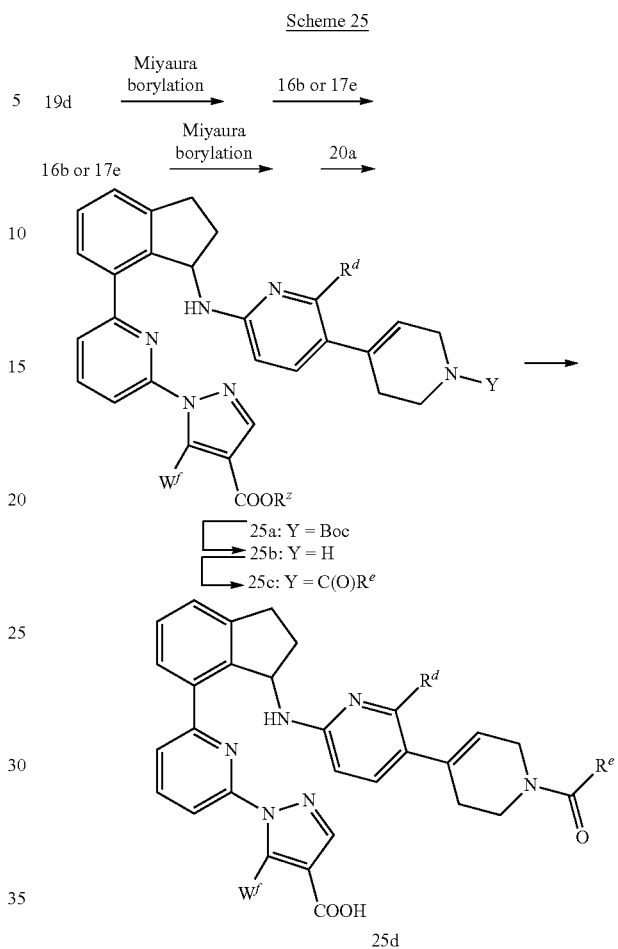

A Miyaura-type borylation of amides of the type 7c, (rac)-7c, 8c, or 10f with bis(pinacolato)diboron employing conditions such as $Pd(dppf)Cl_2$ and potassium acetate in dioxane at temperatures between 60° C. and 120° C. can provide corresponding boronic ester, which can then be reacted directly with compounds of the type 20a by a Suzuki-type reaction utilizing conditions such as $Pd(dppf)Cl_2$ in the presence of a suitable aqueous base such as aqueous sodium carbonate in dioxane at temperatures between 80° C. to 110° C. to afford compounds such as 14a. Alternatively, boronic esters 10g should be able to be coupled with compounds of the type 20a using Suzuki-type coupling conditions as described in Scheme 22a to provide compounds such as 24a. Saponification of 24a can be accomplished employing conditions such as aqueous LiOH in a solvent mixture of MeOH and THF at temperatures between room temperature to 70° C. to afford compounds of the type 24b.

Compounds such as 25d; wherein $W^f$ is $C_1$-$C_4$ alkoxy or $NH_2$; can be synthesized according to Scheme 25.

A Miyaura-type borylation of compounds such as 19d with bis(pinacolato)diboron employing conditions such as $Pd(dppf)Cl_2$ and potassium acetate in dioxane at temperatures between 60° C. and 120° C. can provide corresponding boronic ester, which may then be reacted directly with racemic 16b by a Suzuki-type reaction conditions such as $Pd(dppf)Cl_2$ in the presence of a suitable aqueous base, such as aqueous sodium carbonate, in a suitable solvent, such as dioxane, at temperatures between 80° C. to 110° C. to afford racemic 25a. Alternatively, 16b should react under Miyaura-type reaction conditions as described above, then directly react with 20a under Suzuki-type reaction conditions as described above, to afford racemic 25a. Carbamates of type 25a should transform to amides such as 25c by treatment with a suitable acid such as TFA in a solvent such as $CH_2Cl_2$, followed by reaction with a carboxylic acid, such as cyclopropanecarboxylic acid, under peptide coupling conditions (e.g. HATU and DIPEA) to provide 25c. Saponification of 25c should be effected by an aqueous base such as LiOH in a solvent mixture of MeOH and THF at temperatures between room temperature and 70° C. to afford compounds of the type 25d.

Alternatively, enantiomerically enriched compounds of type 25d should be accessible starting from compounds of type 17e instead of 16b by employing the methods described above.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Compositions of the present invention may be utilized in various dosage regimens known to those of skill in the art. Such dosing frequency is maintained for a varying duration of time depending on the therapeutic regimen. The duration of a particular therapeutic regimen may vary from one-time dosing to a maintenance regimen that extends for a month, year or more. One of ordinary skill in the art would be familiar with determining a therapeutic regimen for a specific indication. Preferred dosage regimens of the present invention include, but are not limited to, once a day dosing and twice a day dosing.

In the methods for the treatment of ocular disease and particularly for the treatment of glaucoma, set forth herein, administration to a subject of a composition of the present invention may be by various methods known to those of skill in the art, including, but not limited to, topical, subconjunctival, periocular, retrobulbar, subtenon, intraocular, subretinal, posterior juxtascleral, or suprachoroidal administration. In preferred embodiments, administration of a composition of the present invention is by topical administration to the ocular surface.

It is contemplated that the concentration of the sGC activator in the compositions of the present invention can vary, but is preferably 0.001 to 3.0 w/v % and more preferably 0.001-0.1 w/v %. The most preferred concentration range is from 0.01-0.1 w/v % and the most preferred concentration is about 0.01 w/v %. The sGC activators of the present invention comprise the pharmaceutically useful hydrates and salts of such compounds and stereoisomers (where applicable), and may be formulated with a pharmaceutically acceptable vehicle.

The methods of treating glaucoma may include administering the sGC activator compound by a technique selected from the group consisting of: topical ocular administration, periocular injection, sub-conjunctival injection, sub-tenon injection, intracameral injection, intravitreal injection, intracanalicular injection, implanting delivery device in the cul-de-sac, implanting delivery device adjacent to the sclera, implanting delivery device within the eye, oral administration, intravenous administration, subcutaneous administration, intramuscular administration, parenteral administration, dermal administration, and nasal administration.

In certain aspects of the invention, compounds of the invention may be formulated in either fixed and unfixed combinations of two therapeutic agents effective in the treatment of glaucoma wherein one therapeutic agent is sGC activator disclosed supra and the second therapeutic agent is an efficacious glaucoma drug. In other embodiments, a pharmaceutical composition of the invention comprising a sGC activator can be administered to a patient alone or in combination with other IOP-lowering agents to increase the potency, efficacy and/or duration of the IOP reduction. In certain preferred combinations, the second IOP-lowering agent is selected from carbonic anhydrase inhibitors, beta-blockers, prostaglandins, alpha-2 agonists, serotonin-2 agonists, alpha-1 antagonists, dopamine agonists, Rho kinase inhibitors, myosin-II Ca2+ATPase inhibitors, matrix metalloproteinase activators, activator protein-1 (AP-1) activators, natriuretic peptide receptor-B agonists, phosphodiesterase inhibitors, K+-channel blockers and maxi-K-channel activators. The combination therapy of the invention provides the benefit of lowering IOP by two mechanisms, including inducing uveoscleral outflow of aqueous humor and inhibiting aqueous humor inflow, which can allow for reduced dosages of the compounds thereby lowering the risk of side effects.

Pharmaceutical compositions of the invention can also be advantageously combined with suitable neuroprotective agents such as memantine, eliprodil, Ca2+-channel blockers, and betaxolol.

In a further aspect of the invention, the sGC activator may be administered alone or in combination with a second therapeutic agent which is suitable for the treatment of glaucoma. Certain preferred second therapeutic agents include beta-blockers, prostaglandin analogs, carbonic anhydrase inhibitors, α2 agonists, miotics, PDE-V inhibitors, Rh0 kinase inhibitors and neuroprotectants. In one preferred combination, a prostaglandin F2α analogue selected from the group consisting of Latanoprost and Travoprost is administered in combination with sGC activator of Formula (I) or subformulae thereof. In another preferred combination, a PDE-V inhibitor selected from the group consisting of Sildenafil, Tadalafil, Vardenafil, Udenafil, Avanafil, Lodenafil and Mirodenafil is administered in combination with a sGC activator of Formula (I) or subformulae thereof. In yet another preferred combination, a sGC activator of Formula (I) or subformulae thereof is administered in combination with a sGC stimulator (such as Riociguat) or a NO precursor (such as sodium nitroprusside or nitroglycerine). In another preferred combination, a sGC activator of Formula (I) or subformulae thereof is administered in combination with a Rho-kinase inhibitor (such as AR-13324 alone or combination of AR-13324 and Latanoprost).

In a further embodiment of the invention, a sGC activator of Formula (I) is administered in combination with a carbonic anhydrase inhibitor (such as Brinzolamide) for the treatment of glaucoma or to reduce IOP. In another embodiment, a sGC activator of Formula (I) is administered in combination with a α2 adrenergic agonist (such as Brimonidine) for the treatment of glaucoma or to reduce IOP. In a particularly preferred combination therapy, a sGC activator of Formula (I) is administered in combination with a fixed combination of Brimonidine and Brinzolamide (such as SIMBRINZA™ from Alcon, Fort Worth, Tex.) for the treatment of glaucoma or to reduce IOP.

In certain embodiments, a sGC activator and the second pharmaceutical agent are administered concurrently in separate pharmaceutical compositions. In other embodiments, a sGC activator and the second pharmaceutical agent are administered formulated together in a pharmaceutical composition. In yet other embodiments, the sGC activator and the second pharmaceutical agent are administered sequentially in separate pharmaceutical compositions.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

In addition to a sGC activator, the compositions of the present invention optionally comprise one or more excipients. Excipients commonly used in pharmaceutical compositions include, but are not limited to, tonicity agents, preservatives, chelating agents, buffering agents, surfactants and antioxidants. Other excipients comprise solubilizing agents, stabilizing agents, comfort-enhancing agents, polymers, emollients, pH-adjusting agents and/or lubricants. Any of a variety of excipients may be used in compositions of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, xanthan gum, carrageenin, agar and acacia, starch derivatives, such as starch acetate and hydroxypropyl cellulose or starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the sGC activator. In preferred embodiments, excipients are selected on the basis of their inertness towards the sGC activator.

Relative to ophthalmic formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as Procol® CS20 and poloxamers such as Pluronic® F68. Suitable antioxidants include, but are not limited to, sulfites, ascorbates, butylated hydroxyanisole (BHA) and butylated hydroxytoluene (BHT).

The compositions set forth herein may comprise one or more preservatives. Examples of such preservatives include p-hydroxybenzoic acid ester, sodium chlorite, benzalkonium chloride, parabens such as methylparaben or propylparaben, alcohols such as chlorobutanol, benzyl alcohol or phenyl ethanol, guanidine derivatives such as polyhexamethylene biguanide, polymeric quaternary ammonium compounds such as Onamer M and Polyquaterium-1 (POLYQUAD® from Alcon), sodium perborate, or sorbic acid. In certain embodiments, the composition may be self-preserved that no preservation agent is required.

In preferred compositions a sGC activator of the present invention will be formulated for topical application to the eye in aqueous solution in the form of drops. The term "aqueous" typically denotes an aqueous composition wherein the composition is >50%, more preferably >75% and in particular >90% by weight water. These drops may be delivered from a single dose ampoule which may preferably be sterile and thus render bacteriostatic components of the composition unnecessary. Alternatively, the drops may be delivered from a multi-dose bottle which may preferably comprise a device which extracts any preservative from the composition as it is delivered, such devices being known in the art.

In other aspects, components of the invention may be delivered to the eye as a concentrated gel or a similar vehicle, or as dissolvable inserts that are placed beneath the eyelids. In yet other aspects, components of the invention may be delivered to the eye as ointments, water-in-oil and oil-in-water emulsions, solutions, or suspensions.

The compositions of the present invention, and particularly the topical compositions, are preferably isotonic or slightly hypotonic in order to combat any hypertonicity of tears caused by evaporation and/or disease. This may require a tonicity agent to bring the osmolality of the composition to a level at or near 210-320 milliosmoles per kilogram (mOsm/kg). The compositions of the present invention generally have an osmolality in the range of 220-320 mOsm/kg, and preferably have an osmolality in the range of 235-300 mOsm/kg. The ophthalmic compositions will generally be formulated as sterile aqueous solutions.

In certain embodiments, a sGC activator of the present invention is formulated in a composition that comprises one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; guars, such as HP-guar and other guar derivatives, and carbomers, such as carbomer 934P, carbomer 941, carbomer 940 and carbomer 974P. Certain compositions of the present invention may be used with contact lenses or other ophthalmic products.

In certain embodiments, the compositions set forth herein have a viscosity of 0.5-100 cps, preferably 0.5-50 cps, and most preferably 1-20 cps. These viscosities insure that the product is comfortable, does not cause blurring, and is easily processed during manufacturing, transfer and filling operations.

Preferred compositions are prepared using a buffering system that maintains the composition at a pH of about 3 to a pH of about 8.0, preferably 5.5-7.5, and most preferably 6.0-7.4. Topical compositions (particularly topical ophthalmic compositions) are preferred which have a physiological pH matching the tissue to which the composition will be applied or dispensed.

The following examples are presented to further illustrate selected embodiments of the present invention.

TOPICAL OCULAR FORMULATION EXAMPLE

| Ingredient | Concentration (w/v %) |
| --- | --- |
| sGC activator | 0.1% |
| Dibasic Sodium Phosphate | 0.2% |
| Sodium Chloride | 0.75% |
| Disodium EDTA | 0.01% |
| Polysorbate 80 | 0.05% |
| Benzalkonium Chloride Solution | 0.01% |
| Hydroxypropyl Methylcellulose | 0.5% |

The compounds of formula I in free form or in pharmaceutically acceptable salt form, exhibit valuable pharmacological properties, e.g. sGC modulating properties, e.g. as indicated in vitro and in vivo tests as provided in the next sections, and are therefore indicated for therapy or for use as research chemicals, e.g. as tool compounds. More particularly, the compounds of formula I, in free form or in pharmaceutically acceptable salt form, activate sGC which is suitable for use in treatment of disease.

In one preferred use, the compounds of Formula I are suitable for use in lowering intra-ocular pressure (IOP) and in the treatment of glaucoma. The compounds of the invention may be used alone or in combination with a second therapeutic agent for the treatment of glaucoma. The embodiment further provides methods of treating glaucoma or reducing intraocular pressure in a subject, the method comprising administering a compound of Formula I alone or in combination with a second therapeutic agent. In certain aspects, the method contemplates to topical ocular administration of the compound of Formula I to the subject in need of such therapy. In preferred aspects, the method comprises administration of the compound of Formula I as a monotherapy. In certain other aspects, the method comprises the co-administration (either concomitantly or sequentially) of a compound of Formula I and a PDE-V inhibitor.

Compounds of the invention may also be useful in the treatment of an indication selected from: kidney disease, urologic disorders hypertension, atherosclerosis, peripheral artery disease, restenosis, stroke, heart failure, coronary vasospasm, cerebral vasospasm, ischemia/reperfusion injury, thromboembolic pulmonary hypertension, pulmonary arterial hypertension, stable and unstable angina, thromboembolic disorders. In addition, the compounds of the invention have the potential to treat renal disease, diabetes, fibrotic disorders (including those of the liver, kidney and lungs), urologic disorders (including overactive bladder), benign prostatic hyperplasia, erectile dysfunction, neuropathic pain and neurological disorders (Including Alzheimer's disease and Parkinson's disease). Treatment with an sGC activator of the invention may further provide benefit in the treatment of inflammatory disorder such as psoriasis, multiple sclerosis, arthritis, asthma and chronic obstructive pulmonary disease.

Thus, as a further embodiment, the present invention provides the use of a compound of formula (I) in therapy. In a further embodiment, the therapy is selected from a disease which may be treated by activation of sGC. In a preferred application, the disease is selected from the afore-mentioned list, suitably glaucoma.

In another embodiment, the invention provides a method of treating a disease which is treated by activation of sGC comprising administration of a therapeutically acceptable amount of a compound of formula (I) or a salt thereof. In a further embodiment, the disease is selected from the afore-mentioned list, suitably glaucoma. Systemic exposure following topical ocular administration of the compounds of the invention, e.g., compounds of Formula (I) is minimized due to the high systemic clearance of the compounds of the invention. The combination of high sGC activation and rapid systemic clearance make these compounds particularly suitable to use in the treatment of glaucoma.

In a particularly preferred use, a compound of formula (I) selected from the group consisting of (+)-(R)-1-(3-(3-(4-(1-(Cyclopropanecarbonyl)piperidin-4-yl)-3-ethylbenzyl)-2,3-dihydro-1H-inden-4-yl)phenyl)-5-methoxy-1H-pyrazole-4-carboxylic acid, (+)-1-(3-(3-((4-(1-(Cyclopropanecarbonyl)piperidin-4-yl)-3-ethylphenyl)amino)-2,3-dihydro-1H-inden-4-yl)phenyl)-5-methoxy-1H-pyrazole-4-carboxylic acid, and (+)-1-(3-(3-((1'-(cyclopropanecarbonyl)-2-ethyl-1',2',3',6-tetrahydro-[3,4'-bipyridin]-6-yl)amino)-2,3-dihydro-1H-inden-4-yl)phenyl)-5-methoxy-1H-pyrazole-4-carboxylic acid or a pharmaceutically acceptable salt thereof are suitable for use in lowering intra-ocular pressure (IOP) and in the treatment of glaucoma.

In another aspect of the invention, therapeutic combinations are provided which include a compound of Formula I of the invention and a second therapeutic agent for the treatment of glaucoma. In certain preferred combinations, the compound of Formula (I) is selected from a group consisting of (+)-(R)-1-(3-(3-(4-(1-(cyclopropanecarbonyl)piperidin-4-yl)-3-ethylbenzyl)-2,3-dihydro-1H-inden-4-yl)phenyl)-5-methoxy-1H-pyrazole-4-carboxylic acid, (+)-1-(3-(3-((4-(1-(cyclopropanecarbonyl)piperidin-4-yl)-3-ethylphenyl)amino)-2,3-dihydro-1H-inden-4-yl)phenyl)-5-methoxy-1H-pyrazole-4-carboxylic acid, and (+)-1-(3-(3-((1'-(cyclopropanecarbonyl)-2-ethyl-1',2',3',6-tetrahydro-[3,4'-bipyridin]-6-yl)amino)-2,3-dihydro-1H-inden-4-yl)phenyl)-5-methoxy-1H-pyrazole-4-carboxylic acid or a pharmaceutically acceptable salt thereof may be used alone or in combination with a second therapeutic agent for the treatment of glaucoma. The embodiment further provides methods of treating glaucoma or reducing intraocular pressure in a subject, the method comprising administering one of the specific compounds listed supra alone or in combination with a second therapeutic agent. In certain aspects, the method contemplates topical ocular administration of one of the specific compounds listed supra to the subject in need of such therapy.

In preferred aspects, the method comprises administration of one of these specific compounds as a mono-therapy. In certain other aspects, the method comprises the co-administration (either concomitantly or sequentially) of a compound of Formula I and a PDE-V inhibitor.

Thus, as a further embodiment, the present invention provides the use of a compound of formula (I) or subformulae thereof for the manufacture of a medicament. In preferred embodiments, the invention provides the use of a compound selected from the group consisting of (+)-(R)-1-(3-(3-(4-(1-(cyclopropanecarbonyl)piperidin-4-yl)-3-ethylbenzyl)-2,3-dihydro-1H-inden-4-yl)phenyl)-5-methoxy-1H-pyrazole-4-carboxylic acid, (+)-1-(3-(3-((4-(1-(cyclopropanecarbonyl)piperidin-4-yl)-3-ethylphenyl)amino)-2,3-dihydro-1H-inden-4-yl)phenyl)-5-methoxy-1H-pyrazole-4-carboxylic acid, and (+)-1-(3-(3-((1'-(cyclopropanecarbonyl)-2-ethyl-1',2',3',6-tetrahydro-[3,4'-bipyridin]-6-yl)amino)-2,3-dihydro-1H-inden-4-yl)phenyl)-5-methoxy-1H-pyrazole-4-carboxylic acid in the manufacture of a medicament. In a further aspect, the medicament is for treatment of a disease which may be treated by activation of sGC. In another embodiment, the disease is selected from the afore-mentioned list, suitably glaucoma.

For systemic administration, the administered pharmaceutical composition or combination of the present invention can be in unit dosage of about 0.5-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-10}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

All reactions are carried out under nitrogen or argon unless otherwise stated. Optical rotations were measured in MeOH, using D line of a sodium lamp.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

Multiple parent ion masses are reported for mass spectroscopy data when the compound of the invention contains one or more bromine atoms. Bromine exists as an approximately 1:1 molar ratio of $^{79}$Br:$^{81}$Br. Thus, a compound with a single bromine atom may exhibit two parent mass ions having a difference of 2 amu. The lighter mass ion is reported with the label "(M($^{79}$Br)+H)" and the heavier mass ion is reported with the label "(M($^{81}$Br)+H)" in the Experimental infra. One or both of the mass ions may be reported for each brominated compound infra.

Absolute stereochemistry and/or optical rotations are provided for the embodiments of the invention where applicable. The invention contemplates all stereochemical forms of the compounds provided herein. Where absolute stereochemistry is provided the assessment was made via X-ray diffraction, and/or chemical correlation, and/or at least one chiral center was from a purchased commercial enantiopure (>15:1 enantiomeric ratio) starting material.

In the case of racemic samples, including intermediates, enantiomers are separated by chromatography using a chiral stationary phase and are identified/differentiated either by HPLC/SFC retention time employing a chiral stationary phase and the monikers "enantiomer-1" or "enantiomer-2", and/or by a specific "+" or "−" sign referring to the rotation of polarized light when this data is available.

In the case of diastereomeric samples, including intermediates, diastereomers are separated by chromatography using either a chiral or achiral stationary phase and are identified/differentiated either by HPLC retention time employing a chiral or achiral stationary phase and the monikers "diastereomer-1" or "diastereomer-2".

In some instances examples possess an acidic functional group as such during final purification procedures samples may contain an undetermined mixture of the free acid along with potassium and/or lithium salts of the titled compound. Small changes in the amount of salt present may change the observed chemical shift or intensity for some peaks in the $^1$H NMR spectra.

Abbreviations
Ac acetyl
ACN acetonitrile
AcOH acetic acid
App apparent
aq. aqueous
atm atmosphere
Bis(pinacolato)diboron 4,4,4',4',5,5,5',5'-Octamethyl-2,2'-bi-1,3,2-dioxaborolane
Boc tertiary butyl carboxy
Boc-anhydride di-tert-butyl dicarbonate
(Boc)$_2$O di-tert-butyl dicarbonate
br. broad
BSA bovine serum albumin
BuOH butanol
calcd. calculated
CAN cerium ammonium nitrate
Cs$_2$CO$_3$ cesium carbonate
p-cymene 1-methyl-4-(1-methylethyl)benzene
d doublet
dd doublet of doublets
DCE 1,2-dichloroethane
DCM dichloromethane
DEA diethylamine
DEAD diethyl azodicarboxylate
DIAD diisopropyl azodicarboxylate
DIBAL-H diisobutylaluminium hydride
DIPEA N,N-diisopropylethylamine
DMAP 4,4-dimethylaminopyridine
DME 1,4-dimethoxyethane
DMF N,N-dimethylformamide
Dess-Martin Periodinane Dess-Martin reagent; 1,1,1-Triacetoxy-1,1-dihydro-1,2-benziodoxol-3(1H)-one (CAS #87413-09-0)
DMSO dimethylsulfoxide
EDC.HCl N-(3-Dimethylaminopropyl)-N'-ethylcarbodiimide hydrochloride
ESI electrospray ionization
EtOAc, AcOEt ethyl acetate
Et ethyl
EtOH ethanol
FCC flash column chromatography
g grams
h hour(s)
HATU 2-(1H-7-azabenzotriazol-1-yl)-1,1,3,3-tetramethyl uronium hexafluorophosphate methanaminium
HC HPLC condition
HEPES 4-(2-hydroxyethyl)-1-piperazineethanesulfonic acid
HPLC high performance liquid chromatography
IPA 2-propanol
IR infrared spectroscopy
L liter(s)
LDA lithium diisopropyl amide
M molar
MHz mega Hertz
m multiplet
m-CPBA meta-chloroperoxybenzoic acid
Me methyl
MeCN acetonitrile
MeI iodomethane
MeOH methanol
mg milligram(s)
mM millimolar
mm millimeter(s)
min minutes
mL milliliter(s)
mmol millimoles
MP melting point
MS mass spectrometry
MsCl methanesulfonyl chloride
MsOH methanesulfonic acid
MTBE methyl tert-butylether
m/z mass to charge ratio
N normal
NaBH$_4$ sodium borohydride
NaBH$_3$CN sodium cyanoborohydride
Na(AcO)$_3$BH sodium triacetoxyborohydride
NH$_4$Cl ammonium chloride
NMR nuclear magnetic resonance
PBS phosphate buffered saline
Pd/C palladium on carbon
Pd(dppf)Cl$_2$ 1,1'-bis(diphenylphosphino)ferrocene-palladium(II)dichloride
Pd(dppf)Cl$_2$.CH$_2$Cl$_2$ adduct 1,1'-bis(diphenylphosphino)ferrocene-palladium(II)dichloride dichloromethane complex
Pd(PPh$_3$)$_4$ tetrakis(triphenylphosphine)palladium(0)
Ph phenyl
ppm parts per million PyBOP benzotriazol-1-yloxytripyrrolidinophosphonium hexafluorophosphate
PyBroP® bromotripyrrolidinophosphonium hexafluorophosphate
qs quantum satis/sufficit; as much as suffices
rac racemic
RP reverse phase
rt room temperature
s singlet
sat. saturated
SFC Supercritical Fluid Chromatography
t triplet
$t_r$ retention time
TBAF tetra-n-butylammonium fluoride
TBSCl tert-butyldimethylsilyl chloride
TEA, $Et_3N$ triethylamine
tert-tertiary
Tf trifluoromethanesulfonyl
TFA trifluoroacetic acid
$Tf_2O$ trifluoromethanesulfonic anhydride
THF tetrahydrofuran
TLC Thin Layer Chromatography
TMS trimethylsilyl
TMSOTf trimethylsilyl trifluoromethanesulfonate
Ts p-toluenesulfonyl
Tsdpen N-(2-amino-1,2-diphenylethyl)-4-methylbenzenesulfonamide
TsOH p-toluenesulfonic acid
UPLC ultra performance liquid chromatography
v/v volume per volume
w/v weight per volume
w/w weight per weight Intermediate 1

Intermediate 1-1. Ethyl 1-(3-bromophenyl)-5-hydroxy-1H-pyrazole-4-carboxylate

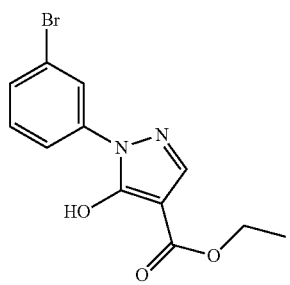 [SMILES: CCOC(=O)c1cnn(-c2cccc(Br)c2)c1O]

A mixture of (3-bromophenyl)hydrazine hydrochloride (8.0 g, 35.8 mmol), diethyl 2-(ethoxymethylene)malonate (CAS #87-13-8; 8.0 mL, 40.0 mmol), and $K_2CO_3$ (10.0 g, 72.4 mmol) in $H_2O$ (120.0 mL) was stirred for 1 h at 100° C. EtOH (40 mL) was added to the reaction mixture and the mixture was stirred for an additional 1 h at 100° C. The reaction mixture was cooled to 0° C. and the pH was adjusted to <2 with 2N aq. HCl. The resulting mixture was stirred for 0.5 h. The resulting solid was collected by filtration and dried under vacuum to afford the title compound without the need for further purification. MS (ESI+) m/z 311.1 (M($^{79}$Br)+H).

Intermediate 1-2. Ethyl 1-(3-bromophenyl)-5-methoxy-1H-pyrazole-4-carboxylate

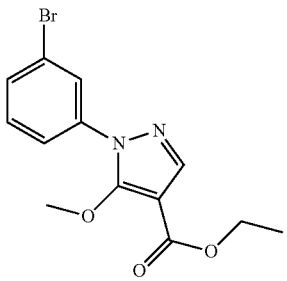 [SMILES: CCOC(=O)c1cnn(-c2cccc(Br)c2)c1OC]

(Trimethylsilyl)diazomethane (2.0M solution in $Et_2O$; 30.0 mL, 60.0 mmol) was added dropwise to a suspension of Intermediate 1-1 (14.0 g, 35.5 mmol) in toluene (300 mL) and MeOH (75.0 mL) at 0° C. over 0.5 h. The mixture was then stirred at 0° C. for 5 h before being quenched with AcOH (30.0 mL, 524.0 mmol). The mixture was stirred for another 0.5 h. The mixture then was diluted with EtOAc, and the organic layer was washed successively with 5% aq. $NaHCO_3$, $H_2O$, and brine. The organic layer was dried over $Na_2SO_4$ and filtered through a plug of silica gel, and the filter cake was rinsed with EtOAc. The filtrate was concentrated and the resulting residue was purified by FCC (0-7% acetone in heptane) to afford the title compound. MS (ESI+) m/z 325.1 (M($^{79}$Br)+H).

Intermediate 1. Ethyl 5-methoxy-1-(3-(4,4,5,5-tetramethyl-1,3,2-dioxaborolan-2-yl)phenyl)-1H-pyrazole-4-carboxylate

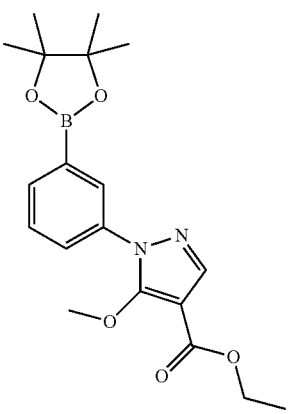 [SMILES: CCOC(=O)c1cnn(-c2cccc(B3OC(C)(C)C(C)(C)O3)c2)c1OC]

Pd(dppf)$Cl_2$·$CH_2Cl_2$ adduct (0.504 g, 0.617 mmol) was added to a suspension of Intermediate 1-2 (2.00 g, 6.17 mmol), bis(pinacolato)diboron (1.723 g, 6.79 mmol), and KOAc (1.212 g, 12.35 mmol) in dioxane (40 mL), and the reaction mixture was stirred at 100° C. for 2 h. The reaction mixture was cooled to rt and Celite® was added. The mixture was concentrated and the residue was purified by FCC (25-30% EtOAc in hexanes) to obtain the title compound. MS (ESI+) m/z 373.2 (M+H).

Intermediate 2

Intermediate 2-1. (5-Bromo-2-methoxyphenyl)hydrazine

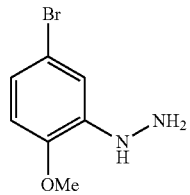 [SMILES: COc1ccc(Br)cc1NN]

A solution of sodium nitrite (1.78 g, 25.87 mmol) in water (5 mL) was slowly added to a cooled (−10° C.) suspension of 5-bromo-2-methoxyaniline (5.0 g, 24.87 mmol) in 6N HCl aq. (13 mL) so as to keep the internal temperature below 0° C. The mixture was stirred for another 20 min at 0° C., then a solution of stannous chloride dihydrate (14.1 g, 72.1 mmol) in conc. aq. HCl (25 mL) was added slowly. The reaction mixture was stirred an additional 1.5 h at 0° C. The pH of the reaction mixture was carefully adjusted to ~8 with sat. aq. NaHCO$_3$. The mixture was extracted with EtOAc and the combined organic layers were dried over Na$_2$SO$_4$, filtered, and concentrated. The resulting residue was purified by trituration with pentane to give the title compound. MS (ESI+) m/z 217.0 (M($^{79}$Br)+H).

Intermediate 2-2. Ethyl 1-(5-bromo-2-methoxyphenyl)-5-hydroxy-1H-pyrazole-4-carboxylate

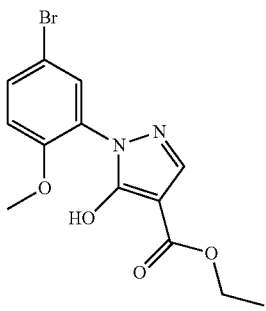 [SMILES: CCOC(=O)c1cnn(-c2cc(Br)ccc2OC)c1O]

The title compound was prepared from Intermediate 2-1 as described in Intermediate 1-1. MS (ESI+) m/z 341.0 (M($^{79}$Br)+H).

Intermediate 2. Ethyl 1-(5-bromo-2-methoxyphenyl)-5-methoxy-1H-pyrazole-4-carboxylate

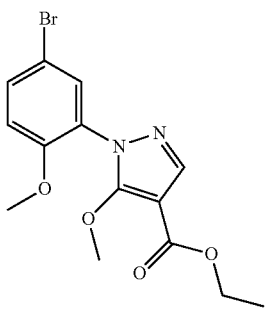 [SMILES: CCOC(=O)c1cnn(-c2cc(Br)ccc2OC)c1OC]

The title compound was prepared from Intermediate 2-2 as described in Intermediate 1-2. MS (ESI+) m/z 357.0 (M($^{81}$Br)+H).

Intermediate 3

Intermediate 3-1. (5-Bromo-2-methylphenyl)hydrazine

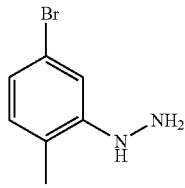

A solution of sodium nitrite (2.04 g, 29.57 mmol) in water (15 mL) was added dropwise to a solution of 5-bromo-2-methylaniline (5.0 g, 26.88 mmol) in conc. aq. HCl (20 mL) at 0° C. The reaction mixture was stirred at 0° C. for 1 h, and then stannous chloride monohydrate (18.19 g, 80.64 mmol) in conc. aq. HCl (20 mL) was added dropwise to the reaction mixture. The reaction mixture was stirred at 0° C. for an additional 1 h. The reaction mixture was slowly made basic with 50% aq. NaOH and the resulting mixture was extracted with EtOAc. The combined organic layers were dried over Na$_2$SO$_4$, filtered, and concentrated to obtain the title compound without the need for further purification. MS (ESI+) m/z 201.1 (M($^{79}$Br)+H).

Intermediate 3-2. Ethyl 1-(5-bromo-2-methylphenyl)-5-hydroxy-1H-pyrazole-4-carboxylate

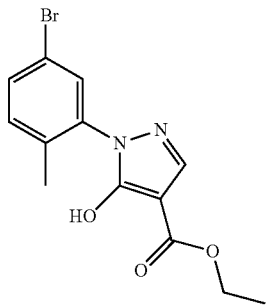 [SMILES: CCOC(=O)c1cnn(-c2cc(Br)ccc2C)c1O]

The title compound was prepared from Intermediate 3-1 as described in Intermediate 1-1. $^1$H NMR (400 MHz, DMSO-d$_6$) δ 11.8 (bs, 1H), 7.81 (bs, 1H), 7.61 (q, 1H, J=8.4, 2.4 Hz), 7.51 (d, 1H, J=2.4 Hz), 7.37 (d, 1H, J=8.4 Hz), 4.22 (q, 2H, J=14.4, 6.8 Hz), 2.04 (s, 3H), 1.27 (t, 3H, J=6.8 Hz).

Intermediate 3. Ethyl 1-(5-bromo-2-methylphenyl)-5-methoxy-1H-pyrazole-4-carboxylate

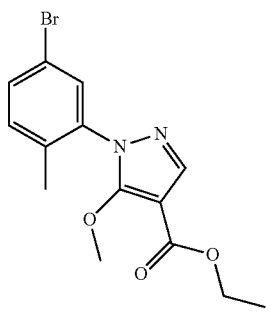 [SMILES: CCOC(=O)c1cnn(-c2cc(Br)ccc2C)c1OC]

The title compound was prepared from Intermediate 3-2 as described in Intermediate 1-2. MS (ESI+) m/z 341.1 (M($^{81}$Br)+H).

Intermediate 4

Intermediate 4-1. Ethyl 5-amino-1-(3-bromophenyl)-1H-pyrazole-4-carboxylate

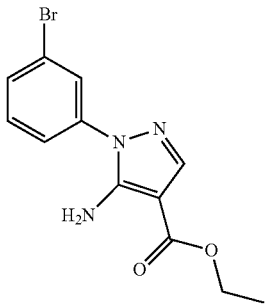 [SMILES: CCOC(=O)c1cnn(-c2cccc(Br)c2)c1N]

A solution of (3-bromophenyl) hydrazine.HCl (5.00 g, 22.37 mmol) in AcOH (75 mL) and water (25 mL) was added to ethyl 2-cyano-3-ethoxyacrylate (CAS #94-05-3; 3.78 g, 22.37 mmol) at rt, and the resulting reaction mixture was stirred at 100° C. for 16 h. The reaction mixture was cooled to rt and made basic with sat. aq. NaHCO$_3$, resulting in the formation of a solid. The solid was collected by filtration and dried under vacuum to obtain the title compound without the need for further purification. MS (ESI+) m/z 310.0 (M($^{79}$Br)+H).

Intermediate 4. Ethyl 1-(3-bromophenyl)-5-(methylamino)-1H-pyrazole-4-carboxylate

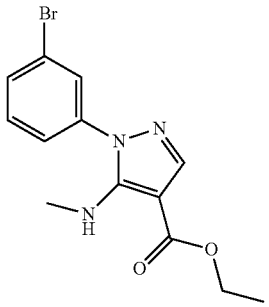 [SMILES: CCOC(=O)c1cnn(-c2cccc(Br)c2)c1NC]

Intermediate 4-1 (500 mg, 1.62 mmol) was added to a suspension of NaH (55% w/w in mineral oil; 63 mg, 1.46 mmol) in DMF (10 mL) at rt, and the reaction mixture was stirred at rt for 30 min. Iodomethane (206 mg, 1.46 mmol) was added to the reaction mixture and the reaction mixture was stirred at rt for 16 h. The reaction mixture was quenched with water and extracted with EtOAc. The combined organic layers were dried over Na$_2$SO$_4$, filtered, and concentrated. The residue was purified by FCC (5% EtOAc in hexanes) to afford the title compound. MS (ESI+) m/z 326.1 (M($^{81}$Br)+H).

Intermediate 5

Intermediate 5-1. tert-Butyl 4-(2-ethyl-4-hydroxyphenyl)-5,6-dihydropyridine-1(2H)-carboxylate

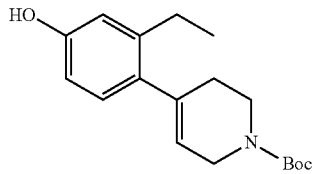 [SMILES: CCc1cc(O)ccc1C1=CCN(C(=O)OC(C)(C)C)CC1]

To a mixture of 4-chloro-3-ethylphenol (3 g, 19.16 mmol), tert-butyl 4-(4,4,5,5-tetramethyl-1,3,2-dioxaborolan-2-yl)-5,6-dihydropyridine-1(2H)-carboxylate (CAS #286961-14-6, 7.70 g, 24.90 mmol), chloro(2-dicyclohexylphosphino-2',6'-dimethoxy-1,1'-biphenyl)[2-(2-aminoethylphenyl)]palladium(II) methyl-t-butylether adduct (CAS #1028206-58-7, 0.644 g, 0.958 mmol) in DMF (96 mL) was added 2M aq. potassium phosphate (28.7 mL, 57.5 mmol). The mixture was stirred at 110° C. for 1 h, and then cooled to rt. The reaction mixture was partitioned between EtOAc and H$_2$O. The organic layer was then separated, and dried over Na$_2$SO$_4$, filtered, and concentrated. The resulting residue was purified by FCC (0-40% EtOAc in heptane) to afford the title compound. MS (ESI+) m/z 248.2 (M-tBu+2H).

Intermediate 5. tert-Butyl 4-(2-ethyl-4-hydroxyphenyl)piperidine-1-carboxylate

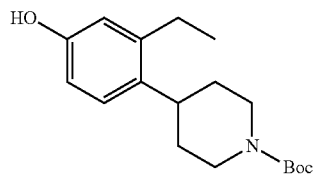 [SMILES: CCc1cc(O)ccc1C1CCN(C(=O)OC(C)(C)C)CC1]

A mixture of Intermediate 5-1 (5.4 g, 17.80 mmol) and 10% Pd/C (1.894 g) in MeOH (250 mL) was stirred under an H$_2$ atmosphere at rt for 1 h. The reaction mixture was then filtered through a plug of Celite®, which was washed with MeOH. The filtrate was concentrated to furnish the title compound without the need for further purification. MS (ESI−) m/z 304.1 (M−H).

Intermediate 6

Intermediate 6-1. tert-Butyl 4-(4-amino-2-ethylphenyl)-5,6-dihydropyridine-1(2H)-carboxylate

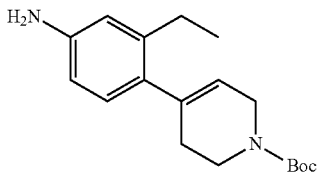 [SMILES: CCc1cc(N)ccc1C1=CCN(C(=O)OC(C)(C)C)CC1]

To a mixture of 4-bromo-3-ethylaniline (5 g, 24.99 mmol), tert-butyl 4-(4,4,5,5-tetramethyl-1,3,2-dioxaborolan-2-yl)-5,6-dihydropyridine-1(2H)-carboxylate (9.66 g, 31.2 mmol), and Pd(dppf)Cl$_2$.CH$_2$Cl$_2$ adduct (1.02 g, 1.25 mmol) in DMF (100 mL) was added 2M aq. potassium phosphate (37.5 mL, 75.0 mmol). The mixture was then stirred at 110° C. for 50 minutes, cooled to room temperature, and diluted with EtOAc. The organic layer was then separated from the aqueous layer, dried over Na$_2$SO$_4$, filtered, and concentrated. The resulting residue was purified by FCC (0-40% EtOAc in heptane) to afford the title compound. MS (ESI+) m/z 303.1 (M+H).

Intermediate 6. tert-Butyl 4-(4-amino-2-ethylphenyl)piperidine-1-carboxylate

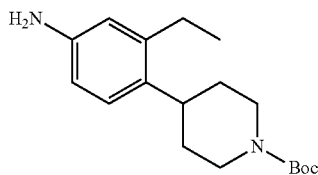 [SMILES: CCc1cc(N)ccc1C1CCN(C(=O)OC(C)(C)C)CC1]

To a solution of Intermediate 6-1 (8.34 g, 27.6 mmol) in MeOH (276 mL) was added 10% Pd/C (2.93 g). The mixture was then stirred under $H_2$ atmosphere for 2 hours. The reaction mixture was filtered through Celite® and the filtrate was concentrated to obtain the title compound without the need for further purification. MS (ESI+) m/z 249.3 (M-tBu+2H).

Intermediate 7

Intermediate 7-1. tert-Butyl 4-(2-ethyl-4-(methoxycarbonyl)phenyl)-5,6-dihydropyridine-1(2H)-carboxylate

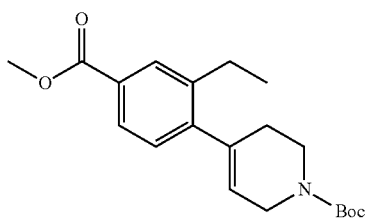 [SMILES: CCc1cc(C(=O)OC)ccc1C1=CCN(C(=O)OC(C)(C)C)CC1]

To a mixture of methyl 4-bromo-3-ethylbenzoate (CAS #1008769-90-1, 1.4 g, 5.76 mmol) and tert-butyl 4-(4,4,5,5-tetramethyl-1,3,2-dioxaborolan-2-yl)-5,6-dihydropyridine-1(2H)-carboxylate (2.32 g, 7.49 mmol) in DMF (20 mL) was added 2.0 M aq. potassium phosphate (8.64 mL, 17.28 mmol), followed by Pd(dppf)Cl$_2$·CH$_2$Cl$_2$ adduct (260 mg, 0.317 mmol). The mixture was stirred at 110° C. for 2 h, and then cooled to room temperature. The reaction mixture was filtered through a plug of Celite®. The filtrate was diluted with EtOAc and the resulting layers separated. The organic layer was washed with H$_2$O, dried over Na$_2$SO$_4$, filtered, and concentrated. The resulting residue was purified by FCC (0-50% EtOAc in heptane) to afford the title compound. $^1$H NMR (400 MHz, Chloroform-d) δ 7.90 (s, 1H) 7.81 (dd, J=7.96, 1.52 Hz, 1H) 7.12 (d, J=7.96 Hz, 1H) 5.57 (br. s., 1H) 4.04 (br. s., 2H) 3.91 (s, 3H) 3.63 (t, J=5.49 Hz, 2H) 2.65 (q, J=7.58 Hz, 2H) 2.34 (br. s., 2H) 1.51 (s, 9H) 1.22 (t, J=7.58 Hz, 3H).

Intermediate 7-2. tert-Butyl 4-(2-ethyl-4-(methoxycarbonyl)phenyl)piperidine-1-carboxylate

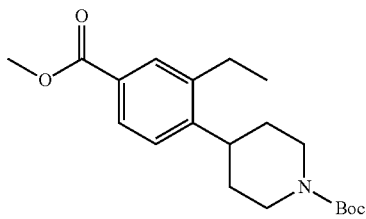 [SMILES: CCc1cc(C(=O)OC)ccc1C1CCN(C(=O)OC(C)(C)C)CC1]

A mixture of Intermediate 7-1 (1.75 g, 5.07 mmol) and 10% Pd/C (175 mg) in EtOH (200 mL) was stirred under H$_2$ atmosphere at rt for 2 h. The reaction mixture was then filtered through a plug of Celite® which was then washed with EtOH. The filtrate was then concentrated to furnish the title compound without the need for further purification. $^1$H NMR (400 MHz, Chloroform-d) δ 7.81-7.88 (m, 2H) 7.23-7.26 (m, 1H) 4.27 (br. s., 2H) 3.90 (s, 3H) 2.88-2.99 (m, 1H) 2.82 (t, J=11.75 Hz, 2H) 2.73 (q, J=7.49 Hz, 2H) 1.59-1.78 (m, 4H) 1.49 (s, 9H) 1.23-1.27 (t, J=8.0 Hz, 3H).

Intermediate 7-3. tert-Butyl 4-(2-ethyl-4-(hydroxymethyl)phenyl)piperidine-1-carboxylate

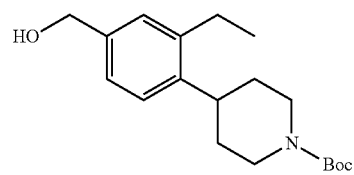 [SMILES: CCc1cc(CO)ccc1C1CCN(C(=O)OC(C)(C)C)CC1]

To a solution of Intermediate 7-2 (1.3 g, 3.74 mmol) in THF (16 mL) was added a solution of 1.0M lithium aluminum hydride in THF (4.5 mL, 4.5 mmol) dropwise. The mixture was then stirred at 0° C. for 1 h. The reaction mixture was quenched with 0.5N aq. NaOH, and then partitioned between H$_2$O and EtOAc. The mixture was then filtered through a plug of Celite®. The organic phase was then separated, washed with brine, dried over Na$_2$SO$_4$, filtered, and concentrated. The residue was purified by FCC (0-50% EtOAc in heptane) to afford the title compound. $^1$H NMR (400 MHz, DMSO-d$_6$) δ 6.98-7.19 (m, 3H) 5.02 (t, J=5.68 Hz, 1H) 4.41 (d, J=5.68 Hz, 2H) 4.07 (d, J=12.00 Hz, 2H) 2.77-2.96 (m, 3H) 2.64 (q, J=7.49 Hz, 2H) 1.58-1.68 (m, 2H) 1.45-1.55 (m, 2H) 1.37-1.44 (m, 9H) 1.15 (t, J=7.52 Hz, 3H).

Intermediate 7. tert-Butyl 4-(2-ethyl-4-formylphenyl)piperidine-1-carboxylate

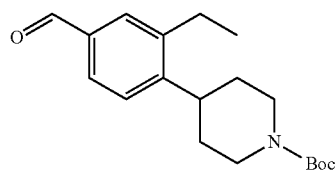 [SMILES: CCc1cc(C=O)ccc1C1CCN(C(=O)OC(C)(C)C)CC1]

Dess-Martin periodinane (6.25 g, 14.74 mmol) was added in one portion to a solution of Intermediate 7-3 (4.28 g, 13.40 mmol) in DCM (67.0 mL) with water (0.24 mL, 13.40 mmol) and the mixture was stirred at rt for 90 min. The reaction mixture was partitioned between water, 1N aq. NaOH, and DCM. The mixture was passed through an Isolute® phase separator and the organic layer was concentrated. The residue was purified by FCC (0-25% EtOAc in heptane) to obtain the title compound. $^1$H NMR (400 MHz, Chloroform-d) δ 9.96 (s, 1H), 7.75-7.63 (m, 2H), 7.36 (d, J=7.9 Hz, 1H), 4.29 (d, J=13.3 Hz, 2H), 3.02-2.90 (m, 1H), 2.89-2.72 (m, 4H), 1.77-1.64 (m, 4H), 1.50 (s, 9H), 1.30-1.24 (m, 3H).

Intermediate 8

Intermediate 8-1. tert-Butyl 2-chloro-3',6'-dihydro-[3,4'-bipyridine]-1'(2'H)-carboxylate

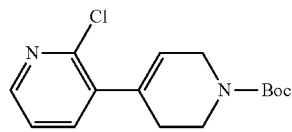 [SMILES: CC(C)(C)OC(=O)N1CC=C(c2cccnc2Cl)CC1]

Pd(dppf)Cl$_2$.CH$_2$Cl$_2$ adduct (849 mg, 1.04 mmol) was added to a solution of 3-bromo-2-chloropyridine (4.0 g, 20.8 mmol) and tert-butyl 4-(4,4,5,5-tetramethyl-1,3,2-dioxaborolan-2-yl)-5,6-dihydropyridine-1(2H)-carboxylate (6.43 g, 20.8 mmol) and Na$_2$CO$_3$ (4.41 g, 41.6 mmol) in dioxane (150 mL) and water (30 mL). The mixture was stirred at 110° C. under a nitrogen atmosphere for 6 h. The mixture was cooled to rt and filtered through Celite®. The organic layer of the filtrate was isolated and concentrated. The resulting residue was purified by FCC (0-50% EtOAc in heptane) to afford the title compound. MS (ESI+) m/z 295.3 (M+H).

Intermediate 8-2. tert-Butyl 2-ethyl-3',6'-dihydro-[3,4'-bipyridine]-1'(2'H)-carboxylate

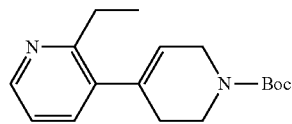 [SMILES: CCc1ncccc1C1=CCN(C(=O)OC(C)(C)C)CC1]

Pd(dppf)Cl$_2$.CH$_2$Cl$_2$ adduct (1.17 g, 1.43 mmol) was added to a solution of Intermediate 8-1 (6.25 g, 19.1 mmol) and K$_2$CO$_3$ (7.91 g, 57.2 mmol) in THF (200 mL). The mixture was degassed via sparging with N$_2$ gas for 1 min, and then diethylzinc (15% w/w in toluene, 51.5 mL, 57.2 mmol) was added. The mixture was stirred at rt for 1 h, and then heated to 50° C. for a further 3 h. The reaction mixture was cooled to 0° C., and then quenched with sat. aq. NH$_4$Cl and water. The mixture was filtered through Celite® and the filtrate was extracted with EtOAc. The combined organic layers were dried over Na$_2$SO$_4$, filtered, and concentrated. The residue was purified by FCC (0-50% EtOAc in heptane) to afford the title compound. MS (ESI+) m/z 289.1 (M+H).

Intermediate 8. 1'-(tert-Butoxycarbonyl)-2-ethyl-1',2',3',6'-tetrahydro-[3,4'-bipyridine] 1-oxide

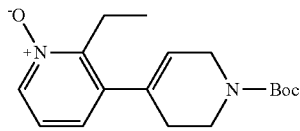

m-CPBA (3400 mg, 15.16 mmol) was added in portions to a solution of Intermediate 8-2 (3700 mg, 14.43 mmol) in chloroform (100 mL) at 0° C. over the course of 10 min. The reaction mixture was stirred at 0° C. for 2 h. The reaction mixture was quenched with a sat. aq. Na$_2$S$_2$O$_3$, and the mixture was extracted with chloroform. The combined organic layers were washed successively with sat. aq. NaHCO$_3$ and brine. The organic layer was dried over Na$_2$SO$_4$, filtered, and concentrated to give the title compound without the need for further purification. MS (ESI+) m/z 305.1 (M+H).

Intermediate 9. 7-Bromo-2,3-dihydro-1H-inden-1-amine hydrochloride

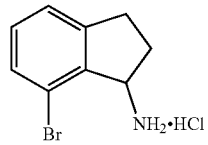

NaBH$_3$CN (145 mg, 2.31 mmol) was added to a solution of 7-bromo-2,3-dihydro-1H-inden-1-one (CAS #125114-77-4; 406 mg, 1.92 mmol) and NH$_4$OAc (2224 mg, 28.9 mmol) in EtOH (4.8 mL). The mixture was heated to 130° C. for 2 min under the microwave irradiation. The reaction mixture was cooled to rt, poured into 50 mL 1N aq. NaOH and the mixture was extracted with EtOAc. The combined organic layers were washed with brine, dried over Na$_2$SO$_4$, filtered, and concentrated. The residue was slurried in diethyl ether and to that mixture was added HCl (1M in diethyl ether; 2.9 mL, 2.89 mmol). The resulting white solids were collected by filtration and dried under vacuum to obtain the title compound without the need for further purification. $^1$H NMR (400 MHz, Methanol-d$_4$) δ 7.51-7.47 (m, 1H), 7.39-7.35 (m, 1H), 7.32 (t, J=7.6 Hz, 1H), 4.89-4.85 (m, 1H), 3.36-3.31 (m, 1H), 3.14-3.04 (m, 1H), 2.65-2.54 (m, 1H), 2.25-2.17 (m, 1H).

Intermediate 10. (−)-(R)-7-Bromo-2,3-dihydro-1H-inden-1-ol

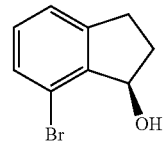 [SMILES: O[C@@H]1CCc2cccc(Br)c21]

Triethylamine (1.45 mL, 10.42 mmol) was added dropwise to formic acid (1.018 mL, 26.5 mmol) at rt. The temperature of the reaction mixture was maintained under 45° C. by controlling the rate of the addition. After the addition was completed, the reaction mixture was cooled to 0° C. in an ice bath and stirred for 30 min. The mixture was then warmed to room temperature and stirred for 1 h. To this solution was added DMF (7 mL) followed by 7-bromo-2,3-dihydro-1H-inden-1-one (4 g, 18.95 mmol) and RuCl[(R,R)-Tsdpen](p-cymene) (CAS #192139-92-7; 0.013 g, 0.021 mmol). The reaction mixture was stirred at room temperature for 40 h before being heated to 60° C. for a further 24 h. The reaction mixture was cooled to rt and partitioned between EtOAc and half sat. brine. The layers were separated and the aqueous layer was extracted with EtOAc. The combined organic layers were concentrated. The residue was absorbed onto silica and purified by FCC (100% DCM) to provide (−)-(R)-7-bromo-2,3-dihydro-1H-inden-1-ol (>98% e.e.). $^1$H NMR (400 MHz, Chloroform-d) δ 7.41-7.33 (m, 1H), 7.25-7.20 (m, 1H), 7.15 (t, J=7.6 Hz, 1H), 5.41-5.34 (m, 1H), 3.30-3.17 (m, 1H), 2.97-2.84 (m, 1H), 2.51-2.35 (m, 1H), 2.20-2.09 (m, 1H). Absolute stereochemistry of (−)-R-7-bromo-2,3-dihydro-1H-inden-1-ol was confirmed by X-ray single crystal diffraction.

Enantiomeric excess of 7-bromo-2,3-dihydro-1H-inden-1-ol was determined by chiral SFC using CHIRALPAK® OD-H, 10% IPA in $CO_2$; (−)-(R)-7-bromo-2,3-dihydro-1H-inden-1-ol ($t_r$=4.87 min) and (+)-(S)-7-bromo-2,3-dihydro-1H-inden-1-ol ($t_r$=5.58 min).

Intermediate 11

Intermediate 11-1. (7-Methoxy-2,3-dihydro-1H-inden-1-yl)triphenylphosphonium bromide

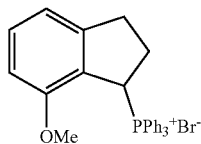

A mixture of 7-methoxyindan-1-ol (CAS #34985-44-9; 0.86 g, 5.23 mmol) and triphenylphosphine hydrobromide (1.85 g, 5.23 mmol) in toluene (10.5 mL) was stirred at 90° C. for 16 h, and then cooled to room temperature. The solvent from the resulting heterogeneous mixture was decanted, and then diethyl ether was added to the residue, which was then stirred for 0.5 h at room temperature. The resulting solid was collected by filtration, and then washed with diethyl ether to furnish the title compound without the need for further purification. MS (ESI+) m/z 409.3 (M+).

Intermediate 11-2. tert-Butyl-4-(2-ethyl-4-((7-methoxy-2,3-dihydro-1H-inden-1-ylidene)methyl)phenyl)piperidine-1-carboxylate

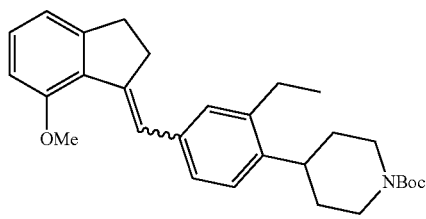 [SMILES: CCc1cc(C=C2CCc3cccc(OC)c32)ccc1C1CCN(C(=O)OC(C)(C)C)CC1]

Potassium tert-butoxide (1M in THF; 4.7 mL, 4.7 mmol) was added dropwise to a solution of Intermediate 11-1 (2.08 g, 4.25 mmol) in EtOH (20.5 mL) at rt. The reaction mixture was stirred for 30 min before Intermediate 7 (1.35 g, 4.25 mmol) in THF (20.5 mL) was added dropwise and the reaction mixture was heated to 68° C. for 17 hours. The reaction mixture was then partitioned between DCM, water, and sat. aq. $NH_4Cl$, then passed through an Isolute® phase separator. The organic layer was concentrated and the residue was purified by FCC (0-40% EtOAc in heptane) to obtain the title compound. MS (ESI+) m/z 392.2 (M-tBu+2H).

Intermediate 11-3. tert-Butyl 4-(2-ethyl-4-((7-methoxy-2,3-dihydro-1H-inden-1-yl)methyl)phenyl)piperidine-1-carboxylate

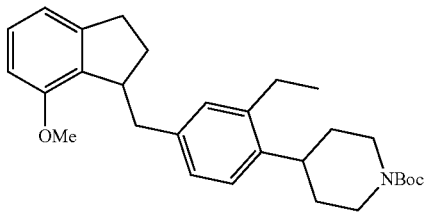 [SMILES: CCc1cc(CC2CCc3cccc(OC)c32)ccc1C1CCN(C(=O)OC(C)(C)C)CC1]

10% Pd/C (0.172 g) was added to a solution of Intermediate 11-2 (1.45 g, 3.24 mmol) in EtOH (27.0 mL) and EtOAc (5.40 mL) and the heterogeneous reaction mixture was stirred for 3 h under $H_2$ atmosphere. Celite® and sat. aq. $NH_4Cl$ (0.05 mL) were added to the reaction mixture. The mixture was filtered through a pad of Celite®. The filtrate was concentrated to yield the title compound without the need for further purification. MS (ESI+) m/z 394.3 (M-tBu+2H).

Intermediate 11-4. 3-(3-Ethyl-4-(piperidin-4-yl)benzyl)-2,3-dihydro-1H-inden-4-ol

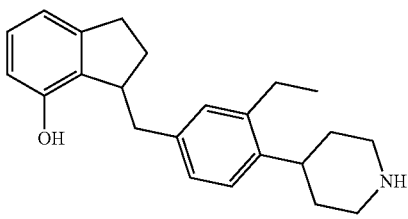 [SMILES: CCc1cc(CC2CCc3cccc(O)c32)ccc1C1CCNCC1]

Boron tribromide (1 M in DCM; 9.67 mL, 9.67 mmol) was added dropwise to a solution of Intermediate 11-3 (1.45 g, 3.22 mmol) in DCM (32 mL) at −78° C. The mixture was stirred at 0° C. for 60 min before the mixture was partitioned between sat. aq. $NaHCO_3$ and DCM. The organic layer was washed with water and brine, and then was passed through an Isolute® phase separator. The filtrate was concentrated to provide the title compound without the need for further purification. MS (ESI+) m/z 336.3 (M+H).

Intermediate 11-5. tert-Butyl 4-(2-ethyl-4-((7-hydroxy-2,3-dihydro-1H-inden-1-yl)methyl)phenyl)piperidine-1-carboxylate

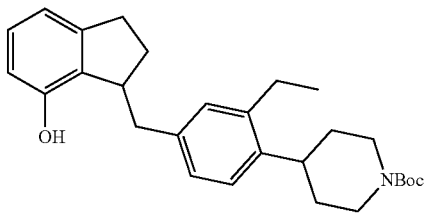 [SMILES: CCc1cc(CC2CCc3cccc(O)c32)ccc1C1CCN(C(=O)OC(C)(C)C)CC1]

Triethylamine (0.71 mL, 5.10 mmol) was added dropwise to a solution of Intermediate 11-4 (1.14 g, 3.40 mmol) and Boc-anhydride (0.89 g, 4.08 mmol) in THF (17 mL) at 0° C. The reaction mixture was stirred at 0° C. for 30 min. The mixture was quenched with water, followed by sat. aq. NaHCO₃. The mixture was extracted with EtOAc, and the combined organic layers were washed sequentially with 5% aq. NaHCO₃ and brine. The organic layer was then passed through an Isolute® phase separator and concentrated. The residue was purified by FCC (0-20% EtOAc/heptane) to obtain the title compound. MS (ESI+) m/z 380.2 (M-tBu+ 2H).

Intermediate 11-6. tert-Butyl (R)-4-(2-ethyl-4-((7-hydroxy-2,3-dihydro-1H-inden-1-yl)methyl)phenyl) piperidine-1-carboxylate and tert-butyl (S)-4-(2-ethyl-4-((7-hydroxy-2,3-dihydro-1H-inden-1-yl) methyl)phenyl)piperidine-1-carboxylate Resolution of the enantiomers of tert-butyl 4-(2-ethyl-4-((7-hydroxy-2,3-dihydro-1H-inden-1-yl)methyl)phenyl)piperidine-1-carboxylate was achieved by chiral HPLC using CHIRALPAK® IA column with isocratic 85:15 (0.1% DEA in n-hexane):(IPA:DCM [90:10]) to give tert-butyl (S)-4-(2-ethyl-4-((7-hydroxy-2,3-dihydro-1H-inden-1-yl)methyl) phenyl)piperidine-1-carboxylate (t$_r$=4.60 min) and tert-butyl (R)-4-(2-ethyl-4-((7-hydroxy-2,3-dihydro-1H-inden-1-yl)methyl)phenyl)piperidine-1-carboxylate (t$_r$=6.69 min).

The absolute stereochemistry of Intermediate 11-6 was determined based on non-epimerization of the indane stereocenter in the synthetic steps between separation of Intermediate 11-6 and Example 1A. The absolute stereochemistry of Example 1A was determined via X-ray single crystal diffraction.

Intermediate 11A. tert-Butyl (R)-4-(2-ethyl-4-((7-(((trifluoromethyl)sulfonyl)oxy)-2,3-dihydro-1H-inden-1-yl)methyl)phenyl)piperidine-1-carboxylate

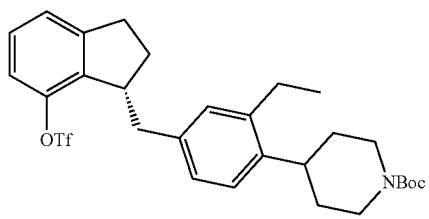 [SMILES: CCc1cc(C[C@H]2CCc3cccc(OS(=O)(=O)C(F)(F)F)c32)ccc1C1CCN(C(=O)OC(C)(C)C)CC1]

Trifluoromethanesulfonic anhydride (0.52 mL, 3.09 mmol) was added dropwise to a solution of tert-butyl (R)-4-(2-ethyl-4-((7-hydroxy-2,3-dihydro-1H-inden-1-yl)methyl)phenyl)piperidine-1-carboxylate (Intermediate 11-6, t$_r$=6.69 min; 0.96 g, 2.204 mmol) and pyridine (0.535 mL, 6.61 mmol) in DCM (15 mL) at 0° C. and the reaction mixture was stirred for 15 min. The reaction mixture was partitioned between 1N aq. HCl and DCM, and the organic layer was washed with sat. aq. NaHCO₃. The organic layer was then filtered through an Isolute® phase separator and concentrated to provide the title compound without the need for further purification. MS (ESI+) m/z 568.4 (M+H).

Intermediate 11B. tert-Butyl (S)-4-(2-ethyl-4-((7-(((trifluoromethyl)sulfonyl)oxy)-2,3-dihydro-1H-inden-1-yl)methyl)phenyl)piperidine-1-carboxylate

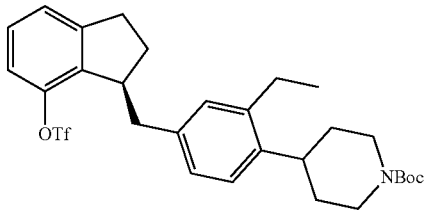 [SMILES: CCc1cc(C[C@@H]2CCc3cccc(OS(=O)(=O)C(F)(F)F)c32)ccc1C1CCN(C(=O)OC(C)(C)C)CC1]

tert-Butyl (S)-4-(2-ethyl-4-((7-hydroxy-2,3-dihydro-1H-inden-1-yl)methyl)phenyl)piperidine-1-carboxylate (Intermediate 11-6; t$_r$=4.60 min) was treated under the reaction conditions described for the preparation of Intermediate 11A to afford the title compound. MS data was substantially identical to Intermediate 11A.

Intermediate 12

Intermediate 12-1. tert-Butyl 4-(4-((7-bromo-2,3-dihydro-1H-inden-1-yl)amino)-2-ethylphenyl)piperidine-1-carboxylate

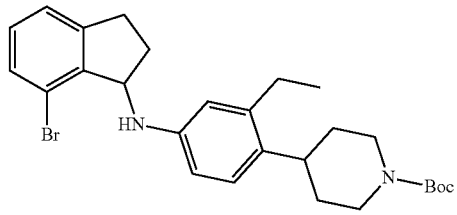 [SMILES: CCc1cc(NC2CCc3cccc(Br)c32)ccc1C1CCN(C(=O)OC(C)(C)C)CC1]

A flask fitted with a Dean-Stark trap, containing a solution of 7-bromo-2,3-dihydro-1H-inden-1-one (3.0 g, 14.29 mmol), Intermediate 6 (4.78 g, 15.72 mmol), and p-TsOH.H₂O (0.36 g, 1.85 mmol) in toluene (150 mL) and DMA (40 mL) was stirred at reflux for 24 h to facilitate azeotropic removal of water. The reaction mixture was then cooled to 0° C. and AcOH (3 mL) was added, followed by NaBH₃CN (2.20 g, 35.72 mmol). The reaction mixture was warmed to rt for 3 h, before cooling back to 0° C. The mixture was made basic by addition of sat. aq. NaHCO₃. The mixture was then extracted with EtOAc, and the combined organic layers were dried over Na₂SO₄, filtered, and concentrated. The residue was purified by FCC (10% EtOAc in hexanes) to obtain the title compound. MS (ESI+) m/z 501.2 (M($^{81}$Br)+H).

Intermediate 12-2. 7-Bromo-N-(3-ethyl-4-(piperidin-4-yl)phenyl)-2,3-dihydro-1H-inden-1-amine

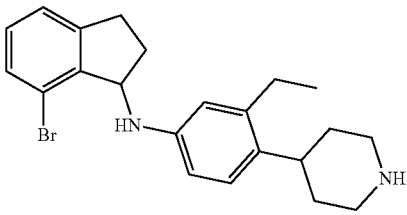 [SMILES: CCc1cc(NC2CCc3cccc(Br)c32)ccc1C1CCNCC1]

Trifluoroacetic acid (1.54 mL, 20.06 mmol) was added dropwise to a solution of Intermediate 12-1 (500 mg, 1.00 mmol) in DCM (10 mL) at rt, and the reaction mixture was stirred for 1.5 h. The reaction mixture was concentrated and the residue was partitioned between sat. aq. NaHCO$_3$ and EtOAc. The organic layer was isolated, dried over Na$_2$SO$_4$, filtered, and concentrated to obtain the title compound without the need for further purification. MS (ESI+) m/z 399.1 (M($^{79}$Br)+H).

Intermediate 12. (4-(4-((7-Bromo-2,3-dihydro-1H-inden-1-yl)amino)-2-ethylphenyl)piperidin-1-yl)(cyclopropyl)methanone

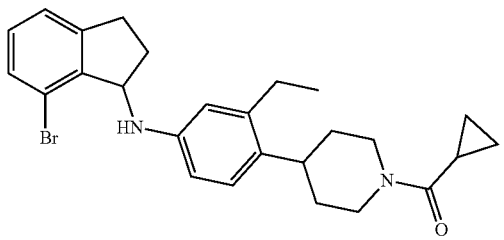 [SMILES: CCc1cc(NC2CCc3cccc(Br)c32)ccc1C1CCN(C(=O)C2CC2)CC1]

DIPEA (0.54 mL, 3.00 mmol) was added to a solution of Intermediate 12-2 (399 mg, 1.00 mmol) in DMF (10 mL) at rt and the mixture was stirred for 10 min. Cyclopropanecarboxylic acid (86 mg, 1.00 mmol) was added, followed by HATU (571 mg, 1.5 mmol), and the mixture was stirred at rt for 16 h. The reaction mixture was diluted with water, and the resulting solid was collected by filtration. The solid was dried under vacuum to obtain the title compound without the need for further purification. MS (ESI+) m/z 467.2 (M($^{79}$Br)+H).

Intermediate 13

Intermediate 13-1. tert-Butyl (S)-4-(4-((7-bromo-2,3-dihydro-1H-inden-1-yl)oxy)-2-ethylphenyl)piperidine-1-carboxylate

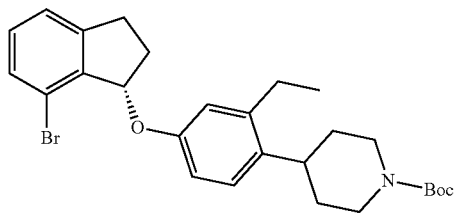 [SMILES: CCc1cc(O[C@H]2CCc3cccc(Br)c32)ccc1C1CCN(C(=O)OC(C)(C)C)CC1]

Tri-n-butylphosphine (1.05 mL, 4.25 mmol) was added to a solution of (−)-(R)-7-bromo-2,3-dihydro-1H-inden-1-ol (Intermediate 10; 300 mg, 1.42 mmol) and Intermediate 5 (453 mg, 1.49 mmol) in THF (15 mL) at 0° C., followed by dropwise addition of DIAD (0.83 mL, 4.25 mmol). The reaction mixture was stirred at 0° C. for 2 h before being concentrated under reduced pressure. The resulting residue was purified by FCC (5% EtOAc in hexanes) to obtain the title compound. MS (ESI+) m/z 400.1 (M($^{79}$Br)-Boc+2H).

Intermediate 13-2. (S)-4-(4-((7-Bromo-2,3-dihydro-1H-inden-1-yl)oxy)-2-ethylphenyl)piperidine

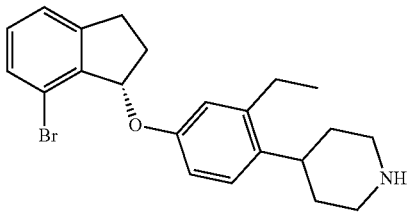 [SMILES: CCc1cc(O[C@H]2CCc3cccc(Br)c32)ccc1C1CCNCC1]

TMSOTf (0.69 g, 3.09 mmol) was added to a solution of tert-butyl (S)-4-(4-((7-bromo-2,3-dihydro-1H-inden-1-yl)oxy)-2-ethylphenyl)piperidine-1-carboxylate (Intermediate 13-1; 770 mg, 1.54 mmol) and DIPEA (1.6 mL, 9.25 mmol) in DCM (15 mL) at 0° C. The reaction mixture was stirred at 0° C. for 2 h before being quenched with MeOH (0.5 mL). The mixture was concentrated under reduced pressure to obtain the title compound without the need for further purification. MS (ESI+) m/z 402.1 (M($^{81}$Br)+H).

Intermediate 13. (S)-(4-(4-((7-Bromo-2,3-dihydro-1H-inden-1-yl)oxy)-2-ethylphenyl)piperidin-1-yl)(cyclopropyl)methanone

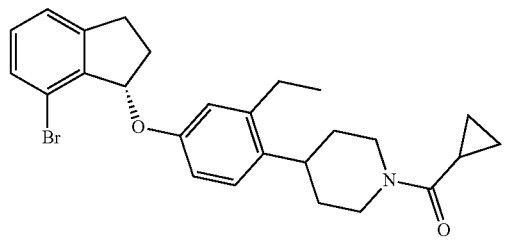 [SMILES: CCc1cc(O[C@H]2CCc3cccc(Br)c32)ccc1C1CCN(C(=O)C2CC2)CC1]

EDC.HCl (504 mg, 2.63 mmol) and DIPEA (1.2 mL, 7.01 mmol) were added to a mixture of (S)-4-(4-((7-Bromo-2,3-dihydro-1H-inden-1-yl)oxy)-2-ethylphenyl)piperidine (Intermediate 13-2; 700 mg, 1.75 mmol) and cyclopropanecarboxylic acid (166 mg, 1.93 mmol) in DCM (15 mL) at rt, followed by HOBt (402 mg, 2.63 mmol). The reaction mixture was stirred at rt for 16 h, then partitioned between water and DCM. The organic layer was dried over Na$_2$SO$_4$, filtered, and concentrated. The resulting residue was purified by FCC (30% EtOAc in hexanes) to obtain the title compound. MS (ESI+) m/z 470.2 (M($^{81}$Br)+H).

Intermediate 14. tert-Butyl 6-((7-bromo-2,3-dihydro-1H-inden-1-yl)amino)-2-ethyl-3',6'-dihydro-[3,4'-bipyridine]-1'(2'H)-carboxylate

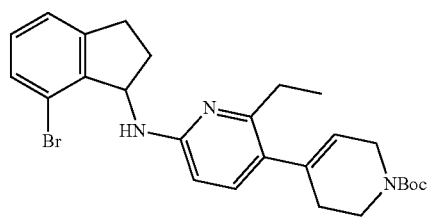 [SMILES: CCc1nc(NC2CCc3cccc(Br)c32)ccc1C1=CCN(C(=O)OC(C)(C)C)CC1]

PyBroP® (CAS #132705-51-2; 14.72 g, 31.58 mmol) was added to a solution of Intermediate 9 (6.00 g, 24.29 mmol), Intermediate 8 (4.064 g, 13.36 mmol), and DIPEA (21.2 mL, 121.5 mmol) in DCM (200 mL). The mixture was stirred at 45° C. for 84 h, and then diluted with DCM. The organic layer was washed successively with 1N aq. citric acid, sat. aq. NaHCO$_3$, and brine. The organic layer was dried with Na$_2$SO$_4$, filtered, and concentrated. The residue was purified by FCC (4-10% EtOAc in heptane) to give the title compound. MS (ESI+) m/z 498.2 (M($^{79}$Br)+H).

Intermediate 15

Intermediate 15-1. tert-Butyl (R)-4-(4-((7-(3-(4-(ethoxycarbonyl)-5-methoxy-1H-pyrazol-1-yl)phenyl)-2,3-dihydro-1H-inden-1-yl)methyl)-2-ethylphenyl)piperidine-1-carboxylate

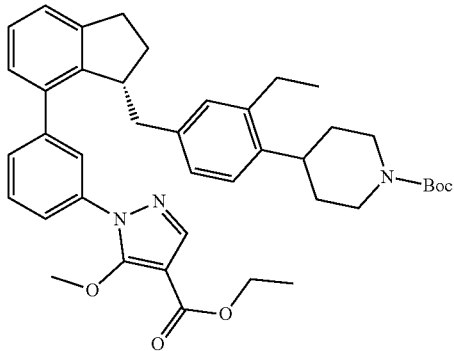 [SMILES: CCOC(=O)c1cnn(-c2cccc(-c3cccc4c3[C@@H](Cc3ccc(C5CCN(C(=O)OC(C)(C)C)CC5)c(CC)c3)CC4)c2)c1OC]

A solution of tert-butyl (R)-4-(2-ethyl-4-((7-(((trifluoromethyl)sulfonyl)oxy)-2,3-dihydro-1H-inden-1-yl)methyl)phenyl)piperidine-1-carboxylate (Intermediate 11A, 600 mg, 1.06 mmol), Intermediate 1 (433 mg, 1.16 mmol), and Na$_2$CO$_3$ (224 mg, 2.12 mmol) in dioxane (20 mL) and water (5 mL) was degassed by sparging with N$_2$ gas for 5 min. Pd(PPh$_3$)$_4$ was then added and the mixture was heated to 100° C. for 3 h. After cooling to rt, the reaction mixture was diluted with water and extracted with EtOAc. The combined organic layers were washed with brine, dried over Na$_2$SO$_4$, filtered, and concentrated. The residue was purified by FCC (20-25% EtOAc in hexanes) to obtain the title compound. MS (ESI+) m/z 664.4 (M+H).

Intermediate 15A. Ethyl (R)-1-(3-(3-(3-ethyl-4-(piperidin-4-yl)benzyl)-2,3-dihydro-1H-inden-4-yl)phenyl)-5-methoxy-1H-pyrazole-4-carboxylate

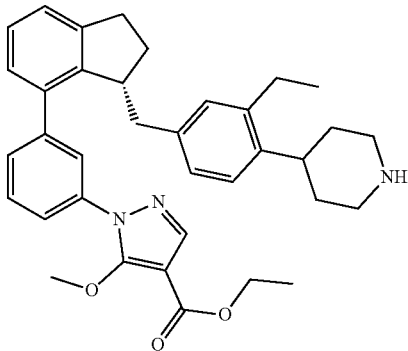

TFA (0.35 mL, 4.52 mmol) was added to a solution of Intermediate 15-1 (150 mg, 0.23 mmol) in DCM at rt, and the reaction mixture was stirred at rt for 3 h. The reaction mixture was concentrated under reduced pressure to obtain the title compound without the need for further purification. MS (ESI+) m/z 564.3 (M+H).

Intermediate 15B. Ethyl (S)-1-(3-(3-(3-ethyl-4-(piperidin-4-yl)benzyl)-2,3-dihydro-1H-inden-4-yl)phenyl)-5-methoxy-1H-pyrazole-4-carboxylate

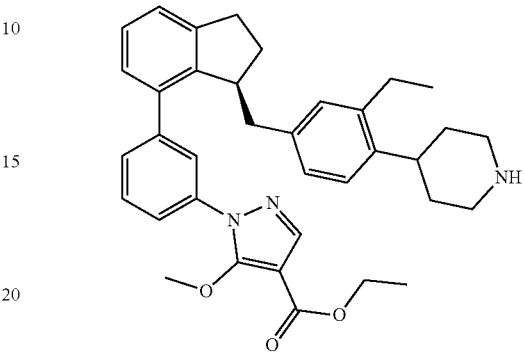

The title compound was prepared starting from tert-butyl (S)-4-(2-ethyl-4-((7-(((trifluoromethyl)sulfonyl)oxy)-2,3-dihydro-1H-inden-1-yl)methyl)phenyl)piperidine-1-carboxylate (Intermediate 11B) and Intermediate 1 as described to make Intermediate 15A. The analytical data are substantially identical to that of Intermediate 15A.

Intermediate 16

Intermediate 16-1. tert-Butyl 4-(4-((7-(3-(4-(ethoxycarbonyl)-5-methoxy-1H-pyrazol-1-yl)phenyl)-2,3-dihydro-1H-inden-1-yl)amino)-2-ethylphenyl)piperidine-1-carboxylate

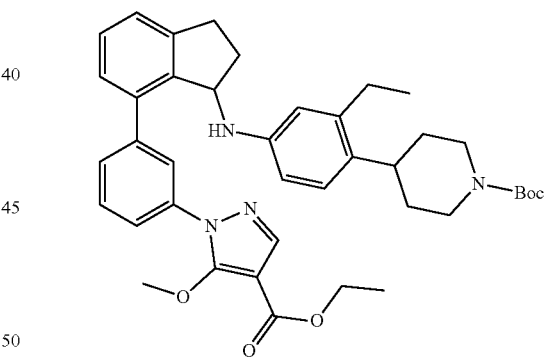

Pd(dppf)Cl$_2$.CH$_2$Cl$_2$ adduct (0.196 g, 0.24 mmol) was added to a mixture of Intermediate 1-2 (1.32 g, 4.01 mmol), bis(pinacolato)diboron (1.12 g, 4.41 mmol), and KOAc (0.591 g, 6.02 mmol) in dioxane (30 mL) and the reaction mixture was heated to 100° C. for 2 h. The reaction mixture was cooled to rt and Intermediate 12-1 (1.00 g, 2.01 mmol) was added, followed by 2M aq. K$_3$PO$_4$ (6.0 mL, 12.03 mmol) and Pd(dppf)Cl$_2$.CH$_2$Cl$_2$ adduct (0.327 g, 0.40 mmol). The reaction mixture was then heated to 100° C. for another 2 h. The reaction mixture was cooled to rt and concentrated under reduced pressure. The residue was partitioned between EtOAc and water. The isolated organic layer was then dried over Na$_2$SO$_4$, filtered, and concentrated. The residue was purified by FCC (20% EtOAc in hexanes) to obtain the title compound. MS (ESI+) m/z 665.4 (M+H).

Intermediate 16. Ethyl 1-(3-(3-((3-ethyl-4-(piperidin-4-yl)phenyl)amino)-2,3-dihydro-1H-inden-4-yl)phenyl)-5-methoxy-1H-pyrazole-4-carboxylate

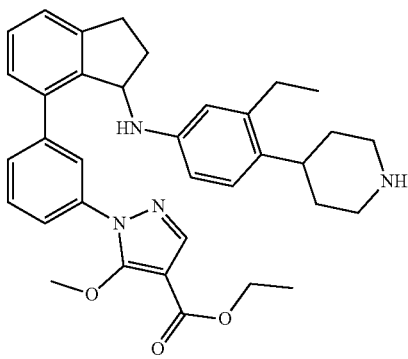 [SMILES: CCOC(=O)c1cnn(-c2cccc(-c3cccc4c3C(Nc3ccc(C5CCNCC5)c(CC)c3)CC4)c2)c1OC]

TFA (2.0 mL, 26.52 mmol) was added dropwise to a solution of Intermediate 16-1 (920 mg, 1.33 mmol) in DCM (20 mL) at rt and the reaction mixture was stirred at rt for 1.5 h. The reaction mixture was concentrated and the residue was partitioned between sat. aq. $NaHCO_3$ and EtOAc. The aqueous layer was extracted with EtOAc and the combined organic layers were dried over $Na_2SO_4$, filtered, and concentrated to obtain the title compound without the need for further purification. MS (ESI+) m/z 565.4 (M+H).

Intermediate 17

The following compounds were synthesized using similar methods to those described to make Intermediate 16, using the indicated starting materials.

| Intermediate | Structure/Chemical Name | Starting material(s) | MS Data |
|---|---|---|---|
| 17-1 | Ethyl 1-(5-(3-((3-ethyl-4-(piperidin-4-yl)phenyl)amino)-2,3-dihydro-1H-inden-4-yl)-2-methylphenyl)-5-methoxy-1H-pyrazole-4-carboxylate | Intermediate 3 and Intermediate 12-1 | MS (ESI+) m/z 579.4 (M + H). |
| 17-2 | Ethyl 1-(5-(3-((3-ethyl-4-(piperidin-4-yl)phenyl)amino)-2,3-dihydro-1H-inden-4-yl)-2-methoxyphenyl)-5-methoxy-1H-pyrazole-4-carboxylate | Intermediate 2 and Intermediate 12-1 | MS (ESI+) m/z 595.4 (M + H). |

Intermediate 18

Intermediate 18-1. tert-Butyl 6-((7-(3-(4-(ethoxycarbonyl)-5-methoxy-1H-pyrazol-1-yl)phenyl)-2,3-dihydro-1H-inden-1-yl)amino)-2-ethyl-3',6'-dihydro-[3,4'-bipyridine]-1'(2'H)-carboxylate

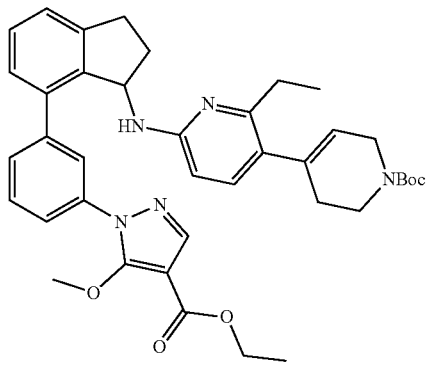 [SMILES: CCOC(=O)c1cnn(-c2cccc(-c3cccc4c3C(Nc3ccc(C5=CCN(C(=O)OC(C)(C)C)CC5)c(CC)n3)CC4)c2)c1OC]

A mixture of Intermediate 1 (538 mg, 1.45 mmol), Intermediate 14 (600 mg, 1.21 mmol), and $Na_2CO_3$ (256 mg, 2.41 mmol) in dioxane (30 mL) and water (5 mL) was degassed by sparging with $N_2$ gas for 5 min. $Pd(PPh_3)_4$ (139 mg, 0.12 mmol) was added to this mixture, and the reaction mixture was heated to 90° C. for 6 h. The reaction mixture was cooled to rt, diluted with water, and then extracted with EtOAc. The combined organic layers were washed with brine, dried over $Na_2SO_4$, filtered, and concentrated. The residue was purified by FCC (10% EtOAc in hexanes) to obtain the title compound. MS (ESI+) m/z 664.4 (M+H).

Intermediate 18. Ethyl 1-(3-(3-((2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylate

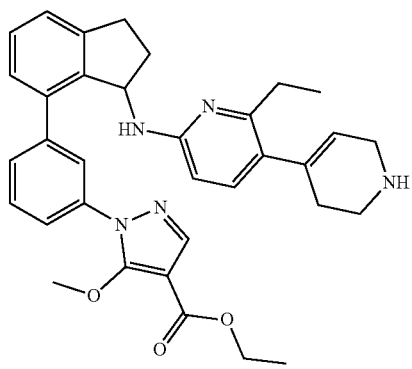 [SMILES: CCOC(=O)c1cnn(-c2cccc(-c3cccc4c3C(Nc3ccc(C5=CCNCC5)c(CC)n3)CC4)c2)c1OC]

TFA (0.83 mL, 10.85 mmol) was added to a solution of Intermediate 18-1 (360 mg, 0.54 mmol) in DCM (20 mL) and the mixture was stirred at rt for 3 h. The reaction mixture was concentrated under reduced pressure to obtain the title compound without the need for further purification MS (ESI+) m/z 564.3 (M+H).

Intermediate 19

Intermediate 19-1. tert-Butyl (S)-4-(4-((7-(3-(4-(ethoxycarbonyl)-5-methoxy-1H-pyrazol-1-yl)phenyl)-2,3-dihydro-1H-inden-1-yl)oxy)-2-ethylphenyl)piperidine-1-carboxylate

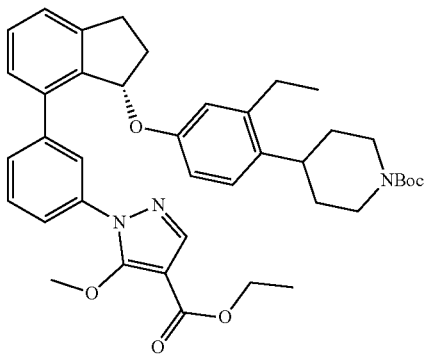 [SMILES: CCOC(=O)c1cnn(-c2cccc(-c3cccc4c3[C@@H](Oc3ccc(C5CCN(C(=O)OC(C)(C)C)CC5)c(CC)c3)CC4)c2)c1OC]

The title compound was made as described for Intermediate 16-1 starting from Intermediate 1-2 and Intermediate 13-1. MS (ESI+) m/z 666.3 (M+H).

Intermediate 19. Ethyl (S)-1-(3-(3-(3-ethyl-4-(piperidin-4-yl)phenoxy)-2,3-dihydro-1H-inden-4-yl)phenyl)-5-methoxy-1H-pyrazole-4-carboxylate

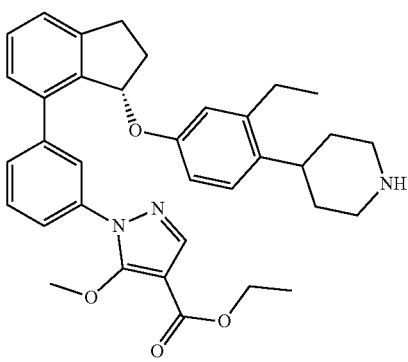 [SMILES: CCOC(=O)c1cnn(-c2cccc(-c3cccc4c3[C@@H](Oc3ccc(C5CCNCC5)c(CC)c3)CC4)c2)c1OC]

DIPEA (0.36 mL, 0.21 mmol) and TMSOTf (0.13 mL, 0.69 mmol) were successively added to a solution of Intermediate 19-1 (230 mg, 0.345 mmol) in DCM (10 mL) at 0° C. and the reaction mixture was stirred for 1 h. The reaction mixture was quenched with MeOH and concentrated under reduced pressure to obtain the title compound without the need for further purification. MS (ESI+) m/z 566.3 (M+H).

Intermediate 20. tert-Butyl (R)-4-(2-ethyl-4-((7-(4,4,5,5-tetramethyl-1,3,2-dioxaborolan-2-yl)-2,3-dihydro-1H-inden-1-yl)methyl)phenyl)piperidine-1-carboxylate

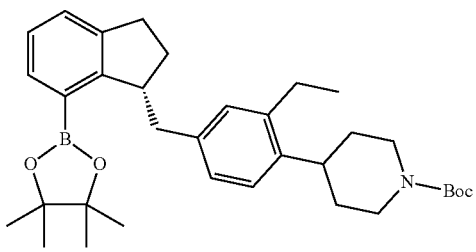 [SMILES: CCc1cc(C[C@H]2CCc3cccc(B4OC(C)(C)C(C)(C)O4)c32)ccc1C1CCN(C(=O)OC(C)(C)C)CC1]

Dioxane (6 mL) was added to a flask charged with tert-butyl (R)-4-(2-ethyl-4-((7-(((trifluoromethyl)sulfonyl)oxy)-2,3-dihydro-1H-inden-1-yl)methyl)phenyl)piperidine-1-carboxylate (Intermediate 11A; 800 mg, 1.41 mmol), KOAc (400 mg, 4.08 mmol), bis(pinacolato)diboron (800 mg, 3.15 mmol), and Pd(dppf)Cl$_2$·CH$_2$Cl$_2$ adduct (180 mg, 0.22 mmol) and the reaction mixture was heated to 105° C. for 12 h. The reaction mixture was then cooled to rt and diluted with DCM. The mixture was filtered and concentrated. The resulting residue was purified by FCC (0-25% EtOAc in heptane) to obtain the title compound. MS (ESI+) m/z 490.4 (M-tBu+2H).

Intermediate 21

Intermediate 21-1. Ethyl 1-(6-bromopyridin-2-yl)-5-hydroxy-1H-pyrazole-4-carboxylate

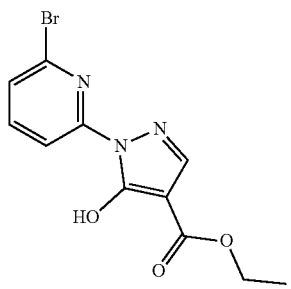 [SMILES: CCOC(=O)c1cnn(-c2cccc(Br)n2)c1O]

A mixture of 2-bromo-6-hydrazinylpyridine (8 g, 42.5 mmol), diethyl 2-(ethoxymethylene)malonate (10 mL, 49.9 mmol), and K$_2$CO$_3$ (7 g, 50.6 mmol) in H$_2$O (80 mL) and EtOH (40 mL) was stirred for 1 h at 100° C. The reaction mixture was cooled to rt and poured into ice and 10% aq. KHSO$_4$ (calcd. 1:1 mixture), and the pH of the mixture was adjusted to <2. The resulting solid was collected by filtration, and was dried under vacuum at 60° C. to afford the title compound without the need for further purification. MS (ESI+) m/z 314.1 (M($^{81}$Br)+H).

Intermediate 21. Ethyl 1-(6-bromopyridin-2-yl)-5-methoxy-1H-pyrazole-4-carboxylate

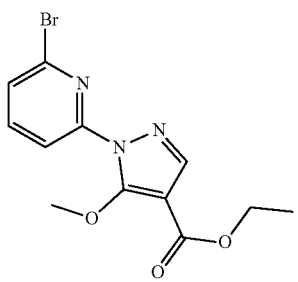 [SMILES: CCOC(=O)c1cnn(-c2cccc(Br)n2)c1OC]

TMS-diazomethane (2M in Et$_2$O; 15 mL, 30.0 mmol) was added dropwise over 5 min to a suspension of Intermediate 21-1 (6 g, 19.22 mmol) in toluene (200 mL) and MeOH (50 mL) at 0° C. The reaction mixture was stirred for 20 min before being quenched with AcOH (10 mL, 175 mmol). The resulting mixture was stirred for 1 h at rt, then diluted with EtOAc. The organic layer was washed successively with 5% aq. NaHCO$_3$, H$_2$O, and brine. The organic layer was dried over Na$_2$SO$_4$, filtered through a plug of silica gel, and the plug was washed with EtOAc. The filtrate was concentrated and the resulting residue was purified by FCC (10-100% acetone in heptane) to afford the title compound. MS (ESI+) m/z 328.1 (M($^{81}$Br)+H).

Intermediate 22. Ethyl 5-amino-1-(6-bromopyridin-2-yl)-1H-pyrazole-4-carboxylate

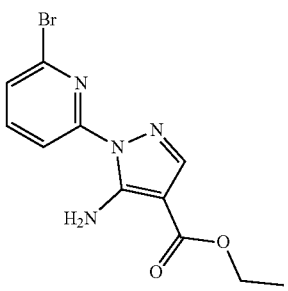 [SMILES: CCOC(=O)c1cnn(-c2cccc(Br)n2)c1N]

Ethyl 2-cyano-3-ethoxyacrylate (0.90 g, 5.35 mmol) was added to a solution of 2-bromo-6-hydrazinylpyridine (1.00 g, 5.35 mmol) in AcOH (15 mL) and water (5 mL) at rt. The reaction mixture was heated to 100° C. for 16 h. The reaction mixture was cooled to rt and made basic with sat. aq. NaHCO$_3$. The resulting solid was collected by filtration and dried under vacuum to obtain the title compound without the need for further purification. MS (ESI+) m/z 311.0 (M($^{79}$Br)+H).

Intermediate 23

Intermediate 23-1. tert-Butyl (R)-4-(4-((7-(6-(4-(ethoxycarbonyl)-5-methoxy-1H-pyrazol-1-yl)pyridin-2-yl)-2,3-dihydro-1H-inden-1-yl)methyl)-2-ethylphenyl)piperidine-1-carboxylate

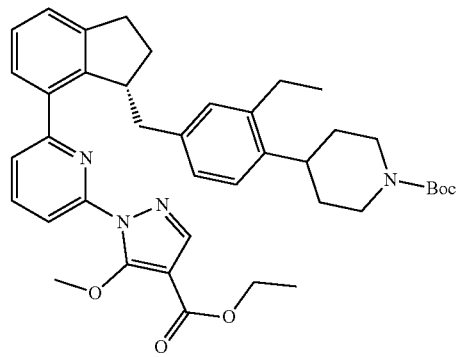 [SMILES: CCOC(=O)c1cnn(-c2cccc(-c3cccc4c3[C@@H](Cc3ccc(C5CCN(C(=O)OC(C)(C)C)CC5)c(CC)c3)CC4)n2)c1OC]

Pd(dppf)Cl$_2$·CH$_2$Cl$_2$ adduct (27.2 mg, 0.03 mmol) was added to a mixture of Intermediate 21 (202 mg, 0.62 mmol), tert-butyl (R)-4-(2-ethyl-4-((7-(4,4,5,5-tetramethyl-1,3,2-dioxaborolan-2-yl)-2,3-dihydro-1H-inden-1-yl)methyl)phenyl)piperidine-1-carboxylate (Intermediate 20; 260 mg, 0.48 mmol), and 2M aq. K$_3$PO$_4$ (0.72 mL, 1.43 mmol) in dioxane (5 mL) and the reaction mixture was heated to 100° C. for 1 h. The reaction mixture was cooled to rt and partitioned between EtOAc and water. The aqueous layer was extracted with EtOAc and the combined organic layer was concentrated. The resulting residue was purified by FCC (0-20% EtOAc in heptane) to the title compound. MS (ESI+) m/z 665.6 (M+H).

Intermediate 23. Ethyl (R)-1-(6-(3-(3-ethyl-4-(piperidin-4-yl)benzyl)-2,3-dihydro-1H-inden-4-yl)pyridin-2-yl)-5-methoxy-1H-pyrazole-4-carboxylate

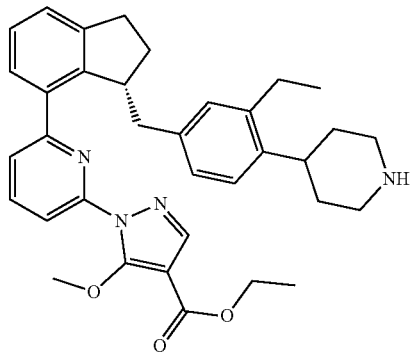 [SMILES: CCOC(=O)c1cnn(-c2cccc(-c3cccc4c3[C@@H](Cc3ccc(C5CCNCC5)c(CC)c3)CC4)n2)c1OC]

A solution of tert-butyl (R)-4-(4-((7-(6-(4-(ethoxycarbonyl)-5-methoxy-1H-pyrazol-1-yl)pyridin-2-yl)-2,3-dihydro-1H-inden-1-yl)methyl)-2-ethylphenyl)piperidine-1-carboxylate (Intermediate 23-1; 0.283 g, 0.425 mmol) in 4M HCl in dioxane solution (1.25 mL) was stirred at rt for 4 h. The reaction mixture was concentrated under reduced pressure to obtain the title compound without the need for further purification. MS (ESI+) m/z 565.5 (M+H).

Intermediate 24

Intermediate 24-1. tert-Butyl (S)-4-(4-((7-(6-(4-(ethoxycarbonyl)-5-methoxy-1H-pyrazol-1-yl)pyridin-2-yl)-2,3-dihydro-1H-inden-1-yl)oxy)-2-ethylphenyl)piperidine-1-carboxylate

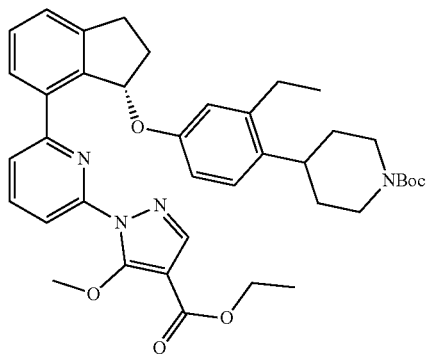 [SMILES: CCOC(=O)c1cnn(-c2cccc(-c3cccc4c3[C@@H](Oc3ccc(C5CCN(C(=O)OC(C)(C)C)CC5)c(CC)c3)CC4)n2)c1OC]

A solution of Intermediate 21 (200 mg, 0.615 mmol) in dioxane (10 mL) was added to a flask containing bis(pinocolato)diboron (171 mg, 0.676 mmol), Pd(dppf)Cl₂.CH₂Cl₂ adduct (50 mg, 0.061 mmol), and KOAc (90 mg, 0.92 mmol), and the reaction mixture was heated to 100° C. for 2 h. The reaction mixture was cooled back to rt, and a mixture of Intermediate 13-1 (215 mg, 0.43 mmol), K₃PO₄ (391 mg, 1.84 mmol), and Pd(dppf)Cl₂.CH₂Cl₂ adduct (50 mg, 0.061 mmol) in 1:1 dioxane:water (10 mL) was added. The reaction mixture was heated to 100° C. for 1 h. The reaction mixture was diluted with water, and extracted with EtOAc. The combined organic layers were washed with brine, dried over Na₂SO₄ and concentrated under reduced pressure. The residue was purified by FCC (20-25% EtOAc/hexanes) to give the title compound. MS (ESI+) m/z 667.4 (M+H).

Intermediate 24. Ethyl (S)-1-(6-(3-(3-ethyl-4-(piperidin-4-yl)phenoxy)-2,3-dihydro-1H-inden-4-yl)pyridin-2-yl)-5-methoxy-1H-pyrazole-4-carboxylate

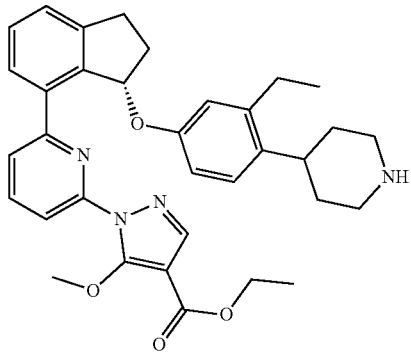 [SMILES: CCOC(=O)c1cnn(-c2cccc(-c3cccc4c3[C@@H](Oc3ccc(C5CCNCC5)c(CC)c3)CC4)n2)c1OC]

The title compound was synthesized by starting from Intermediate 24-1 and removing the Boc protecting group in a manner similar to that as described for Intermediate 13-2. MS (ESI+) m/z 567.3 (M+H).

Intermediate 25. Ethyl 1-(6-(3-((2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate

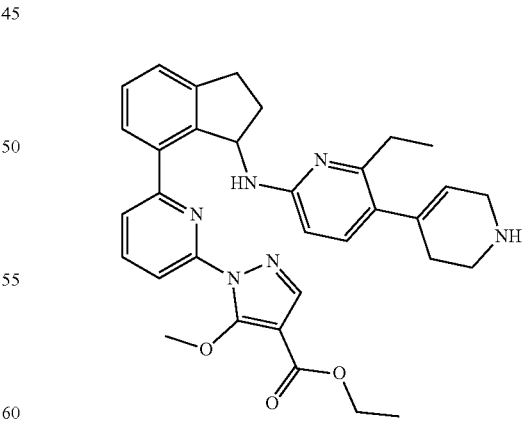

The title compound was synthesized by a similar method as described in Intermediate 24-1, starting from Intermediate 21 and Intermediate 14, followed by Boc deprotection using a similar method as described in Intermediate 15A. MS (ESI+) m/z 565.3 (M+H).

Intermediate 26

Intermediate 26-1. Ethyl 5-amino-1-(3-(4,4,5,5-tetramethyl-1,3,2-dioxaborolan-2-yl)phenyl)-1H-pyrazole-4-carboxylate

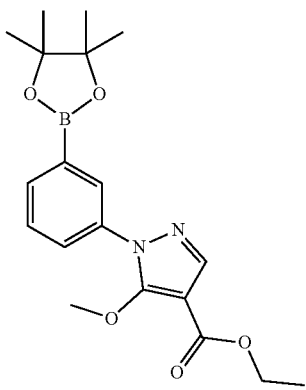 [SMILES: CCOC(=O)c1cnn(-c2cccc(B3OC(C)(C)C(C)(C)O3)c2)c1OC]

A solution of Intermediate 4-1 (300 mg, 0.97 mmol) in THF (10 mL) was added to bis(pinacolato)diboron (492 mg, 1.94 mmol), Pd(dppf)Cl$_2$·CH$_2$Cl$_2$ (158 mg, 0.19 mmol), and KOAc (190 mg, 1.94 mmol). The reaction mixture was heated to 80° C. for 16 h, and then cooled to rt. Celite® was added to the reaction mixture and the mixture was filtered and the filtrate was concentrated. The crude residue was used without the need for further purification. MS (ESI+) m/z 358.2 (M+H).

Intermediate 26-2. tert-Butyl (R)-4-(4-((7-(3-(5-amino-4-(ethoxycarbonyl)-1H-pyrazol-1-yl)phenyl)-2,3-dihydro-1H-inden-1-yl)methyl)-2-ethylphenyl)piperidine-1-carboxylate

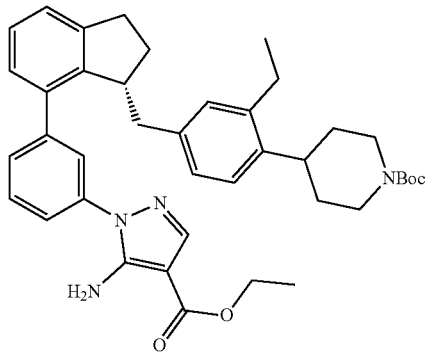 [SMILES: CCOC(=O)c1cnn(-c2cccc(-c3cccc4c3[C@@H](Cc3ccc(C5CCN(C(=O)OC(C)(C)C)CC5)c(CC)c3)CC4)c2)c1N]

A solution of Intermediate 11A (200 mg, 0.35 mmol) in dioxane (10 mL) and water (2 mL) was added to Intermediate 26-1 (151 mg, 0.35 mmol) and Na$_2$CO$_3$ (74 mg, 0.70 mmol) and the resulting mixture was sparged with nitrogen for 5 min. Pd(Ph$_3$)$_4$ (40 mg, 0.035 mmol) was added to the reaction mixture and the reaction mixture was heated to 90° C. for 3 h. The reaction mixture was concentrated and the residue was purified by FCC (10-15% EtOAc/hexanes) to provide the title compound. MS (ESI+) m/z 649.4 (M+H).

Intermediate 26. Ethyl (R)-5-amino-1-(3-(3-(3-ethyl-4-(piperidin-4-yl)benzyl)-2,3-dihydro-1H-inden-4-yl)phenyl)-1H-pyrazole-4-carboxylate

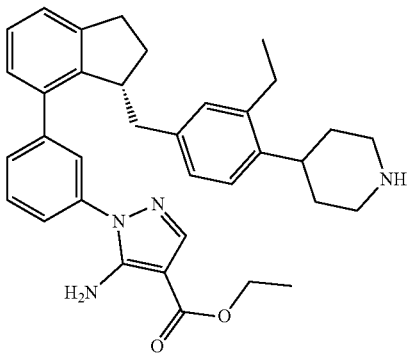 [SMILES: CCOC(=O)c1cnn(-c2cccc(-c3cccc4c3[C@@H](Cc3ccc(C5CCNCC5)c(CC)c3)CC4)c2)c1N]

The title compound was prepared as described for Intermediate 15A, starting from Intermediate 26-2. MS (ESI+) m/z 549.3 (M+H).

Intermediate 27

Intermediate 27-1. Ethyl 5-(methylamino)-1-(3-(4,4,5,5-tetramethyl-1,3,2-dioxaborolan-2-yl)phenyl)-1H-pyrazole-4-carboxylate

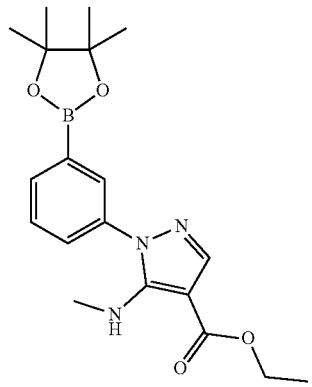 [SMILES: CCOC(=O)c1cnn(-c2cccc(B3OC(C)(C)C(C)(C)O3)c2)c1NC]

The title compound was made as described in Intermediate 26-1, starting with Intermediate 4. MS (ESI+) m/z 372.2 (M+H).

Intermediate 27. tert-Butyl (R)-4-(4-((7-(3-(4-(ethoxycarbonyl)-5-(methylamino)-1H-pyrazol-1-yl)phenyl)-2,3-dihydro-1H-inden-1-yl)methyl)-2-ethylphenyl)piperidine-1-carboxylate

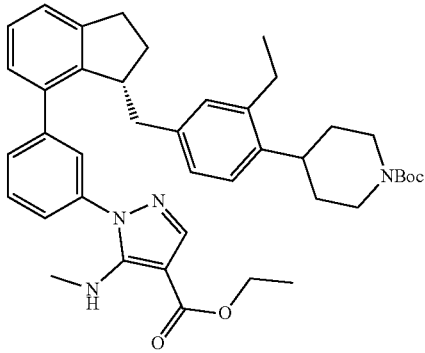 [SMILES: CCOC(=O)c1cnn(-c2cccc(-c3cccc4c3[C@@H](Cc3ccc(C5CCN(C(=O)OC(C)(C)C)CC5)c(CC)c3)CC4)c2)c1NC]

The title compound was made using a similar method as described for Intermediate 26-2, starting with Intermediate 27-1 and Intermediate 11A. MS (ESI+) m/z 663.4 (M+H).

Intermediate 28

Intermediate 28-1. tert-Butyl (R)-4-(4-((7-(6-(5-amino-4-(ethoxycarbonyl)-1H-pyrazol-1-yl)pyridin-2-yl)-2,3-dihydro-1H-inden-1-yl)methyl)-2-ethyl-phenyl)piperidine-1-carboxylate

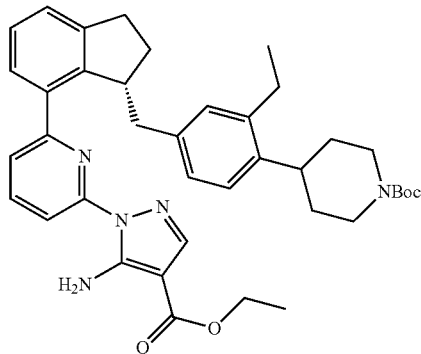 [SMILES: CCOC(=O)c1cnn(-c2cccc(-c3cccc4c3[C@@H](Cc3ccc(C5CCN(C(=O)OC(C)(C)C)CC5)c(CC)c3)CC4)n2)c1N]

A solution of Intermediate 22 (300 mg, 0.97 mmol), bis(pinocolato)diboron (490 mg, 1.94 mmol), KOAc (190 mg, 1.94 mmol), and Pd(dppf)Cl$_2$.CH$_2$Cl$_2$ (158 mg, 0.19 mmol) in THF (20 mL) was heated to 80° C. for 3 h. The reaction mixture was cooled to rt, filtered through a pad of Celite®, and concentrated. The residue was redissolved in dioxane (10 mL) and water (1 mL), and Intermediate 11A (300 mg, 0.53 mmol) and Na$_2$CO$_3$ (112 mg, 1.06 mmol) were added to the reaction mixture, and the mixture was sparged with nitrogen for 5 min. Pd(PPh$_3$)$_4$ (61 mg, 0.05 mmol) was then added to the reaction mixture, and the reaction mixture was heated to 100° C. for 4 h. The reaction mixture was diluted with water and extracted with EtOAc. The combined organic layers were washed with brine, dried over Na$_2$SO$_4$, and concentrated under reduced pressure. The residue was purified by FCC (10-15% EtOAc in hexanes) to give the title compound. MS (ESI+) m/z 650.4 (M+H).

Intermediate 28. Ethyl (R)-5-amino-1-(6-(3-(3-ethyl-4-(piperidin-4-yl)benzyl)-2,3-dihydro-1H-inden-4-yl)pyridin-2-yl)-1H-pyrazole-4-carboxylate

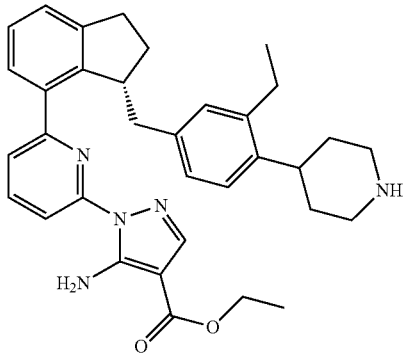 [SMILES: CCOC(=O)c1cnn(-c2cccc(-c3cccc4c3[C@@H](Cc3ccc(C5CCNCC5)c(CC)c3)CC4)n2)c1N]

The title compound was prepared using a similar method as described from Intermediate 15A, starting with Intermediate 28-1. MS (ESI+) m/z 540.4 (M+H).

Intermediate 29

Intermediate 29-1. 2-Ethyl-1',2',3',6'-tetrahydro-3,4'-bipyridine

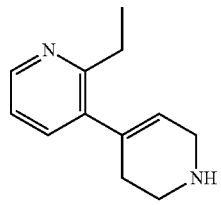

A solution of Intermediate 8-2 (7.5 g, 26.02 mmol) in 4M HCl in dioxane (75 mL) was stirred at rt for 1.5 h. The reaction mixture was concentrated, and the residue was treated with sat. aq. NaHCO$_3$. The mixture was extracted with EtOAc, and the combined organic layers were dried over Na$_2$SO$_4$, filtered, and concentrated to provide the title compound without the need for further purification. MS ESI+ m/z 189.2 (M+H).

Intermediate 29-2. Cyclopropyl(2-ethyl-3',6'-di-hydro-[3,4'-bipyridin]-1'(2'H)-yl)methanone

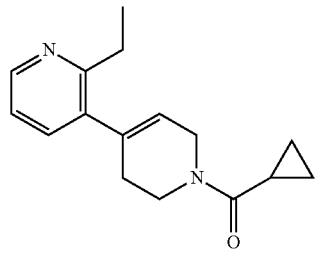 [SMILES: CCc1ncccc1C1=CCN(C(=O)C2CC2)CC1]

Triethylamine (11.12 mL, 79.73 mmol) was added to a solution of Intermediate 29-1 (5.0 g, 26.6 mmol) in DCM (50 mL) at rt, and the mixture was stirred for 10 min. Cyclopropyl carbonyl chloride (3.32 g, 31.9 mmol) was added to the reaction mixture, and the reaction mixture was stirred for 1 h. The reaction mixture was quenched with sat. aq. NaHCO$_3$ and extracted with EtOAc. The combined organic layers were dried over Na$_2$SO$_4$, filtered, and concentrated to give the title compound without the need for further purification. MS (ESI+) m/z 257.2 (M+H).

Intermediate 29-3. 1'-(Cyclopropanecarbonyl)-2-ethyl-1',2',3',6'-tetrahydro-[3,4'-bipyridine] 1-oxide

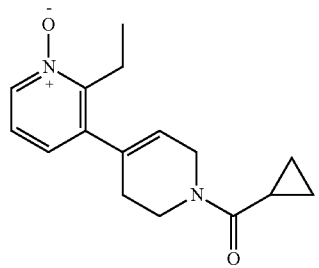

The title compound was prepared as described for Intermediate 8, starting from Intermediate 29-2. MS (ESI+) m/z 273.2 (M+H).

Intermediate 29. (6-((7-Bromo-2,3-dihydro-1H-inden-1-yl)amino)-2-ethyl-3',6'-dihydro-[3,4'-bipyridin]-1'(2'H)-yl)(cyclopropyl)methanone

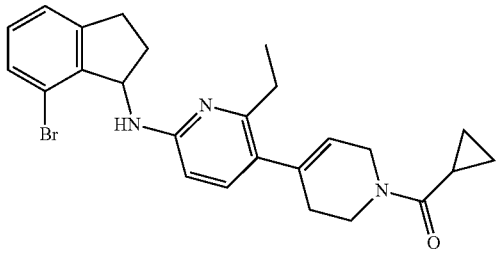 [SMILES: CCc1nc(NC2CCc3cccc(Br)c32)ccc1C1=CCN(C(=O)C2CC2)CC1]

The title compound was prepared using a method similar to that described for Intermediate 14, starting with Intermediate 29-3 and Intermediate 9. MS (ESI+) m/z 466.0 (M+H).

Example 1

Example 1-1. Ethyl (R)-1-(3-(3-(4-(1-(cyclopropanecarbonyl)piperidin-4-yl)-3-ethylbenzyl)-2,3-dihydro-1H-inden-4-yl)phenyl)-5-methoxy-1H-pyrazole-4-carboxylate

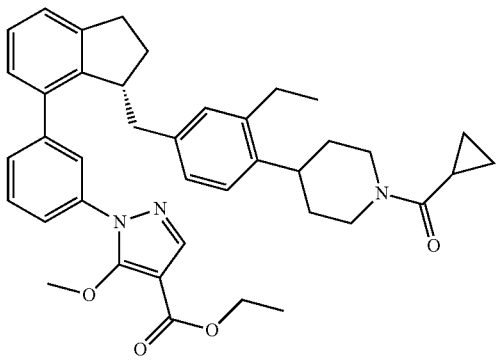 [SMILES: CCOC(=O)c1cnn(-c2cccc(-c3cccc4c3[C@@H](Cc3ccc(C5CCN(C(=O)C6CC6)CC5)c(CC)c3)CC4)c2)c1OC]

Cyclopropanecarboxylic acid (21 mg, 0.24 mmol), HATU (126 mg, 0.33 mmol), and DIPEA (0.39 mL, 2.21 mmol) were sequentially added to a solution of Intermediate 15A (ethyl (R)-1-(3-(3-(3-ethyl-4-(piperidin-4-yl)benzyl)-2,3-dihydro-1H-inden-4-yl)phenyl)-5-methoxy-1H-pyrazole-4-carboxylate, 150 mg, 0.22 mmol) in DMF (7 mL) at rt. The reaction mixture was stirred at rt for 3 h. The reaction mixture was diluted with water (100 mL) resulting in the formation of a precipitate. The solids were collected by filtration and dried under vacuum to obtain the title compound without the need for further purification. MS (ESI+) m/z 632.4 (M+H).

Example 1A. (+)-(R)-1-(3-(3-(4-(1-(Cyclopropanecarbonyl)piperidin-4-yl)-3-ethylbenzyl)-2,3-dihydro-1H-inden-4-yl)phenyl)-5-methoxy-1H-pyrazole-4-carboxylic acid

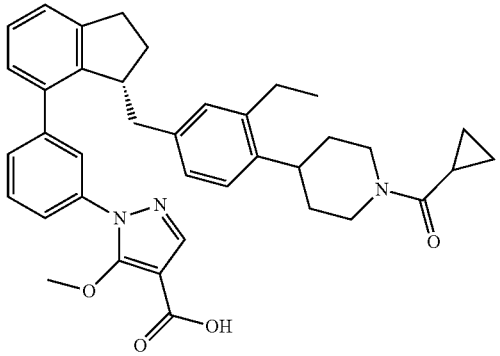 [SMILES: CCc1cc(C[C@H]2CCc3cccc(-c4cccc(-n5ncc(C(=O)O)c5OC)c4)c32)ccc1C1CCN(C(=O)C2CC2)CC1]

LiOH.H$_2$O (36 mg, 0.87 mmol) was added to a solution of Example 1-1 (ethyl (R)-1-(3-(3-(4-(1-(cyclopropanecarbonyl)piperidin-4-yl)-3-ethylbenzyl)-2,3-dihydro-1H-inden-4-yl)phenyl)-5-methoxy-1H-pyrazole-4-carboxylate; 110 mg, 0.17 mmol) in a mixed solvent system of THF:MeOH:water (1:1:1; 15 mL) and the mixture was heated to 70° C. for 4 h. The reaction mixture was cooled to rt and concentrated under reduced pressure. The resulting residue was dissolved in water and the mixture made acidic with citric acid, resulting in a solid precipitate. The solid was collected by filtration and dried under vacuum to give the title compound without the need for further purification. $^1$H NMR (400 MHz, METHANOL-d$_4$) δ 7.94 (s, 1H), 7.74 (s, 1H), 7.57-7.69 (m, 2H), 7.48-7.53 (m, 1H), 7.18-7.29 (m, 2H), 7.15 (d, J=7.2 Hz, 1H), 6.94 (d, J=7.8 Hz, 1H), 6.66 (br d, J=8.2 Hz, 1H), 6.57 (s, 1H), 4.63 (br d, J=12.6 Hz, 1H), 4.44 (br d, J=12.2 Hz, 1H), 4.10 (s, 3H), 3.79-3.87 (m, 1H), 3.20-3.27 (m, 1H), 2.95-3.06 (m, 1H), 2.80-2.93 (m, 2H), 2.67-2.78 (m, 1H), 2.56 (q, J=7.5 Hz, 2H), 2.42 (dd, J=3.7, 13.3 Hz, 1H), 2.20 (dd, J=9.7, 13.3 Hz, 1H), 2.04-2.13 (m, 1H), 1.88-2.03 (m, 2H), 1.44-1.83 (m, 4H), 1.08 (t, J=7.5 Hz, 3H), 0.76-0.95 (m, 4H). HRMS calcd. for C$_{38}$H$_{42}$N$_3$O$_4$ (M+H)$^+$ 604.3175, found 604.3170. The absolute stereochmistry of Example 1A was determined to be R based on three dimensional structure determination using X-ray single crystal diffraction.

Example 1B. (−)-(S)-1-(3-(3-(4-(1-(Cyclopropanecarbonyl)piperidin-4-yl)-3-ethylbenzyl)-2,3-dihydro-1H-inden-4-yl)phenyl)-5-methoxy-1H-pyrazole-4-carboxylic acid

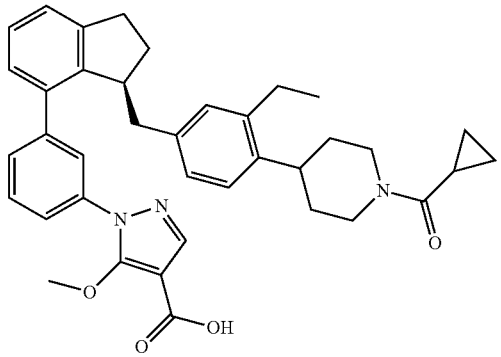 [SMILES: CCc1cc(C[C@@H]2CCc3cccc(-c4cccc(-n5ncc(C(=O)O)c5OC)c4)c32)ccc1C1CCN(C(=O)C2CC2)CC1]

The title compound was prepared from Intermediate 15B (ethyl (S)-1-(3-(3-(3-ethyl-4-(piperidin-4-yl)benzyl)-2,3-dihydro-1H-inden-4-yl)phenyl)-5-methoxy-1H-pyrazole-4-carboxylate) and cyclopropanecarboxylic acid in a fashion similar to that which was described for the preparation of Example 1A. The NMR and HRMS data are substantially identical to Example 1A.

Example 2

Example 2-1. Ethyl 1-(3-((R)-3-(3-ethyl-4-(1-((S)-2-hydroxypropanoyl)piperidin-4-yl)benzyl)-2,3-dihydro-1H-inden-4-yl)phenyl)-5-methoxy-1H-pyrazole-4-carboxylate

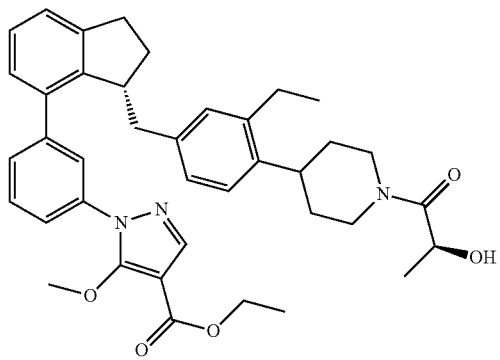 [SMILES: CCOC(=O)c1cnn(-c2cccc(-c3cccc4c3[C@@H](Cc3ccc(C5CCN(C(=O)[C@H](C)O)CC5)c(CC)c3)CC4)c2)c1OC]

L-(+)-Lactic acid (22 mg, 0.24 mmol), HATU (126 mg, 0.33 mmol), and DIPEA (0.39 mL, 2.21 mmol) were sequentially added to a solution of Intermediate 15A (ethyl (R)-1-(3-(3-(3-ethyl-4-(piperidin-4-yl)benzyl)-2,3-dihydro-1H-inden-4-yl)phenyl)-5-methoxy-1H-pyrazole-4-carboxylate; 150 mg, 0.22 mmol) in DMF (10 mL) at rt. The reaction mixture was stirred at rt for 3 h. The reaction mixture was diluted with water and extracted with Et$_2$O. The combined organic layers were washed with brine, dried over Na$_2$SO$_4$, filtered, and concentrated. The residue was purified by FCC (1-2% EtOH in DCM) to obtain the title compound. MS (ESI+) m/z 636.3 (M+H).

Example 2A. (+)-1-(3-((R)-3-(3-Ethyl-4-(1-((S)-2-hydroxypropanoyl)piperidin-4-yl)benzyl)-2,3-dihydro-1H-inden-4-yl)phenyl)-5-methoxy-1H-pyrazole-4-carboxylic acid

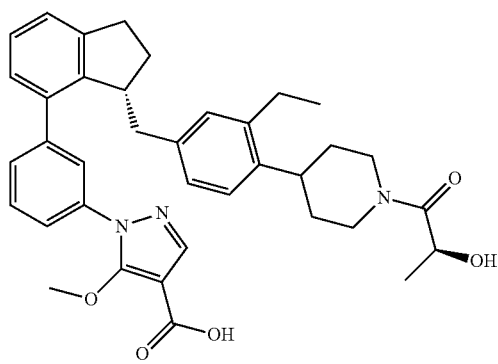 [SMILES: CCc1cc(C[C@H]2CCc3cccc(-c4cccc(-n5ncc(C(=O)O)c5OC)c4)c32)ccc1C1CCN(C(=O)[C@H](C)O)CC1]

LiOH·H$_2$O (33 mg, 0.55 mmol) was added to a solution of Example 2-1 (ethyl 1-(3-((R)-3-(3-ethyl-4-(1-((S)-2-hydroxypropanoyl)piperidin-4-yl)benzyl)-2,3-dihydro-1H-inden-4-yl)phenyl)-5-methoxy-1H-pyrazole-4-carboxylate; 70 mg, 0.11 mmol) in a mixed solvent system of THF:MeOH:water (1:1:1; 10 mL) and the reaction mixture was heated to 60° C. for 3 h. The reaction mixture was cooled to rt and concentrated under reduced pressure. The residue was dissolved in water, the mixture made acidic with citric acid, and then extracted with DCM. The combined organic layers were washed with brine, dried over Na$_2$SO$_4$, filtered, and concentrated. This residue was purified by FCC (5-10% MeOH in DCM) to give the title compound. $^1$H NMR (400 MHz, METHANOL-d$_4$) δ 7.94 (s, 1H), 7.73-7.76 (m, 1H), 7.59-7.68 (m, 2H), 7.47-7.54 (m, 1H), 7.18-7.28 (m, 2H), 7.13-7.17 (m, 1H), 6.93 (d, J=8.0 Hz, 1H), 6.61-6.70 (m, 1H), 6.57 (d, J=1.6 Hz, 1H), 4.55-4.69 (m, 2H), 4.06-4.15 (m, 4H), 3.78-3.88 (m, 1H), 3.15-3.25 (m, 1H), 2.94-3.04 (m, 1H), 2.81-2.90 (m, 2H), 2.69-2.79 (m, 1H), 2.55 (q, J=7.5 Hz, 2H), 2.37-2.46 (m, 1H), 2.16-2.24 (m, 1H), 2.05-2.15 (m, 1H), 1.86-1.96 (m, 1H), 1.51-1.78 (m, 4H), 1.30-1.37 (m, 3H), 1.08 (t, J=7.5 Hz, 3H). HRMS calcd. for C$_{37}$H$_{42}$N$_3$O$_5$ (M+H)$^+$ 608.3124, found 608.3148.

Example 2B. (−)-1-(3-((S)-3-(3-Ethyl-4-(1-((S)-2-hydroxypropanoyl)piperidin-4-yl)benzyl)-2,3-dihydro-1H-inden-4-yl)phenyl)-5-methoxy-1H-pyrazole-4-carboxylic acid

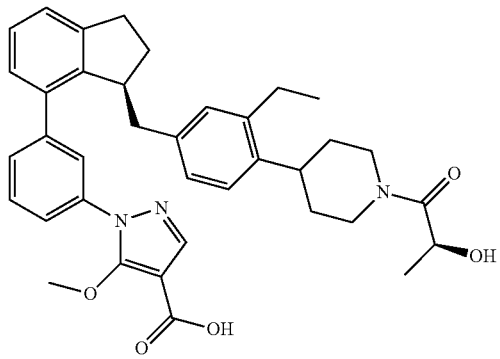 [SMILES: CCc1cc(C[C@@H]2CCc3cccc(-c4cccc(-n5ncc(C(=O)O)c5OC)c4)c32)ccc1C1CCN(C(=O)[C@H](C)O)CC1]

The title compound was prepared from Intermediate 15B (ethyl (S)-1-(3-(3-(3-ethyl-4-(piperidin-4-yl)benzyl)-2,3-dihydro-1H-inden-4-yl)phenyl)-5-methoxy-1H-pyrazole-4-carboxylate) and L-(+)-lactic acid using procedures similar to those described for the preparation of Example 2A. $^1$H NMR (400 MHz, METHANOL-d$_4$) δ 7.94 (s, 1H), 7.72-7.76 (m, 1H), 7.59-7.69 (m, 2H), 7.49-7.54 (m, 1H), 7.18-7.29 (m, 2H), 7.15 (d, J=7.0 Hz, 1H), 6.93 (d, J=8.0 Hz, 1H), 6.65 (dd, J=1.8, 8.0 Hz, 1H), 6.57 (br s, 1H), 4.54-4.68 (m, 2H), 4.04-4.16 (m, 4H), 3.79-3.88 (m, 1H), 3.15-3.23 (m, 1H), 2.93-3.05 (m, 1H), 2.81-2.90 (m, 2H), 2.69-2.81 (m, 1H), 2.55 (q, J=7.5 Hz, 2H), 2.37-2.46 (m, 1H), 2.03-2.26 (m, 2H), 1.88-1.97 (m, 1H), 1.48-1.79 (m, 4H), 1.29-1.40 (m, 3H), 1.08 (t, J=7.5 Hz, 3H). HRMS calcd. for C$_{37}$H$_{42}$N$_3$O$_5$ (M+H)$^+$ 608.3124, found 608.3126.

Example 3

Example 3-1. Ethyl 1-(3-(3-((4-(1-(cyclopropanecarbonyl)piperidin-4-yl)-3-ethylphenyl)amino)-2,3-dihydro-1H-inden-4-yl)phenyl)-5-methoxy-1H-pyrazole-4-carboxylate

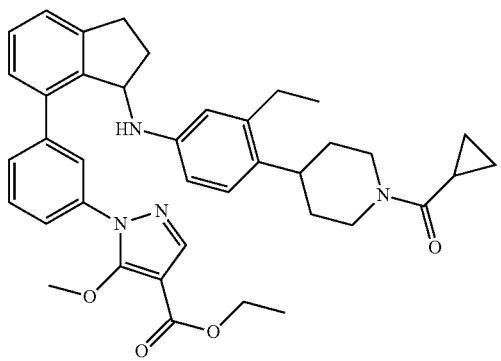 [SMILES: CCOC(=O)c1cnn(-c2cccc(-c3cccc4c3C(Nc3ccc(C5CCN(C(=O)C6CC6)CC5)c(CC)c3)CC4)c2)c1OC]

Cyclopropanecarboxylic acid (142 mg, 1.66 mmol), HATU (788 mg, 2.07 mmol), and DIPEA (1.2 mL, 6.91 mmol) were sequentially added to a solution of Intermediate 16 (780 mg, 1.38 mmol) in DMF (10 mL) at rt. The reaction mixture was stirred at rt for 16 h. The reaction mixture was then diluted with water and extracted with EtOAc. The combined organic layers were washed with brine, dried over Na$_2$SO$_4$, filtered, and concentrated. The residue was purified by FCC (20% EtOAc in hexanes) to provide the title compound. MS (ESI+) m/z 633.4 (M+H).

Example 3-2. Ethyl (R)-1-(3-(3-((4-(1-(cyclopropanecarbonyl)piperidin-4-yl)-3-ethylphenyl)amino)-2,3-dihydro-1H-inden-4-yl)phenyl)-5-methoxy-1H-pyrazole-4-carboxylate and ethyl (S)-1-(3-(3-((4-(1-(cyclopropanecarbonyl)piperidin-4-yl)-3-ethylphenyl)amino)-2,3-dihydro-1H-inden-4-yl)phenyl)-5-methoxy-1H-pyrazole-4-carboxylate Resolution of the enantiomers of ethyl 1-(3-(3-((4-(1-(cyclopropanecarbonyl)piperidin-4-yl)-3-ethylphenyl)amino)-2,3-dihydro-1H-inden-4-yl)phenyl)-5-methoxy-1H-pyrazole-4-carboxylate was achieved by chiral HPLC using CHIRALPAK® IA column with isocratic 30:70 (0.1% DEA in n-hexane):(EtOH) to give ethyl (R)-1-(3-(3-((4-(1-(cyclopropanecarbonyl)piperidin-4-yl)-3-ethylphenyl)amino)-2,3-dihydro-1H-inden-4-yl)phenyl)-5-methoxy-1H-pyrazole-4-carboxylate (t$_r$=5.09 min) and ethyl (S)-1-(3-(3-((4-(1-(cyclopropanecarbonyl)piperidin-4-yl)-3-ethylphenyl)amino)-2,3-dihydro-1H-inden-4-yl)phenyl)-5-methoxy-1H-pyrazole-4-carboxylate (t$_r$=12.92 min).

The absolute stereochemistry of the two enantiomers prepared in Example 3-2 was determined based on the indane stereocenter not epimerizing in the synthetic steps between this separation and Example 3A. The absolute stereochemistry of Example 3A was determined by X-ray single crystal diffraction.

Example 3A. (+)-(S)-1-(3-(3-((4-(1-(Cyclopropanecarbonyl)piperidin-4-yl)-3-ethylphenyl)amino)-2,3-dihydro-1H-inden-4-yl)phenyl)-5-methoxy-1H-pyrazole-4-carboxylic acid

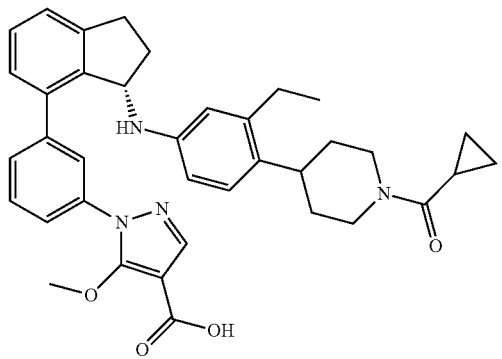 [SMILES: CCc1cc(N[C@H]2CCc3cccc(-c4cccc(-n5ncc(C(=O)O)c5OC)c4)c32)ccc1C1CCN(C(=O)C2CC2)CC1]

LiOH.H$_2$O (146 mg, 3.47 mmol) was added to a solution of (ethyl (S)-1-(3-(3-((4-(1-(cyclopropanecarbonyl)piperidin-4-yl)-3-ethylphenyl)amino)-2,3-dihydro-1H-inden-4-yl)phenyl)-5-methoxy-1H-pyrazole-4-carboxylate, t$_r$=12.92 min; 220 mg, 0.375 mmol) in a mixed solvent system of THF (5 mL), MeOH (2 mL), and water (2 mL). The reaction mixture was heated to 70° C. for 2 h before being concentrated under reduced pressure. The residue was dissolved in water (10 mL) and acidified with 1N aq. HCl, forming a solid precipitate. The solid was isolated by filtration, washed with water, and dried to provide the title compound without the need for further purification. $^1$H NMR (400 MHz, METHANOL-d$_4$) δ 7.77-7.90 (m, 2H), 7.53 (br. s., 1H), 7.42-7.50 (m, 2H), 7.32-7.42 (m, 2H), 7.28 (d, J=7.21 Hz, 1H), 6.77-6.89 (m, 1H), 6.27-6.40 (m, 2H), 5.01 (br. s., 1H), 4.57-4.68 (m, 1H), 4.38-4.50 (m, 1H), 3.92 (br. s., 3H), 3.18-3.28 (m, 2H), 2.85-2.99 (m, 2H), 2.66-2.77 (m, 1H), 2.45-2.61 (m, 2H), 2.29 (br. s., 1H), 2.17 (br. s, 1H), 1.95-2.04 (m, 1H), 1.42-1.81 (m, 4H), 1.10 (t, J=7.52 Hz, 3H), 0.76-0.95 (m, 4H). HRMS calcd. for C$_{37}$H$_{41}$N$_4$O$_4$ (M+H)$^+$ 605.3128, found 605.3120.

The absolute stereochemistry of Example 3A was determined by X-ray single crystal diffraction.

Example 3B. (−)-(R)-1-(3-(3-((4-(1-(Cyclopropanecarbonyl)piperidin-4-yl)-3-ethylphenyl)amino)-2,3-dihydro-1H-inden-4-yl)phenyl)-5-methoxy-1H-pyrazole-4-carboxylic acid

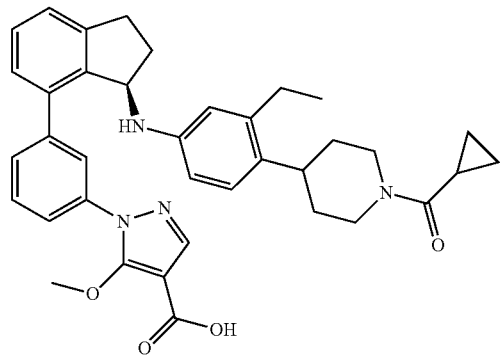 [SMILES: CCc1cc(N[C@@H]2CCc3cccc(-c4cccc(-n5ncc(C(=O)O)c5OC)c4)c32)ccc1C1CCN(C(=O)C2CC2)CC1]

Saponification of (ethyl (R)-1-(3-(3-((4-(1-(cyclopropanecarbonyl)piperidin-4-yl)-3-ethylphenyl)amino)-2,3-dihydro-1H-inden-4-yl)phenyl)-5-methoxy-1H-pyrazole-4-carboxylate, t$_r$=5.09 min) as described in Example 3A afforded the title compound. The NMR and HRMS data are substantially identical to Example 3A.

Example 4

Example 4-1. Ethyl 1-(3-(3-((3-ethyl-4-(1-((S)-2-hydroxypropanoyl)piperidin-4-yl)phenyl)amino)-2,3-dihydro-1H-inden-4-yl)phenyl)-5-methoxy-1H-pyrazole-4-carboxylate

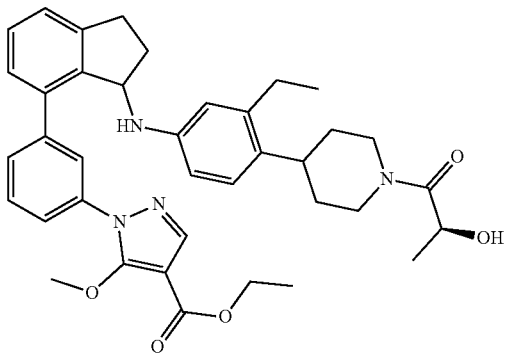 [SMILES: CCOC(=O)c1cnn(-c2cccc(-c3cccc4c3C(Nc3ccc(C5CCN(C(=O)[C@H](C)O)CC5)c(CC)c3)CC4)c2)c1OC]

The title compound was prepared from Intermediate 16 and L-(+)-lactic acid using a procedure similar to that described in Example 2-1. The residue was purified by FCC (60% EtOAc in hexanes) to obtain the title compound. MS (ESI+) m/z 637.4 (M+H).

Example 4-2. (diastereomer-1)-Ethyl 1-(3-(3-((3-ethyl-4-(1-((S)-2-hydroxypropanoyl)piperidin-4-yl)phenyl)amino)-2,3-dihydro-1H-inden-4-yl)phenyl)-5-methoxy-1H-pyrazole-4-carboxylate and (diastereomer-2)-ethyl 1-(3-(3-((3-ethyl-4-(1-((S)-2-hydroxypropanoyl)piperidin-4-yl)phenyl)amino)-2,3-dihydro-1H-inden-4-yl)phenyl)-5-methoxy-1H-pyrazole-4-carboxylate Resolution of the diastereomers of ethyl 1-(3-(3-((3-ethyl-4-(1-((S)-2-hydroxpropanoyl)piperidin-4-yl)phenyl)amino)-2,3-dihydro-1H-inden-4-yl)phenyl)-5-methoxy-1H-pyrazole-4-carboxylate was achieved by chiral HPLC using CHIRALPAK® IA column with isocratic 50:50 (0.1% DEA in n-hexane):(IPA:DCM [90:10]) to give (diastereomer-1)-ethyl 1-(3-(3-((3-ethyl-4-(1-((S)-2-hydroxypropanoyl)piperidin-4-yl)phenyl)amino)-2,3-dihydro-1H-inden-4-yl)phenyl)-5-methoxy-1H-pyrazole-4-carboxylate ($t_r$=5.00 min) and (diastereomer-2)-ethyl 1-(3-(3-((3-ethyl-4-(1-((S)-2-hydroxypropanoyl)piperidin-4-yl)phenyl)amino)-2,3-dihydro-1H-inden-4-yl)phenyl)-5-methoxy-1H-pyrazole-4-carboxylate ($t_r$=8.77 min).

Example 4A. (+)-1-(3-(3-((3-Ethyl-4-(1-((S)-2-hydroxypropanoyl)piperidin-4-yl)phenyl)amino)-2,3-dihydro-1H-inden-4-yl)phenyl)-5-methoxy-1H-pyrazole-4-carboxylic acid

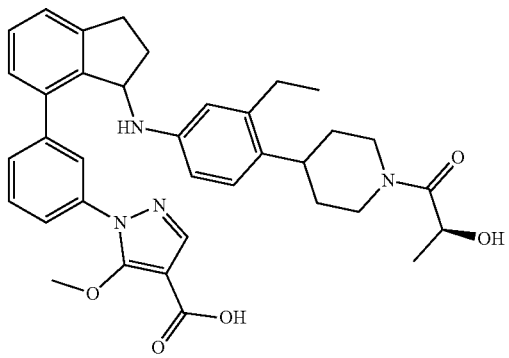 [SMILES: CCc1cc(NC2CCc3cccc(-c4cccc(-n5ncc(C(=O)O)c5OC)c4)c32)ccc1C1CCN(C(=O)[C@H](C)O)CC1]

Saponification of Example 4-2 ((diastereomer-2)-ethyl 1-(3-(3-((3-ethyl-4-(1-((S)-2-hydroxpropanoyl)piperidin-4-yl)phenyl)amino)-2,3-dihydro-1H-inden-4-yl)phenyl)-5-methoxy-1H-pyrazole-4-carboxylate, $t_r$=8.77 min) as described in Example 2A, followed by purification by FCC (3% MeOH in DCM) afforded the title compound. $^1$H NMR (400 MHz, METHANOL-$d_4$) δ 7.90 (br. s, 1H), 7.78 (s, 1H), 7.55-7.60 (m, 1H), 7.42-7.48 (m, 2H), 7.26-7.39 (m, 3H), 6.79 (br. d, J=8.4 Hz, 1H), 6.26-6.32 (m, 2H), 4.90-4.95 (m, 1H), 4.54-4.68 (m, 2H), 4.04-4.14 (m, 1H), 3.88 (s, 3H), 3.14-3.26 (m, 2H), 2.84-2.94 (m, 2H), 2.68-2.79 (m, 1H), 2.46-2.58 (m, 2H), 2.17-2.29 (m, 1H), 2.06-2.14 (m, 1H), 1.68-1.79 (m, 2H), 1.45-1.66 (m, 2H), 1.27-1.39 (m, 3H), 1.10 (t, J=7.6 Hz, 3H). HRMS calcd. for $C_{36}H_{41}N_4O_5$ (M+H)$^+$ 609.3077, found 609.3105.

Example 4B. (−)-1-(3-(3-((3-Ethyl-4-(1-((S)-2-hydroxypropanoyl)piperidin-4-yl)phenyl)amino)-2,3-dihydro-1H-inden-4-yl)phenyl)-5-methoxy-1H-pyrazole-4-carboxylic acid Saponification of Example 4-2 ((diastereomer-1)-ethyl 1-(3-(3-((3-ethyl-4-(1-((S)-2-hydroxpropanoyl)piperidin-4-yl)phenyl)amino)-2,3-dihydro-1H-inden-4-yl)phenyl)-5-methoxy-1H-pyrazole-4-carboxylate; $t_r$=5.00 min) as described in Example 2A, followed by purification by FCC (3% MeOH in DCM), afforded the title compound. $^1$H NMR (400 MHz, METHANOL-$d_4$) δ 7.88 (s, 1H), 7.78 (s, 1H), 7.56-7.60 (m, 1H), 7.43-7.46 (m, 2H), 7.30-7.39 (m, 2H), 7.26-7.30 (m, 1H), 6.79 (d, J=8.2 Hz, 1H), 6.26-6.32 (m, 2H), 4.91-4.95 (m, 1H), 4.54-4.68 (m, 2H), 4.04-4.15 (m, 1H), 3.88 (s, 3H), 3.15-3.26 (m, 2H), 2.84-2.94 (m, 2H), 2.68-2.79 (m, 1H), 2.52 (q, J=7.5 Hz, 2H), 2.18-2.30 (m, 1H), 2.00-2.14 (m, 1H), 1.67-1.79 (m, 2H), 1.47-1.63 (m, 2H), 1.30-1.39 (m, 3H), 1.10 (t, J=7.5 Hz, 3H). HRMS calcd. for $C_{36}H_{41}N_4O_5$ (M+H)$^+$ 609.3077, found 609.3082.

Example 5

Example 5-1. Ethyl (S)-1-(3-(3-(4-(1-(cyclopropanecarbonyl)piperidin-4-yl)-3-ethylphenoxy)-2,3-dihydro-1H-inden-4-yl)phenyl)-5-methoxy-1H-pyrazole-4-carboxylate

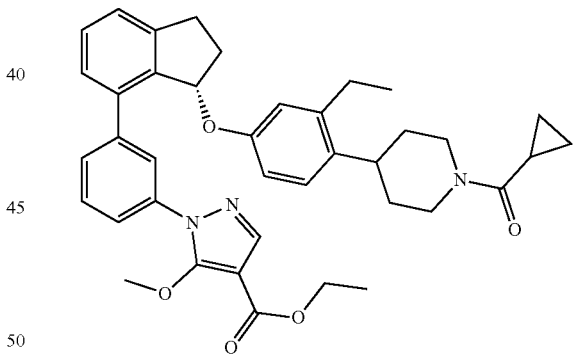

The title compound was prepared from Intermediate 19 (ethyl (S)-1-(3-(3-(3-ethyl-4-(piperidin-4-yl)phenoxy)-2,3-dihydro-1H-inden-4-yl)phenyl)-5-methoxy-1H-pyrazole-4-carboxylate) and cyclopropanecarboxylic acid using a procedure similar to that described in Example 1-1. The residue was purified by FCC (25% EtOAc in hexanes) to obtain the title compound. $^1$H NMR (400 MHz, DMSO-$d_6$): δ 7.81-7.83 (m, 2H), 7.51-7.57 (m, 2H), 7.31-7.45 (m, 4H), 6.98 (d, 1H, J=8.0 Hz), 6.61-6.69 (m, 2H), 5.58 (d, 1H, J=5.2 Hz), 4.71-4.85 (m, 1H), 4.35-4.41 (m, 1H), 4.30 (q, 2H, J=14.4, 7.6 Hz), 3.97 (s, 3H), 3.12-3.38 (m, 2H), 2.83-2.98 (m, 2H), 2.65-2.71 (m, 1H), 2.60 (q, 2H, J=14.4, 7.6 Hz), 2.19-2.41 (m, 2H), 1.58-1.85 (m, 5H), 1.37 (t, 3H, J=7.2 Hz), 1.67 (t, 3H, J=7.6 Hz), 0.92-1.08 (m, 2H), 0.73-0.81 (m, 2H).

Example 5. (+)-(S)-1-(3-(3-(4-(1-(Cyclopropanecarbonyl)piperidin-4-yl)-3-ethylphenoxy)-2,3-dihydro-1H-inden-4-yl)phenyl)-5-methoxy-1H-pyrazole-4-carboxylic acid

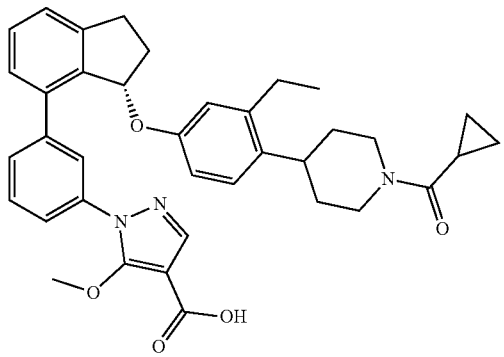 [SMILES: CCc1cc(O[C@H]2CCc3cccc(-c4cccc(-n5ncc(C(=O)O)c5OC)c4)c32)ccc1C1CCN(C(=O)C2CC2)CC1]

Saponification of Example 5-1 (ethyl (S)-1-(3-(3-(4-(1-(cyclopropanecarbonyl)piperidin-4-yl)-3-ethylphenoxy)-2,3-dihydro-1H-inden-4-yl)phenyl)-5-methoxy-1H-pyrazole-4-carboxylate) as described for Example 1A afforded the title compound without the need for further purification. $^1$H NMR (400 MHz, METHANOL-$d_4$) δ 7.81-7.85 (m, 1H), 7.77 (s, 1H), 7.51-7.56 (m, 1H), 7.42-7.49 (m, 3H), 7.38 (d, J=7.3 Hz, 1H), 7.34 (d, J=7.3 Hz, 1H), 6.96 (d, J=8.5 Hz, 1H), 6.60 (dd, J=2.7, 8.5 Hz, 1H), 6.57 (d, J=2.7 Hz, 1H), 5.56-5.60 (m, 1H), 4.60-4.71 (m, 1H), 4.42-4.51 (m, 1H), 3.85 (s, 3H), 3.21-3.28 (m, 2H), 2.90-3.02 (m, 2H), 2.69-2.79 (m, 1H), 2.55-2.66 (m, 2H), 2.20-2.35 (m, 2H), 1.97-2.05 (m, 1H), 1.45-1.85 (m, 4H), 1.14 (t, J=7.5 Hz, 3H), 0.77-0.96 (m, 4H). HRMS calcd. for $C_{37}H_{40}N_3O_5$ (M+H)$^+$ 606.2968, found 606.2961.

Example 6

Example 6-1. Ethyl 1-(3-((S)-3-(3-ethyl-4-(1-((S)-2-hydroxypropanoyl)piperidin-4-yl)phenoxy)-2,3-dihydro-1H-inden-4-yl)phenyl)-5-methoxy-1H-pyrazole-4-carboxylate

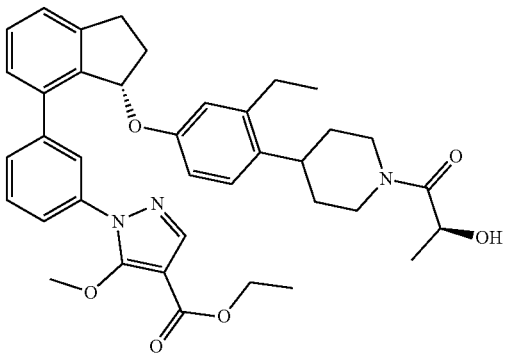 [SMILES: CCOC(=O)c1cnn(-c2cccc(-c3cccc4c3[C@@H](Oc3ccc(C5CCN(C(=O)[C@H](C)O)CC5)c(CC)c3)CC4)c2)c1OC]

The title compound was prepared from Intermediate 19 (ethyl (S)-1-(3-(3-(4-(1-(cyclopropanecarbonyl)piperidin-4-yl)-3-ethylphenoxy)-2,3-dihydro-1H-inden-4-yl)phenyl)-5-methoxy-1H-pyrazole-4-carboxylate) and L-(+)-lactic acid using a procedure similar to that described in Example 2-1.

The residue was purified by FCC (50% EtOAc in hexanes) to obtain the title compound. MS (ESI+) m/z 638.4 (M+H).

Example 6. 1-(3-((S)-3-(3-Ethyl-4-(1-((S)-2-hydroxypropanoyl)piperidin-4-yl)phenoxy)-2,3-dihydro-1H-inden-4-yl)phenyl)-5-methoxy-1H-pyrazole-4-carboxylic acid

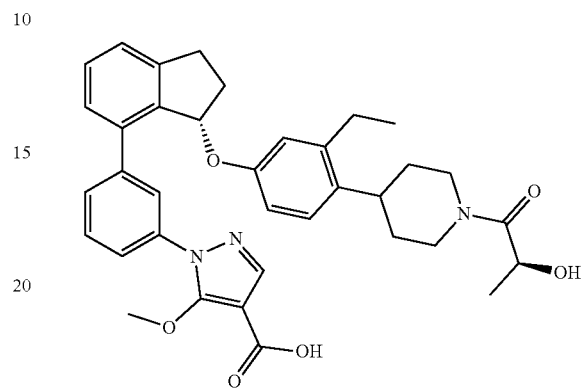

Saponification of Example 6-1 (ethyl 1-(3-((S)-3-(3-ethyl-4-(1-((S)-2-hydroxpropanoyl)piperidin-4-yl)phenoxy)-2,3-dihydro-1H-inden-4-yl)phenyl)-5-methoxy-1H-pyrazole-4-carboxylate) as described in Example 1A afforded the title compound without the need for further purification. $^1$H NMR (400 MHz, METHANOL-$d_4$) δ 7.80-7.85 (m, 1H), 7.76 (s, 1H), 7.51-7.56 (m, 1H), 7.41-7.50 (m, 3H), 7.36-7.41 (m, 1H), 7.34 (d, J=7.5 Hz, 1H), 6.95 (d, J=8.6 Hz, 1H), 6.54-6.64 (m, 2H), 5.58 (br. d, J=3.8 Hz, 1H), 4.53-4.70 (m, 2H), 4.06-4.18 (m, 1H), 3.85 (s, 3H), 3.14-3.28 (m, 2H), 2.89-3.02 (m, 2H), 2.70-2.81 (m, 1H), 2.54-2.66 (m, 2H), 2.21-2.35 (m, 2H), 1.48-1.83 (m, 4H), 1.27-1.40 (m, 3H), 1.14 (t, J=7.6 Hz, 3H). HRMS calcd. for $C_{36}H_{40}N_3O_6$ (M+H)$^+$ 610.2917, found 610.2915.

Example 7

Example 7-1. Ethyl 1-(5-(3-((4-(1-(cyclopropanecarbonyl)piperidin-4-yl)-3-ethylphenyl)amino)-2,3-dihydro-1H-inden-4-yl)-2-methylphenyl)-5-methoxy-1H-pyrazole-4-carboxylate

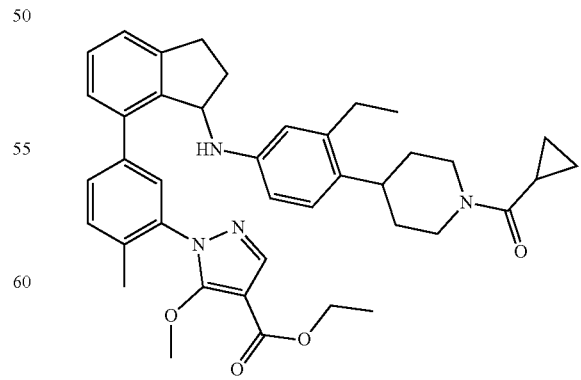

The title compound was prepared from Intermediate 17-1 and cyclopropanecarboxylic acid as described in Example 1-1, followed by purification by FCC (60% EtOAc in hexanes). MS (ESI+) m/z 647.4 (M+H).

Example 7-2. (enantiomer-1)-Ethyl 1-(5-(3-((4-(1-(cyclopropanecarbonyl)piperidin-4-yl)-3-ethylphenyl)amino)-2,3-dihydro-1H-inden-4-yl)-2-methylphenyl)-5-methoxy-1H-pyrazole-4-carboxylate and (enantiomer-2)-ethyl 1-(5-(3-((4-(1-(cyclopropanecarbonyl)piperidin-4-yl)-3-ethylphenyl)amino)-2,3-dihydro-1H-inden-4-yl)-2-methylphenyl)-5-methoxy-1H-pyrazole-4-carboxylate Resolution of the enantiomers of ethyl 1-(5-(3-((4-(1-(cyclopropanecarbonyl)piperidin-4-yl)-3-ethylphenyl)amino)-2,3-dihydro-1H-inden-4-yl)-2-methylphenyl)-5-methoxy-1H-pyrazole-4-carboxylate was achieved by chiral HPLC using CHIRALPAK® IC column with isocratic 60:20:20 (0.1% DEA in n-hexane):(EtOH):(IPA:DCM [90:10]) to give (enantiomer-1)-ethyl 1-(5-(3-((4-(1-(cyclopropanecarbonyl)piperid in-4-yl)-3-ethylphenyl)amino)-2,3-dihydro-1H-inden-4-yl)-2-methylphenyl)-5-methoxy-1H-pyrazole-4-carboxylate ($t_r$=18.36 min) and (enantiomer-2)-ethyl 1-(5-(3-((4-(1-cyclopropanecarbonyl)piperidin-4-yl)-3-ethylphenyl)amino)-2,3-dihydro-1H-inden-4-yl)-2-methylphenyl)-5-methoxy-1H-pyrazole-4-carboxylate ($t_r$=21.64 min).

Example 7A. (+)-1-(5-(3-((4-(1-(Cyclopropanecarbonyl)piperidin-4-yl)-3-ethylphenyl)amino)-2,3-dihydro-1H-inden-4-yl)-2-methylphenyl)-5-methoxy-1H-pyrazole-4-carboxylic acid

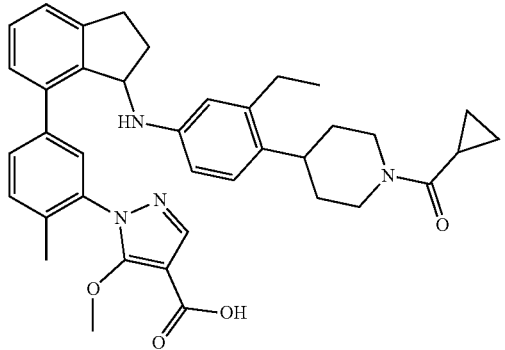 [SMILES: CCc1cc(NC2CCc3cccc(-c4ccc(C)c(-n5ncc(C(=O)O)c5OC)c4)c32)ccc1C1CCN(C(=O)C2CC2)CC1]

Saponification of Example 7-2 ((enantiomer-1)-ethyl 1-(5-(3-((4-(1-(cyclopropanecarbonyl)piperidin-4-yl)-3-ethylphenyl)amino)-2,3-dihydro-1H-inden-4-yl)-2-methylphenyl)-5-methoxy-1H-pyrazole-4-carboxylate, $t_r$=18.36 min), as described for Example 1A, afforded the title compound without the need for further purification. $^1$H NMR (400 MHz, METHANOL-$d_4$) δ 7.78 (s, 1H), 7.76 (d, J=1.8 Hz, 1H), 7.60 (dd, J=1.8, 8.0 Hz, 1H), 7.27-7.38 (m, 4H), 6.84 (d, J=8.2 Hz, 1H), 6.31-6.37 (m, 2H), 4.60-4.70 (m, 1H), 4.42-4.51 (m, 1H), 3.72 (s, 3H), 3.18-3.30 (m, 3H), 2.82-2.98 (m, 2H), 2.68-2.78 (m, 1H), 2.51-2.62 (m, 2H), 2.11-2.19 (m, 2H), 2.08 (s, 3H), 1.97-2.05 (m, 1H), 1.45-1.88 (m, 4H), 1.15 (t, J=7.6 Hz, 3H), 0.77-0.95 (m, 4H). HRMS calcd. for $C_{38}H_{43}N_4O_4$ (M+H)$^+$ 619.3284, found 619.3277.

Example 7B. (−)-1-(5-(3-((4-(1-(Cyclopropanecarbonyl)piperidin-4-yl)-3-ethylphenyl)amino)-2,3-dihydro-1H-inden-4-yl)-2-methylphenyl)-5-methoxy-1H-pyrazole-4-carboxylic acid Saponification of Example 7-2 ((enantiomer-2)-ethyl 1-(5-(3-((4-(1-(cyclopropanecarbonyl)piperidin-4-yl)-3-ethylphenyl)amino)-2,3-dihydro-1H-inden-4-yl)-2-methylphenyl)-5-methoxy-1H-pyrazole-4-carboxylate, $t_r$=21.64 min), as described for Example 1A, afforded the title compound without the need for further purification. The NMR and HRMS data are substantially identical to Example 7A.

Example 8

Example 8-1. Ethyl 1-(5-(3-((4-(1-(cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylate

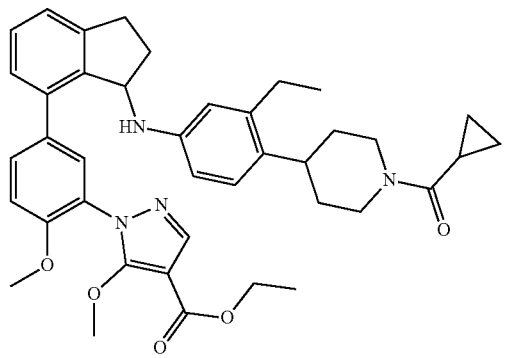 [SMILES: CCOC(=O)c1cnn(-c2cc(-c3cccc4c3C(Nc3ccc(C5CCN(C(=O)C6CC6)CC5)c(CC)c3)CC4)ccc2OC)c1OC]

The title compound was prepared from Intermediate 17-2 and cyclopropanecarboxylic acid as described in Example 1-1. The residue was purified by FCC (40% EtOAc in hexanes) to provide the title compound. MS (ESI+) m/z 663.1 (M+H).

Example 8-2. (enantiomer-1)-Ethyl 1-(5-(3-((4-(1-(cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylate and (enantiomer-2)-ethyl 1-(5-(3-((4-(1-(cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylate Resolution of the enantiomers of ethyl 1-(5-(3-((4-(1-(cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylate was achieved by chiral HPLC using CHIRALPAK® IA column with isocratic 30:70 (0.1% DEA in n-hexane):(IPA:DCM [90:10]) to give (enantiomer-1)-ethyl 1-(5-(3-((4-(1-(cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylate ($t_r$=4.14 min) and (enantiomer-2)-ethyl 1-(5-(3-((4-(1-(cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylate ($t_r$=10.62 min).

Example 8A. (+)-1-(5-(3-((4-(1-(Cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylic acid

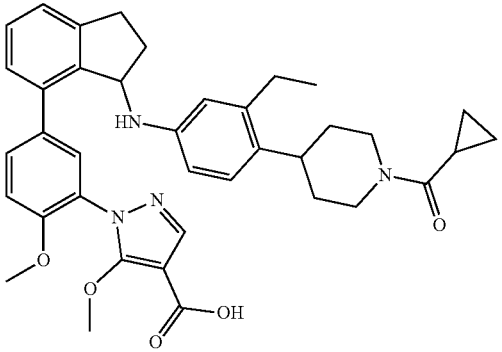 [SMILES: CCc1cc(NC2CCc3cccc(-c4ccc(OC)c(-n5ncc(C(=O)O)c5OC)c4)c32)ccc1C1CCN(C(=O)C2CC2)CC1]

Saponification of Example 8-2 ((enantiomer-1)-ethyl 1-(5-(3-((4-(1-(cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylate; $t_r$=4.14 min), as described in Example 1A, afforded the title compound without the need for further purification. $^1$H NMR (400 MHz, METHANOL-$d_4$) δ 7.73-7.77 (m, 2H), 7.70 (dd, J=2.3, 8.7 Hz, 1H), 7.31-7.36 (m, 1H), 7.26-7.30 (m, 2H), 7.14 (d, J=8.7 Hz, 1H), 6.85 (d, J=8.2 Hz, 1H), 6.32-6.39 (m, 2H), 4.82-4.84 (m, 1H), 4.60-4.70 (m, 1H), 4.41-4.51 (m, 1H), 3.83 (s, 3H), 3.81 (s, 3H), 3.17-3.27 (m, 2H), 2.81-2.98 (m, 2H), 2.68-2.78 (m, 1H), 2.51-2.62 (m, 2H), 2.11-2.19 (m, 2H), 1.97-2.06 (m, 1H), 1.43-1.87 (m, 4H), 1.14 (t, J=7.5 Hz, 3H), 0.76-0.96 (m, 4H). HRMS calcd. for $C_{38}H_{43}N_4O_5$ (M+H)$^+$ 635.3233, found 635.3230.

Example 8B. (−)-1-(5-(3-((4-(1-(Cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylic acid Saponification of Example 8-2 ((enantiomer-2)-ethyl 1-(5-(3-((4-(1-(cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylate; $t_r$=10.62 min), as described in Example 1A, afforded the title compound without the need for further purification. The NMR and HRMS data are substantially identical to Example 8A.

Example 9

Example 9-1. Ethyl 5-amino-1-(3-(3-((4-(1-(cyclopropanecarbonyl)piperidin-4-yl)-3-ethylphenyl)amino)-2,3-dihydro-1H-inden-4-yl)phenyl)-1H-pyrazole-4-carboxylate

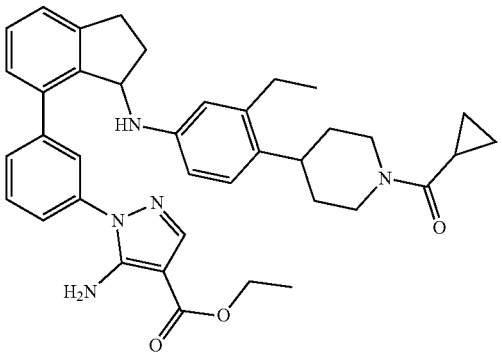 [SMILES: CCOC(=O)c1cnn(-c2cccc(-c3cccc4c3C(Nc3ccc(C5CCN(C(=O)C6CC6)CC5)c(CC)c3)CC4)c2)c1N]

Pd(dppf)Cl$_2$.CH$_2$Cl$_2$ adduct (105 mg, 0.13 mmol) was added to a solution of Intermediate 12 (600 mg, 1.29 mmol), bis(pinacolato)diboron (359 mg, 1.41 mmol), and KOAc (189 mg, 1.93 mmol) in dioxane (15 mL). The reaction mixture was stirred at 100° C. for 16 h, and then cooled to rt. Intermediate 4-1 (278 mg, 0.90 mmol) was added to the reaction mixture, followed by K$_3$PO$_4$ (819 mg, 3.86 mmol), Pd(dppf)Cl$_2$.CH$_2$Cl$_2$ adduct (105 mg, 0.13 mmol), and dioxane/water (1:1, 15 mL). The reaction mixture was stirred at 100° C. for another 4 h. The reaction mixture was cooled to rt and concentrated under reduced pressure. The residue was partitioned between water and EtOAc. The layers were separated, the aqueous layer was extracted with EtOAc, and the combined organic layers were dried over Na$_2$SO$_4$, filtered, and concentrated. The residue was purified by FCC (0-40% EtOAc in hexanes) to obtain the title compound. MS (ESI+) m/z 618.4 (M+H).

Example 9-2. (enantiomer-1)-Ethyl 5-amino-1-(3-(3-((4-(1-(cyclopropanecarbonyl)piperidin-4-yl)-3-ethylphenyl)amino)-2,3-dihydro-1H-inden-4-yl)phenyl)-1H-pyrazole-4-carboxylate and (enantiomer-2)-ethyl 5-amino-1-(3-(3-((4-(1-(cyclopropanecarbonyl)piperidin-4-yl)-3-ethylphenyl)amino)-2,3-dihydro-1H-inden-4-yl)phenyl)-1H-pyrazole-4-carboxylate Resolution of the enantiomers of ethyl 5-amino-1-(3-(3-((4-(1-(cyclopropanecarbonyl)piperidin-4-yl)-3-ethylphenyl)amino)-2,3-dihydro-1H-inden-4-yl)phenyl)-1H-pyrazole-4-carboxylate was achieved by chiral HPLC using CHIRALPAK® IA column with isocratic 60:40 (0.1% DEA in n-hexane):(IPA:DCM [80:20]) to give (enantiomer-1)-ethyl 5-amino-1-(3-(3-((4-(1-(cyclopropanecarbonyl)piperidin-4-yl)-3-ethylphenyl)amino)-2,3-dihydro-1H-inden-4-yl)phenyl)-1H-pyrazole-4-carboxylate ($t_r$=4.27 min) and (enantiomer-2)-ethyl 5-amino-1-(3-(3-((4-(1-(cyclopropanecarbonyl)piperidin-4-yl)-3-ethylphenyl)amino)-2,3-dihydro-1H-inden-4-yl)phenyl)-1H-pyrazole-4-carboxylate ($t_r$=7.73 min).

Example 9A. (+)-5-Amino-1-(3-(3-((4-(1-(cyclopropanecarbonyl)piperidin-4-yl)-3-ethylphenyl)amino)-2,3-dihydro-1H-inden-4-yl)phenyl)-1H-pyrazole-4-carboxylic acid

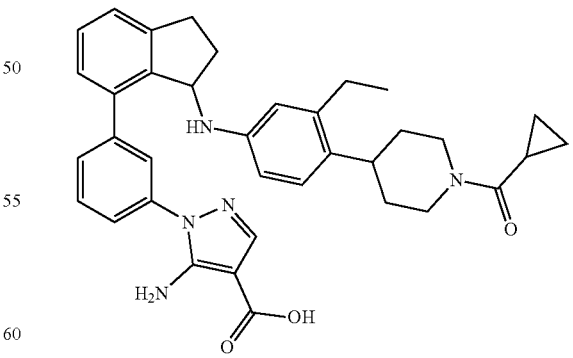

Saponification of Example 9-2 ((enantiomer-2)-ethyl 5-amino-1-(3-(3-((4-(1-(cyclopropanecarbonyl)piperidin-4-yl)-3-ethylphenyl)amino)-2,3-dihydro-1H-inden-4-yl)phenyl)-1H-pyrazole-4-carboxylate, $t_r$=7.73 min) as described in Example 2A, followed by purification of the residue by FCC (3-5% MeOH in DCM) provided the title compound. $^1$H NMR (400 MHz, METHANOL-$d_4$) δ 7.77 (br s, 1H), 7.58-7.66 (m, 2H), 7.49-7.56 (m, 1H), 7.31-7.44 (m, 3H), 7.26-7.30 (m, 1H), 6.86 (d, J=8.3 Hz, 1H), 6.29-6.37 (m, 2H), 4.94-4.99 (m, 1H), 4.61-4.68 (m, 1H), 4.41-4.49 (m, 1H), 3.16-3.27 (m, 2H), 2.85-2.98 (m, 2H), 2.72 (br t, J=12.8 Hz, 1H), 2.55 (q, J=7.5 Hz, 2H), 2.19-2.33 (m, 1H), 2.08-2.17 (m, 1H), 1.96-2.05 (m, 1H), 1.46-1.86 (m, 4H), 1.13 (t, J=7.5 Hz, 3H), 0.76-0.95 (m, 4H). HRMS calcd. for $C_{36}H_{40}N_5O_3$ (M+H)$^+$ 590.3131, found 590.3156.

Example 9B. (−)-5-Amino-1-(3-(3-((4-(1-(cyclopropanecarbonyl)piperidin-4-yl)-3-ethylphenyl)amino)-2,3-dihydro-1H-inden-4-yl)phenyl)-1H-pyrazole-4-carboxylic acid Saponification of Example 9-2 ((enantiomer-1)-ethyl 5-amino-1-(3-(3-((4-(1-cyclopropanecarbonyl)piperidin-4-yl)-3-ethylphenyl)amino)-2,3-dihydro-1H-inden-4-yl)phenyl)-1H-pyrazole-4-carboxylate, $t_r$=4.27 min), as described in Example 2A, followed by purification of the residue by FCC (3-5% MeOH in DCM) provided the title compound. The NMR and HRMS data are substantially identical to Example 9A.

Example 10

Example 10-1. Ethyl 1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylate

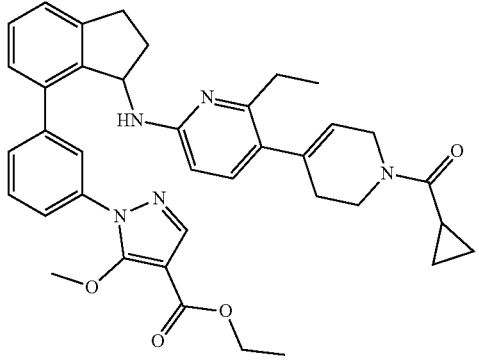 [SMILES: CCOC(=O)c1cnn(-c2cccc(-c3cccc4c3C(Nc3ccc(C5=CCN(C(=O)C6CC6)CC5)c(CC)n3)CC4)c2)c1OC]

The title compound was prepared from Intermediate 18 and cyclopropanecarboxylic acid as described in Example 1-1. The residue was purified by FCC (25-30% EtOAc in hexanes) to obtain the title compound. MS (ESI+) m/z 631.9 (M+H).

Example 10-2. (enantiomer-1)-Ethyl 1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylate and (enantiomer-2)-ethyl 1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylate Resolution of the enantiomers of ethyl 1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylate was achieved by chiral HPLC using CHIRALPAK® IA column with isocratic 60:20:20 (0.1% DEA in n-hexane):(EtOH):(IPA) to give (enantiomer-1)-ethyl 1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylate ($t_r$=5.30 min) and (enantiomer-2)-ethyl 1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylate ($t_r$=6.58 min).

Example 10A. (+)-1-(3-(3-((1'-(Cyclopropanecarbonyl)-2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylic acid

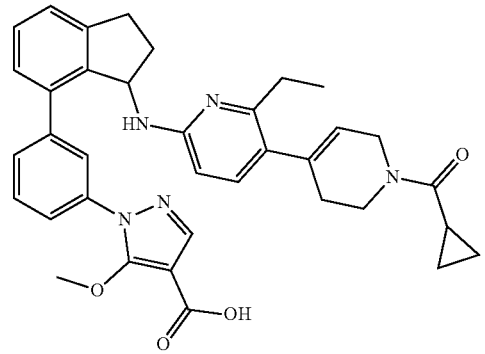 [SMILES: CCc1nc(NC2CCc3cccc(-c4cccc(-n5ncc(C(=O)O)c5OC)c4)c32)ccc1C1=CCN(C(=O)C2CC2)CC1]

LiOH.H$_2$O (43 mg, 1.03 mmol) was added to a solution of Example 10-2 ((enantiomer-2)-ethyl 1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylate; $t_r$=6.58 min; 65 mg, 0.10 mmol) in MeOH:THF:water (1:1:1; 15 mL) and the reaction mixture was heated to 90° C. for 12 h. The reaction mixture was evaporated and the residue was dissolved in water. The mixture was neutralized with citric acid and the resulting suspension was extracted with DCM. The combined organic layers were washed with brine, dried over Na$_2$SO$_4$, filtered, and concentrated. The residue was purified by FCC (5% MeOH in DCM) to obtain the title compound. $^1$H NMR (400 MHz, METHANOL-$d_4$) δ 7.74-7.82 (m, 2H), 7.44-7.51 (m, 2H), 7.31-7.43 (m, 3H), 7.27 (dd, J=1.5, 7.0 Hz, 1H), 7.08 (d, J=8.5 Hz, 1H), 6.19 (d, J=8.5 Hz, 1H), 5.59 (br d, J=12.0 Hz, 1H), 5.45-5.54 (m, 1H), 4.33-4.42 (m, 1H), 4.09-4.18 (m, 1H), 4.01 (s, 3H), 3.91-3.97 (m, 1H), 3.73-3.80 (m, 1H), 3.15-3.27 (m, 1H), 2.89-3.01 (m, 1H), 2.34-2.59 (m, 4H), 2.28 (br s, 1H), 1.90-2.11 (m, 2H), 1.11 (t, J=7.5 Hz, 3H), 0.78-0.98 (m, 4H). HRMS calcd. for $C_{36}H_{38}N_5O_4$ (M+H)$^+$ 604.2924, found 604.2948.

Example 10B. (−)-1-(3-(3-((1'-(Cyclopropanecarbonyl)-2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylic acid Saponification of Example 10-2 ((enantiomer-1)-ethyl 1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylate; t$_r$=5.30 min), as described in Example 10A, afforded the title compound. The NMR and HRMS data were substantially identical to Example 10A.

Example 11

Example 11-1. Ethyl 1-(3-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)phenyl)-5-methoxy-1H-pyrazole-4-carboxylate

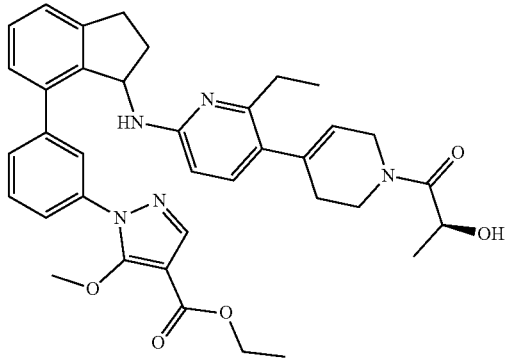 [SMILES: CCOC(=O)c1cnn(-c2cccc(-c3cccc4c3C(Nc3ccc(C5=CCN(C(=O)[C@H](C)O)CC5)c(CC)n3)CC4)c2)c1OC]

The title compound was prepared from Intermediate 18 and L-(+)-lactic acid as described in Example 2-1. The residue was purified by FCC (30% EtOH in DCM) to obtain the title compound. MS (ESI+) m/z 636.3 (M+H).

Example 11-2. (diastereomer-1)-Ethyl 1-(3-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)phenyl)-5-methoxy-1H-pyrazole-4-carboxylate and (diastereomer-2)-ethyl 1-(3-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)phenyl)-5-methoxy-1H-pyrazole-4-carboxylate Resolution of the diastereomers of ethyl 1-(3-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)phenyl)-5-methoxy-1H-pyrazole-4-carboxylate was achieved by chiral HPLC using CHIRALPAK® IA column with isocratic 50:50 (0.1% DEA in n-hexane):(IPA:DCM[80:20]) to give (diastereomer-1)-ethyl 1-(3-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)phenyl)-5-methoxy-1H-pyrazole-4-carboxylate (t$_r$=4.03 min) and (diastereomer-2)-ethyl 1-(3-(3-((2-ethyl-1'-((S)-2-hydroxpropanoyl)-1',2',3',6'-tetrahydro-[3,4'-bipyridin]-6-yl)amino)-2,3-dihydro-1H-inden-4-yl)phenyl)-5-methoxy-1H-pyrazole-4-carboxylate (t$_r$=9.03 min).

Example 11A. 1-(3-((S or R)-3-((2-Ethyl-1'-((S)-2-hydroxypropanoyl)-1',2',3',6'-tetrahydro-[3,4'-bipyridin]-6-yl)amino)-2,3-dihydro-1H-inden-4-yl)phenyl)-5-methoxy-1H-pyrazole-4-carboxylic acid

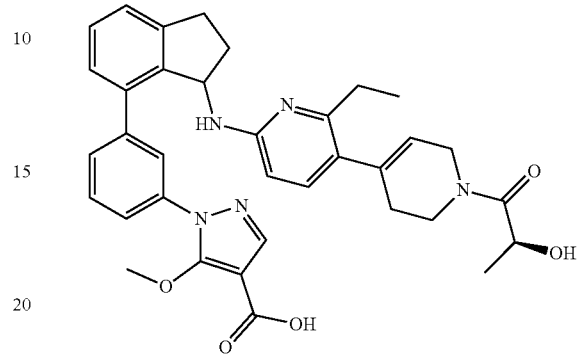

Saponification of ((diastereomer 1)-ethyl 1-(3-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)phenyl)-5-methoxy-1H-pyrazole-4-carboxylate; t$_r$=4.03 min) as described in Example 2A, and purification of the residue by FCC (10% MeOH in DCM) provided the title compound. $^1$H NMR (400 MHz, METHANOL-d$_4$) δ 7.79 (s, 1H), 7.72-7.76 (m, 1H), 7.47-7.53 (m, 1H), 7.35-7.47 (m, 4H), 7.19-7.32 (m, 2H), 6.38 (br d, J=7.8 Hz, 1H), 5.58-5.69 (m, 1H), 5.52 (dd, J=4.0, 6.8 Hz, 1H), 4.58-4.68 (m, 1H), 4.10-4.32 (m, 2H), 4.02-4.10 (m, 3H), 3.67-3.93 (m, 2H), 3.18-3.25 (m, 1H), 2.93-3.05 (m, 1H), 2.45-2.64 (m, 3H), 2.26-2.40 (m, 2H), 2.00-2.11 (m, 1H), 1.31-1.44 (m, 3H), 1.12 (t, J=7.5 Hz, 3H). HRMS calcd. for C$_{35}$H$_{38}$N$_5$O$_5$ (M+H)$^+$ 608.2873, found 608.2878.

Example 11B. 1-(3-((R or S)-3-((2-ethyl-1'-((S)-2-hydroxypropanoyl)-1',2',3',6'-tetrahydro-[3,4'-bipyridin]-6-yl)amino)-2,3-dihydro-1H-inden-4-yl)phenyl)-5-methoxy-1H-pyrazole-4-carboxylic acid Saponification of ((diastereomer 2)-ethyl 1-(3-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)phenyl)-5-methoxy-1H-pyrazole-4-carboxylate; t$_r$=9.03 min) as described in Example 2A, and purification of the residue by FCC (10% MeOH in DCM) provided the title compound. $^1$H NMR (400 MHz, METHANOL-d$_4$) δ 7.79 (s, 1H), 7.72-7.75 (m, 1H), 7.47-7.54 (m, 1H), 7.34-7.46 (m, 4H), 7.23-7.31 (m, 2H), 6.41 (br d, J=8.8 Hz, 1H), 5.62-5.68 (m, 1H), 5.50-5.56 (m, 1H), 4.57-4.68 (m, 1H), 4.08-4.31 (m, 2H), 4.06 (s, 3H), 3.69-3.92 (m, 2H), 3.17-3.27 (m, 1H), 2.94-3.06 (m, 1H), 2.46-2.66 (m, 3H), 2.23-2.44 (m, 2H), 2.00-2.12 (m, 1H), 1.32-1.40 (m, 3H), 1.13 (br t, J=7.5 Hz, 3H). HRMS calcd. for C$_{35}$H$_{38}$N$_5$O$_5$ (M+H)$^+$ 608.2873, found 608.2892.

Example 12

Example 12-1. Ethyl 1-(3-(3-((4-(1-(cyclopropanecarbonyl)piperidin-4-yl)-3-ethylphenyl)amino)-2,3-dihydro-1H-inden-4-yl)phenyl)-5-(methylamino)-1H-pyrazole-4-carboxylate

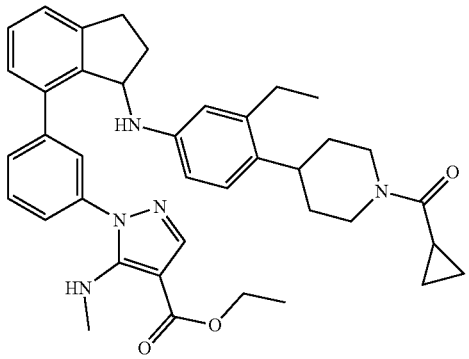 [SMILES: CCOC(=O)c1cnn(-c2cccc(-c3cccc4c3C(Nc3ccc(C5CCN(C(=O)C6CC6)CC5)c(CC)c3)CC4)c2)c1NC]

The title compound was prepared from Intermediate 12 and Intermediate 4 as described in Example 9-1. MS (ESI+) m/z 632.4 (M+H).

Example 12-2. (enantiomer-1)-Ethyl 1-(3-(3-((4-(1-(cyclopropanecarbonyl)piperidin-4-yl)-3-ethylphenyl)amino)-2,3-dihydro-1H-inden-4-yl)phenyl)-5-(methylamino)-1H-pyrazole-4-carboxylate and (enantiomer-2)-ethyl 1-(3-(3-((4-(1-(cyclopropanecarbonyl)piperidin-4-yl)-3-ethylphenyl)amino)-2,3-dihydro-1H-inden-4-yl)phenyl)-5-(methylamino)-1H-pyrazole-4-carboxylate Resolution of the enantiomers of ethyl 1-(3-(3-((4-(1-(cyclopropanecarbonyl)piperidin-4-yl)-3-ethylphenyl)amino)-2,3-dihydro-1H-inden-4-yl)phenyl)-5-(methylamino)-1H-pyrazole-4-carboxylate was achieved by chiral HPLC using CHIRALPAK® IA column with isocratic 50:50 (0.1% DEA in n-hexane):(IPA:DCM [80:20]) to give (enantiomer-1)-ethyl 1-(3-(3-((4-(1-(cyclopropanecarbonyl)piperidin-4-yl)-3-ethylphenyl)amino)-2,3-dihydro-1H-inden-4-yl)phenyl)-5-(methylamino)-1H-pyrazole-4-carboxylate ($t_r$=3.75 min) and (enantiomer-2)-ethyl 1-(3-(3-((4-(1-(cyclopropanecarbonyl)piperidin-4-yl)-3-ethylphenyl)amino)-2,3-dihydro-1H-inden-4-yl)phenyl)-5-(methylamino)-1H-pyrazole-4-carboxylate ($t_r$=8.46 min).

Example 12A. (enantiomer-1)-1-(3-(3-((4-(1-(Cyclopropanecarbonyl)piperidin-4-yl)-3-ethylphenyl)amino)-2,3-dihydro-1H-inden-4-yl)phenyl)-5-(methylamino)-1H-pyrazole-4-carboxylic acid

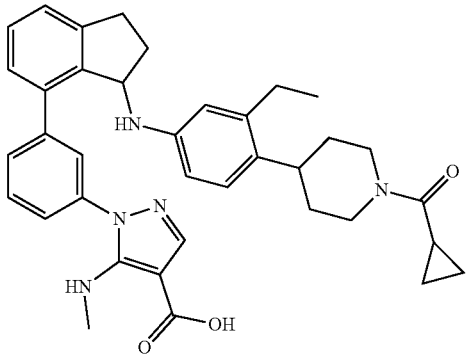 [SMILES: CCc1cc(NC2CCc3cccc(-c4cccc(-n5ncc(C(=O)O)c5NC)c4)c32)ccc1C1CCN(C(=O)C2CC2)CC1]

Saponification of ((enantiomer-1)-ethyl 1-(3-(3-((4-(1-(cyclopropanecarbonyl)piperidin-4-yl)-3-ethylphenyl)amino)-2,3-dihydro-1H-inden-4-yl)phenyl)-5-(methylamino)-1H-pyrazole-4-carboxylate, $t_r$=3.75 min) as described in Example 1A afforded the title compound without the need for further purification. $^1$H NMR (400 MHz, METHANOL-$d_4$) δ 7.80 (br s, 1H), 7.66 (s, 1H), 7.60 (d, J=7.7 Hz, 1H), 7.46 (t, J=7.8 Hz, 1H), 7.30-7.40 (m, 3H), 7.23-7.28 (m, 1H), 6.81 (d, J=8.9 Hz, 1H), 6.28-6.34 (m, 2H), 4.70-4.90 (m, 1H), 4.60-4.70 (m, 1H), 4.40-4.50 (m, 1H), 3.17-3.26 (m, 2H), 2.85-2.96 (m, 2H), 2.67-2.77 (m, 1H), 2.54 (q, J=7.5 Hz, 2H), 2.18-2.29 (m, 4H), 2.07-2.16 (m, 1H), 1.95-2.05 (m, 1H), 1.44-1.84 (m, 4H), 1.12 (t, J=7.5 Hz, 3H), 0.77-0.95 (m, 4H). HRMS calcd. for $C_{37}H_{42}N_5O_3$ (M+H)$^+$ 604.3288, found 604.3301.

Example 12B. (enantiomer-2)-1-(3-(3-((4-(1-(Cyclopropanecarbonyl)piperidin-4-yl)-3-ethylphenyl)amino)-2,3-dihydro-1H-inden-4-yl)phenyl)-5-(methylamino)-1H-pyrazole-4-carboxylic acid Saponification of ((enantiomer-2)-ethyl 1-(3-(3-((4-(1-(cyclopropanecarbonyl)piperidin-4-yl)-3-ethylphenyl)amino)-2,3-dihydro-1H-inden-4-yl)phenyl)-5-(methylamino)-1H-pyrazole-4-carboxylate, $t_r$=8.46 min) as described in Example 1A afforded the title compound without the need for further purification. The NMR and HRMS data are substantially identical to Example 12A.

Example 13

Example 13-1. Ethyl (R)-1-(6-(3-(4-(1-(cyclopropanecarbonyl)piperidin-4-yl)-3-ethylbenzyl)-2,3-dihydro-1H-inden-4-yl)pyridin-2-yl)-5-methoxy-1H-pyrazole-4-carboxylate

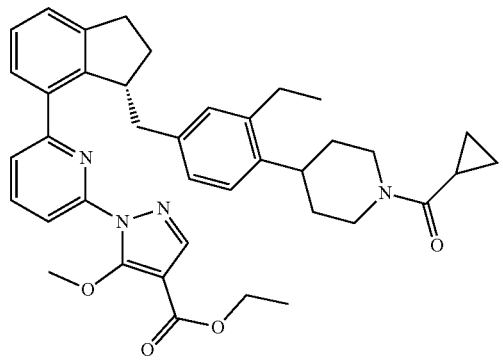 [SMILES: CCOC(=O)c1cnn(-c2cccc(-c3cccc4c3[C@@H](Cc3ccc(C5CCN(C(=O)C6CC6)CC5)c(CC)c3)CC4)n2)c1OC]

Cyclopropanecarbonyl chloride (0.04 mL, 0.45 mmol) was added to a solution of ethyl (R)-1-(6-(3-(3-ethyl-4-(piperidin-4-yl)benzyl)-2,3-dihydro-1H-inden-4-yl)pyridin-2-yl)-5-methoxy-1H-pyrazole-4-carboxylate (Intermediate 23; 240 mg, 0.43 mmol) and DIPEA (0.22 mL, 1.28 mmol) in DCM (5 mL) at 0° C. The reaction mixture was stirred at 0° C. for 0.5 h. The reaction mixture was partitioned between water and DCM. The organic phase was passed through an Isolute® phase separator and concentrated. The resulting residue was purified by FCC (0-100% EtOAc in heptane) to obtain the title compound. MS (ESI+) m/z 633.6 (M+H).

Example 13. (+)-(R)-1-(6-(3-(4-(1-(Cyclopropanecarbonyl)piperidin-4-yl)-3-ethylbenzyl)-2,3-dihydro-1H-inden-4-yl)pyridin-2-yl)-5-methoxy-1H-pyrazole-4-carboxylic acid

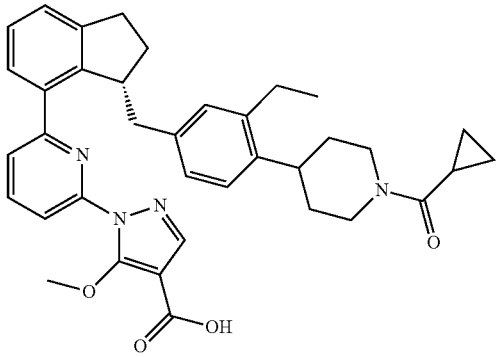 [SMILES: CCc1cc(C[C@H]2CCc3cccc(-c4cccc(-n5ncc(C(=O)O)c5OC)n4)c32)ccc1C1CCN(C(=O)C2CC2)CC1]

1N aq. LiOH (1.50 mL, 1.50 mmol) was added to a solution of ethyl (R)-1-(6-(3-(4-(1-(cyclopropanecarbonyl)piperidin-4-yl)-3-ethylbenzyl)-2,3-dihydro-1H-inden-4-yl)pyridin-2-yl)-5-methoxy-1H-pyrazole-4-carboxylate (Example 13-1; 140 mg, 0.22 mmol) in THF (3 mL) and MeOH (3 mL). The reaction mixture was heated to 50° C. for 16 h. The reaction mixture was cooled to rt and 1N HCl aq (1.5 mL) was added, and the resulting mixture was extracted with EtOAc. The combined organic layers were concentrated and the resulting residue was purified by RP-HPLC (stationary phase: Gemini® NX 5μ C18 110A 100×30 mm; mobile phase: gradient, water with 0.1% (28% ammonium hydroxide)/acetonitrile), and then further recrystallized from MeOH to obtain the title compound. $^1$H NMR (400 MHz, Methanol-$d_4$) δ 8.03 (t, J=7.9 Hz, 1H), 7.98 (s, 1H), 7.67-7.61 (m, 2H), 7.44-7.38 (m, 1H), 7.31-7.27 (m, 2H), 6.88 (d, J=7.8 Hz, 1H), 6.64-6.59 (m, 2H), 4.64 (d, J=12.7 Hz, 1H), 4.45 (d, J=13.8 Hz, 1H), 4.38-4.30 (m, 1H), 4.13 (s, 3H), 3.27-3.20 (m, 1H), 3.05-2.89 (m, 2H), 2.83 (dd, J=15.9, 7.1 Hz, 1H), 2.78-2.68 (m, 1H), 2.60-2.45 (m, 3H), 2.27-2.19 (m, 1H), 2.14-1.95 (m, 2H), 1.90 (dd, J=12.7, 7.8 Hz, 1H), 1.84-1.47 (m, 4H), 1.07 (t, J=7.6 Hz, 3H), 0.96-0.75 (m, 4H). HRMS calcd. for $C_{37}H_{41}N_4O_4$ (M+H)$^+$ 605.3128, found 605.3144.

Example 14

Example 14-1. Ethyl (S)-1-(6-(3-(4-(1-(cyclopropanecarbonyl)piperidin-4-yl)-3-ethylphenoxy)-2,3-dihydro-1H-inden-4-yl)pyridin-2-yl)-5-methoxy-1H-pyrazole-4-carboxylate

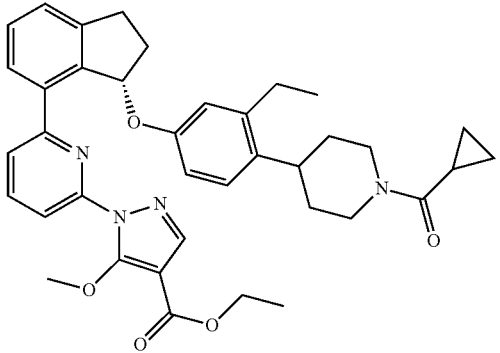 [SMILES: CCOC(=O)c1cnn(-c2cccc(-c3cccc4c3[C@@H](Oc3ccc(C5CCN(C(=O)C6CC6)CC5)c(CC)c3)CC4)n2)c1OC]

Cyclopropanecarboxylic acid (9 mg, 0.11 mmol), HATU (43 mg, 0.11 mmol), and DIPEA (0.09 mL, 0.53 mmol) were added sequentially to a solution of ethyl (S)-1-(6-(3-(3-ethyl-4-(piperidin-4-yl)phenoxy)-2,3-dihydro-1H-inden-4-yl)pyridin-2-yl)-5-methoxy-1H-pyrazole-4-carboxylate (Intermediate 24; 50 mg, 0.09 mmol) in DMF (5 mL) and the reaction mixture was stirred at rt for 4 h. The reaction mixture was diluted with water and extracted with EtOAc. The combined organic layers were washed with brine, dried over Na$_2$SO$_4$, filtered, and concentrated. The resulting residue was purified by FCC (25% EtOAc in hexanes) to obtain the title compound. MS (ESI+) m/z 635.2 (M+H).

Example 14. (S)-1-(6-(3-(4-(1-(Cyclopropanecarbonyl)piperidin-4-yl)-3-ethylphenoxy)-2,3-dihydro-1H-inden-4-yl)pyridin-2-yl)-5-methoxy-1H-pyrazole-4-carboxylic acid

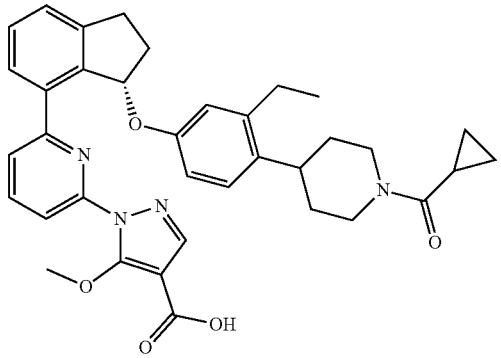 [SMILES: CCc1cc(O[C@H]2CCc3cccc(-c4cccc(-n5ncc(C(=O)O)c5OC)n4)c32)ccc1C1CCN(C(=O)C2CC2)CC1]

Lithium hydroxide (21 mg, 0.51 mmol) was added to a solution of ethyl (S)-1-(6-(3-(4-(1-(cyclopropanecarbonyl)piperidin-4-yl)-3-ethylphenoxy)-2,3-dihydro-1H-inden-4-yl)pyridin-2-yl)-5-methoxy-1H-pyrazole-4-carboxylate (Example 2-1; 650 mg, 0.10 mmol) in 1:1:1 THF:MeOH:water (6.0 mL) and the reaction mixture was heated to 65° C. for 5 h. The reaction mixture was cooled to rt and concentrated. The residue was made acidic with 1N aq. HCl and the resulting solid was collected by filtration to afford the title compound without the need for further purification. $^1$H NMR (400 MHz, METHANOL-$d_4$) δ 7.85-7.94 (m, 2H), 7.69 (d, J=7.7 Hz, 1H), 7.61 (d, J=7.2 Hz, 1H), 7.51 (d, J=7.8 Hz, 1H), 7.39-7.49 (m, 2H), 6.89 (d, J=8.6 Hz, 1H), 6.47-6.55 (m, 2H), 6.45 (d, J=2.6 Hz, 1H), 4.59-4.70 (m, 1H), 4.40-4.50 (m, 1H), 3.94 (br. d, J=9.2 Hz, 3H), 3.14-3.27 (m, 2H), 2.89-3.04 (m, 2H), 2.67-2.78 (m, 1H), 2.43-2.61 (m, 3H), 2.13-2.23 (m, 1H), 1.96-2.06 (m, 1H), 1.46-1.83 (m, 4H), 1.11 (t, J=7.6 Hz, 3H), 0.77-0.95 (m, 4H). HRMS calcd. for $C_{36}H_{39}N_4O_5$ (M+H)$^+$ 607.2920, found 607.2922.

Example 15

Example 15-1. Ethyl 1-(6-((S)-3-(3-Ethyl-4-(1-((S)-2-hydroxypropanoyl)piperidin-4-yl)phenoxy)-2,3-dihydro-1H-inden-4-yl)pyridin-2-yl)-5-methoxy-1H-pyrazole-4-carboxylate

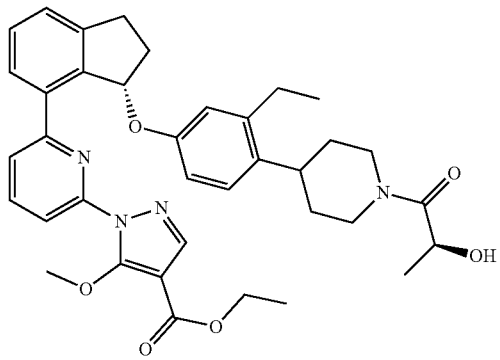 [SMILES: CCOC(=O)c1cnn(-c2cccc(-c3cccc4c3[C@@H](Oc3ccc(C5CCN(C(=O)[C@H](C)O)CC5)c(CC)c3)CC4)n2)c1OC]

The title compound was prepared using a procedure similar to that described in Example 2-1, starting from ethyl (S)-1-(6-(3-(3-ethyl-4-(piperidin-4-yl)phenoxy)-2,3-dihydro-1H-inden-4-yl)pyridin-2-yl)-5-methoxy-1H-pyrazole-4-carboxylate (Intermediate 24) and L-(+)-lactic acid. The resulting residue was purified by FCC (25% EtOAc in hexanes) to obtain the title compound. MS (ESI+) m/z 639.0 (M+H).

Example 15. 1-(6-((S)-3-(3-Ethyl-4-(1-((S)-2-hydroxypropanoyl)piperidin-4-yl)phenoxy)-2,3-dihydro-1H-inden-4-yl)pyridin-2-yl)-5-methoxy-1H-pyrazole-4-carboxylic acid

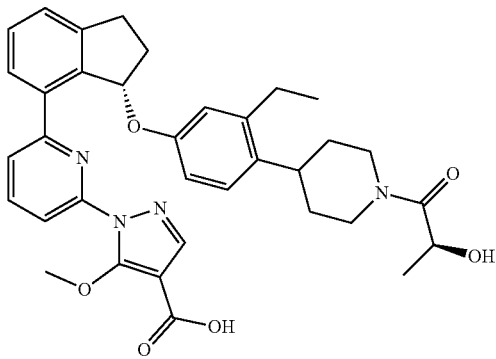 [SMILES: CCc1cc(O[C@H]2CCc3cccc(-c4cccc(-n5ncc(C(=O)O)c5OC)n4)c32)ccc1C1CCN(C(=O)[C@H](C)O)CC1]

Saponification of ethyl 1-(6-((S)-3-(3-ethyl-4-(1-((S)-2-hydroxypropanoyl)piperidin-4-yl)phenoxy)-2,3-dihydro-1H-inden-4-yl)pyridin-2-yl)-5-methoxy-1H-pyrazole-4-carboxylate (Example 15-1) as described for Example 14 afforded the title compound without the need for further purification. $^1$H NMR (400 MHz, METHANOL-$d_4$) δ 7.88-7.93 (m, 1H), 7.87 (s, 1H), 7.70 (d, J=7.6 Hz, 1H), 7.61 (d, J=7.3 Hz, 1H), 7.51 (dd, J=0.6, 8.1 Hz, 1H), 7.44-7.49 (m, 1H), 7.39-7.44 (m, 1H), 6.88 (d, J=8.6 Hz, 1H), 6.47-6.55 (m, 2H), 6.45 (d, J=2.8 Hz, 1H), 4.57-4.69 (m, 2H), 4.05-4.16 (m, 1H), 3.95 (d, J=4.0 Hz, 3H), 3.14-3.26 (m, 2H), 2.88-3.04 (m, 2H), 2.69-2.80 (m, 1H), 2.44-2.60 (m, 3H), 2.12-2.22 (m, 1H), 1.68-1.80 (m, 2H), 1.43-1.67 (m, 2H), 1.30-1.40 (m, 3H), 1.10 (t, J=7.5 Hz, 3H). HRMS calcd. for $C_{35}H_{39}N_4O_6$ (M+H)$^+$ 611.2870, found 611.2869.

Example 16

Example 16-1. Ethyl 1-(6-(3-((1'-(cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate

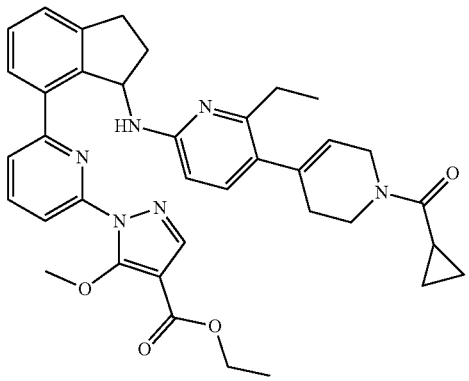 [SMILES: CCOC(=O)c1cnn(-c2cccc(-c3cccc4c3C(Nc3ccc(C5=CCN(C(=O)C6CC6)CC5)c(CC)n3)CC4)n2)c1OC]

Cyclopropanecarboxylic acid (73 mg, 0.84 mmol), HATU (426 mg, 1.12 mmol), and DIPEA (0.98 mL, 5.60 mmol) were added sequentially to a solution of Intermediate 25 (380 mg, 0.56 mmol) in DMF (10 mL) and the reaction mixture was stirred at rt for 18 h. The reaction mixture was diluted with water and extracted with diethyl ether. The combined organic layers were washed with brine, dried over $Na_2SO_4$, filtered, and concentrated. The resulting residue was purified by FCC (30-35% EtOAc in hexanes) to obtain the title compound. MS (ESI+) m/z 633.3 (M+H).

Example 16-2. (enantiomer-1)-Ethyl 1-(6-(3-((1'-(cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate and (enantiomer-2)-ethyl 1-(6-(3-((1'-(cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate Resolution of the enantiomers of ethyl 1-(6-(3-((1'-(cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate was achieved by chiral HPLC using CHIRALPAK® IC column with isocratic 40:30:30 (n-hexane [0.1% DEA]):(EtOH):(IPA:DCM[80:20]) to give (enantiomer-1)-ethyl 1-(6-(3-((1'-(cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate ($t_r$=11.90 min) and (enantiomer-2)-ethyl 1-(6-(3-((1'-(cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate ($t_r$=14.66 min).

Example 16A. (+)-1-(6-(3-((1'-(Cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylic acid

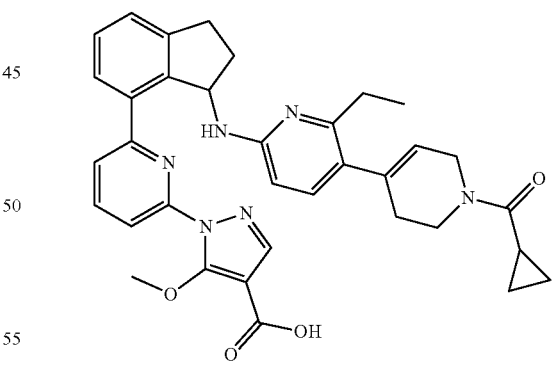

Saponification of (enantiomer-2)-ethyl 1-(6-(3-((1'-(cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate (Example 16-2; $t_r$=14.66 min) as described in Example 14 afforded the title compound without need for further purification. $^1$H NMR (400 MHz, METHANOL-$d_4$) δ 7.81-7.92 (m, 2H), 7.71 (d, J=7.2 Hz, 1H), 7.59 (dd, J=2.3, 6.4 Hz, 1H), 7.38-7.50 (m, 3H), 7.10 (br d, J=8.6 Hz, 1H), 6.26 (br d, J=8.6 Hz, 1H), 5.90 (dd, J=3.9, 7.15 Hz, 1H), 5.65-5.60 (m, 1H), 4.34-4.44 (m, 1H), 4.10-4.19 (m, 1H), 4.04 (s, 3H), 3.91-4.00 (m, 1H), 3.74-3.84 (m, 1H), 3.14-3.24 (m, 1H), 2.91-3.03 (m, 1H), 2.46-2.58 (m, 3H), 2.42 (br s, 1H), 2.29 (br s, 1H), 1.92-2.13 (m, 2H), 1.11 (t, J=7.6 Hz, 3H), 0.79-0.97 (m, 4H). HRMS calcd. for $C_{35}H_{37}N_6O_4$ (M+H)$^+$ 605.2876, found 605.2882.

Example 16B. (−)-1-(6-(3-((1'-(Cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylic acid Saponification of (enantiomer-1)-ethyl 1-(6-(3-((1'-(cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate (Example 16-2; $t_r$=11.90 min) as described in Example 14 afforded the title compound without the need for further purificaiton. $^1$H NMR and HRMS data were substantially identical to Example 16A.

Example 17

Example 17-1. Ethyl 1-(6-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate

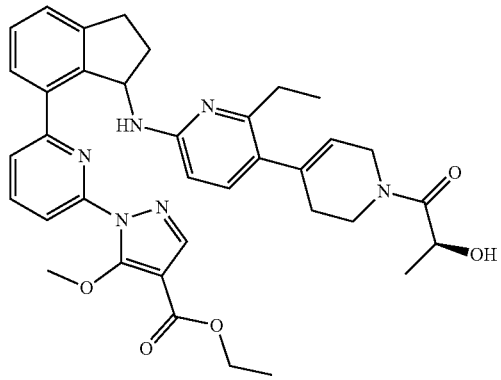 [SMILES: CCOC(=O)c1cnn(-c2cccc(-c3cccc4c3C(Nc3ccc(C5=CCN(C(=O)[C@H](C)O)CC5)c(CC)n3)CC4)n2)c1OC]

L-(+)-lactic acid (33 mg, 0.37 mmol), HATU (210 mg, 0.55 mmol), and DIPEA (0.65 mL, 3.69 mmol) were added sequentially to a solution of Intermediate 25 (250 mg, 0.37 mmol) in DMF (10 mL) and the reaction mixture was stirred at rt for 18 h. The reaction mixture was diluted with water and extracted with EtOAc. The combined organic layers were washed with brine, dried over $Na_2SO_4$, filtered, and concentrated. The resulting residue was purified by FCC (70-100% EtOAc in hexanes) to obtain the title compound. MS (ESI+) m/z 637.4 (M+H).

Example 17-2. (diastereomer 1)-Ethyl 1-(6-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate and (diastereomer 2)-ethyl 1-(6-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate Resolution of the diasteremoers of ethyl 1-(6-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate was achieved by chiral HPLC using CHIRALPAK® IA column with isocratic 80:20 (n-hexane [0.1% DEA]):(IPA:DCM[80:20]) to give (diastereomer 1)-ethyl 1-(6-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate ($t_r$=12.51 min) and (diastereomer 2)-ethyl 1-(6-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate ($t_r$=17.27 min).

Example 17A. 1-(6-((R or S)-3-((2-ethyl-1'-((S)-2-hydroxypropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylic acid

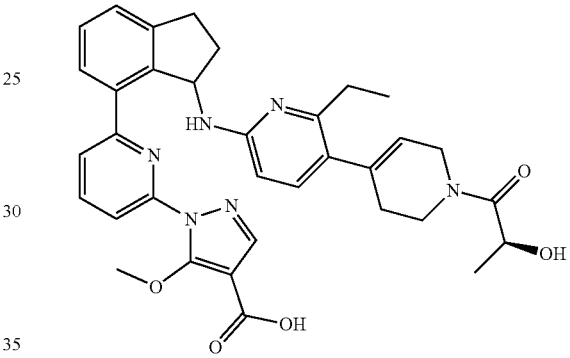

Saponification of (diastereomer 1)-ethyl 1-(6-(3-((2-ethyl-1'-((S)-2-hydroxypropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate (Example 17-2; $t_r$=12.51 min) as described in Example 14 afforded the title compound without the need for further purificaiton. $^1$H NMR (400 MHz, METHANOL-$d_4$) δ 7.89 (dd, J=7.8, 8.0 Hz, 1H), 7.83 (s, 1H), 7.72 (d, J=7.8 Hz, 1H), 7.60 (dd, J=2.0, 6.5 Hz, 1H), 7.40-7.51 (m, 3H), 7.11 (dd, J=3.5, 8.6 Hz, 1H), 6.29 (br d, J=8.6 Hz, 1H), 5.89 (dd, J=3.4, 7.1 Hz, 1H), 5.60-5.66 (m, 1H), 4.59-4.69 (m, 1H), 4.06-4.32 (m, 2H), 4.04 (s, 3H), 3.67-3.93 (m, 2H), 3.14-3.23 (m, 1H), 2.93-3.03 (m, 1H), 2.46-2.60 (m, 3H), 2.27-2.44 (m, 2H), 2.02-2.13 (m, 1H), 1.32-1.42 (m, 3H), 1.11 (t, J=7.5 Hz, 3H). HRMS calcd. for $C_{34}H_{37}N_6O_5$ (M+H)$^+$ 609.2825, found 609.2859.

Example 17B. 1-(6-((S or R)-3-((2-ethyl-1'-((S)-2-hydroxypropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylic acid Saponification of (diastereomer 2)-ethyl 1-(6-(3-((2-ethyl-1'-((S)-2-hydroxpropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylate (Example 17-2; $t_r$=17.27 min) as described in Example 14 afforded the title compound without the need for further purification. $^1$H NMR (400 MHz, METHANOL-d₄) δ 7.88 (dd, J=7.8, 8.0 Hz, 1H), 7.83 (s, 1H), 7.71 (d, J=7.7 Hz, 1H), 7.60 (dd, J=2.0, 6.5 Hz, 1H), 7.38-7.50 (m, 3H), 7.07-7.15 (m, 1H), 6.28 (br d, J=8.6 Hz, 1H), 5.89 (dd, J=3.7, 7.0 Hz, 1H), 5.62 (br s, 1H), 4.58-4.69 (m, 1H), 4.06-4.31 (m, 2H), 4.04 (s, 3H), 3.70-3.90 (m, 2H), 3.15-3.23 (m, 1H), 2.91-3.03 (m, 1H), 2.46-2.59 (m, 3H), 2.27-2.42 (m, 2H), 2.02-2.14 (m, 1H), 1.32-1.40 (m, 3H), 1.11 (t, J=7.5 Hz, 3H). HRMS calcd. for $C_{34}H_{37}N_6O_5$ (M+H)⁺ 609.2825, found 609.2845.

Example 18

Example 18-1. Ethyl 5-amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylate

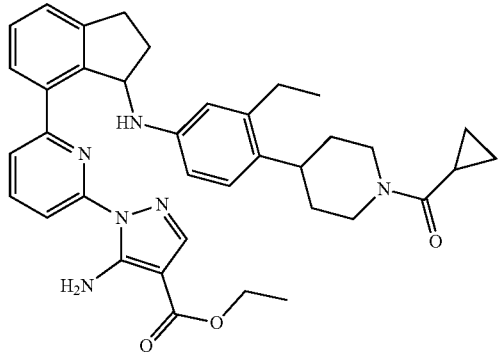 [SMILES: CCOC(=O)c1cnn(-c2cccc(-c3cccc4c3C(Nc3ccc(C5CCN(C(=O)C6CC6)CC5)c(CC)c3)CC4)n2)c1N]

Pd(dppf)Cl₂·CH₂Cl₂ adduct (35 mg, 0.04 mmol) was added to a mixture of Intermediate 12 (200 mg, 0.43 mmol), bis(pinacolato)diboron (116 mg, 0.46 mmol), and KOAc (58 mg, 0.06 mmol) in dioxane (10 mL). The reaction mixture was heated to 100° C. for 16 h. The reaction mixture was cooled to rt and Intermediate 22 (92 mg, 0.30 mmol) was added, followed by 2M aq. K₃PO₄ (0.65 mL, 1.3 mmol) and Pd(dppf)Cl₂·CH₂Cl₂ adduct (35 mg, 0.04 mmol). The reaction mixture was heated to 100° C. for another 4 h. The reaction mixture was cooled and concentrated. The residue was partitioned between EtOAc and water. The organic layer was isolated, dried over Na₂SO₄, filtered, and concentrated. The resulting residue was purified by FCC (50% EtOAc in hexanes) to obtain the title compound. MS (ESI+) m/z 619.3 (M+H).

Example 18-2. (enantiomer-1)-Ethyl 5-amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylate and (enantiomer-2)-ethyl 5-amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylate Resolution of the enantiomers of ethyl 5-amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylate was achieved by chiral HPLC using CHIRALPAK® IA column with isocratic 60:40 (0.1% DEA in n-hexane):(IPA:DCM [90:10]) to give (enantiomer-1)-ethyl 5-amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylate (t_r=5.14 min) and (enantiomer-2)-ethyl 5-amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylate (t_r=15.13 min).

Example 18A. (+)-5-Amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylic acid

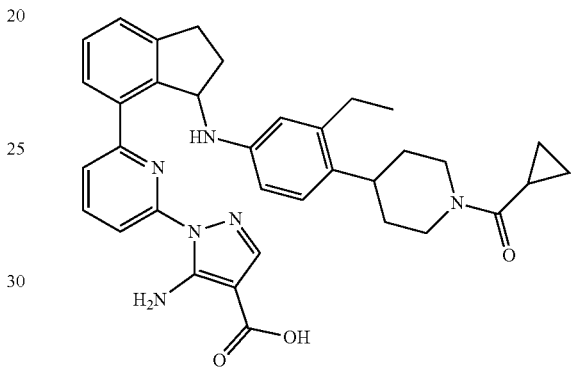

Saponification of (enantiomer-2)-ethyl 5-amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylate (Example 18-2; t_r=15.13 min) as described in Example 14 afforded the title compound without the need for further purification. ¹H NMR (400 MHz, METHANOL-d₄) δ 7.79-7.85 (m, 1H), 7.65-7.69 (m, 2H), 7.53 (dd, J=0.8, 7.6 Hz, 1H), 7.41-7.47 (m, 1H), 7.37-7.41 (m, 2H), 6.72 (d, J=8.4 Hz, 1H), 6.25 (d, J=4.9 Hz, 2H), 5.33 (dd, J=3.7, 6.9 Hz, 1H), 4.62 (br.d, J=12.5 Hz, 1H), 4.43 (br.d, J=13.1 Hz, 1H), 3.14-3.27 (m, 2H), 2.81-2.98 (m, 2H), 2.65-2.76 (m, 1H), 2.36-2.53 (m, 3H), 2.05-2.15 (m, 1H), 1.95-2.04 (m, 1H), 1.41-1.82 (m, 4H), 1.07 (t, J=7.6 Hz, 3H), 0.75-0.94 (m, 4H). HRMS calcd. for $C_{35}H_{39}N_6O_3$ (M+H)⁺ 591.3084, found 591.3082.

Example 18B. (−)-5-Amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylic acid Saponification of (enantiomer-1)-ethyl 5-amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylate (Example 18-2; t_r=5.14 min) as described in Example 14 afforded the title compound without the need for further purification. The NMR and HRMS data are substantially identical to Example 18A.

Example 19

Example 19-1. Ethyl (S)-5-amino-1-(6-(3-(4-(1-(cyclopropanecarbonyl)piperidin-4-yl)-3-ethylphenoxy)-2,3-dihydro-1H-inden-4-yl)pyridin-2-yl)-1H-pyrazole-4-carboxylate

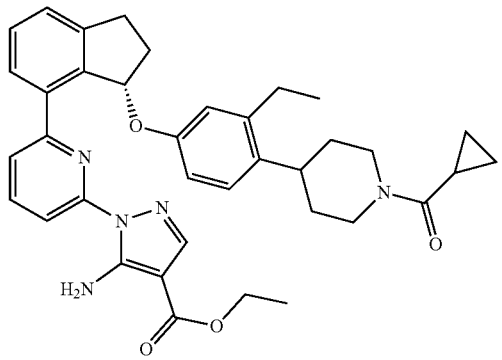 [SMILES: CCOC(=O)c1cnn(-c2cccc(-c3cccc4c3[C@@H](Oc3ccc(C5CCN(C(=O)C6CC6)CC5)c(CC)c3)CC4)n2)c1N]

The title compound was prepared as described for Example 9-1 starting from (S)-(4-(4-((7-bromo-2,3-dihydro-1H-inden-1-yl)oxy)-2-ethylphenyl)piperidin-1-yl)(cyclopropyl)methanone (Intermediate 13) and Intermediate 22. The resulting residue was purified by FCC (50% EtOAc in hexanes) to obtain the title compound. MS (ESI+) m/z 620.3 (M+H).

Example 19. (S)-5-Amino-1-(6-(3-(4-(1-(cyclopropanecarbonyl)piperidin-4-yl)-3-ethylphenoxy)-2,3-dihydro-1H-inden-4-yl)pyridin-2-yl)-1H-pyrazole-4-carboxylic acid

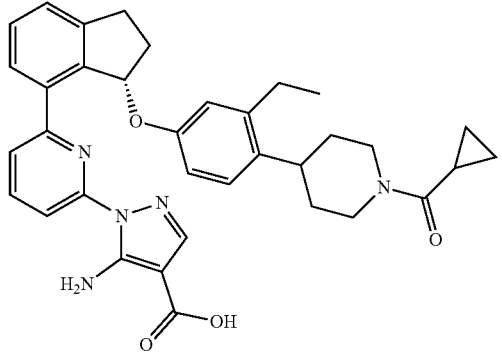 [SMILES: CCc1cc(O[C@H]2CCc3cccc(-c4cccc(-n5ncc(C(=O)O)c5N)n4)c32)ccc1C1CCN(C(=O)C2CC2)CC1]

Saponification of ethyl (S)-5-amino-1-(6-(3-(4-(1-(cyclopropanecarbonyl)piperidin-4-yl)-3-ethylphenoxy)-2,3-dihydro-1H-inden-4-yl)pyridin-2-yl)-1H-pyrazole-4-carboxylate (Example 19-1) as described in Example 14, followed by purification by FCC (3% MeOH in DCM) afforded the title compound. $^1$H NMR (400 MHz, METHANOL-$d_4$) δ 7.89 (dd, J=7.7, 8.3 Hz, 1H), 7.70 (dd, J=0.7, 8.4 Hz, 1H), 7.63 (s, 1H), 7.39-7.52 (m, 4H), 6.86 (d, J=8.7 Hz, 1H), 6.35-6.51 (m, 2H), 6.23 (dd, J=3.9, 6.5 Hz, 1H), 4.64 (br d, J=12.5 Hz, 1H), 4.44 (br d, J=12.7 Hz, 1H), 3.16-3.29 (m, 2H), 2.97-3.06 (m, 1H), 2.86-2.96 (m, 1H), 2.66-2.77 (m, 1H), 2.56-2.66 (m, 1H), 2.52 (q, J=7.5 Hz, 2H), 2.13-2.22 (m, 1H), 1.96-2.04 (m, 1H), 1.41-1.82 (m, 4H), 1.09 (t, J=7.5 Hz, 3H), 0.76-0.95 (m, 4H). HRMS calcd. for $C_{35}H_{38}N_5O_4$ (M+H)$^+$ 592.2924, found 592.2922.

Example 20

Example 20-1. Ethyl (R)-5-amino-1-(3-(3-(4-(1-(cyclopropanecarbonyl)piperidin-4-yl)-3-ethylbenzyl)-2,3-dihydro-1H-inden-4-yl)phenyl)-1H-pyrazole-4-carboxylate

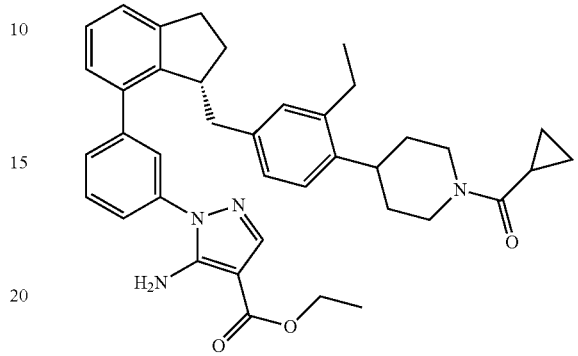

Cyclopropanecarboxylic acid (12 mg, 0.15 mmol), HATU (77 mg, 0.20 mmol), and DIPEA (0.24 mL, 1.35 mmol) were added sequentially to Intermediate 26 (74 mg, 0.135 mmol) in DMF (10 mL) at rt. The reaction mixture was stirred at rt for 3 h. The reaction mixture was diluted with water, resulting in the formation of a precipitate. The precipitate was collected by vacuum filtration, and then purified by FCC (neutral aluminum oxide stationary phase, 50% EtOAc in hexanes mobile phase) to obtain the title compound. MS (ESI+) m/z 617.4 (M+H).

Example 20. (+)-(R)-5-Amino-1-(3-(3-(4-(1-(cyclopropanecarbonyl)piperidin-4-yl)-3-ethylbenzyl)-2,3-dihydro-1H-inden-4-yl)phenyl)-1H-pyrazole-4-carboxylic acid

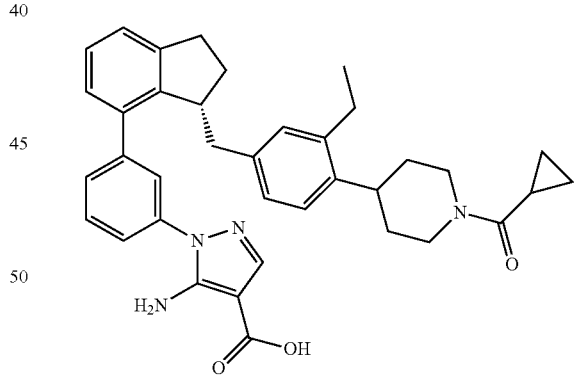

LiOH.H$_2$O (20 mg, 0.49 mmol) was added to a solution of Example 20-1 (60 mg, 0.10 mmol) in 1:1:1 MeOH:THF: water (10 mL). The reaction mixture was heated to 70° C. for 24 h. The reaction mixture was concentrated and redissolved in water. The mixture was made acidic by adding citric acid, resulting in a precipitate. The precipitate was collected by vacuum filtration and collected solid was purified by FCC (neutral aluminum oxide stationary phase (5% MeOH in DCM mobile phase) to obtain the title compound. $^1$H NMR (400 MHz, Methanol-$d_4$) δ 7.77 (s, 1H), 7.70-7.63 (m, 2H), 7.60-7.55 (m, 2H), 7.28-7.22 (m, 1H), 7.22-7.17 (m, 2H), 6.95 (d, J=7.9 Hz, 1H), 6.68 (d, J=8.0 Hz, 1H), 6.61 (s, 1H), 4.64 (d, J=12.0 Hz, 1H), 4.44 (d, J=14.1 Hz, 1H), 3.90-3.82 (m, 1H), 3.27-3.19 (m, 1H), 3.06-2.95 (m, 1H), 2.88-2.81 (m, 2H), 2.73 (t, J=12.2 Hz, 1H), 2.58 (q, J=7.5 Hz, 2H), 2.46 (dd, J=13.4, 3.8 Hz, 1H), 2.20 (dd, J=13.4, 9.7 Hz, 1H), 2.15-2.04 (m, 1H), 2.04-1.95 (m, 1H), 1.95-1.86 (m, 1H), 1.77 (d, J=12.2 Hz, 1H), 1.74-1.46 (m, 3H), 1.10 (t, J=7.5 Hz, 3H), 0.94-0.85 (m, 2H), 0.85-0.76 (m, 2H). HRMS calcd. for $C_{37}H_{41}N_4O_3$ $(M+H)^+$ 589.3178, found 589.3181.

Example 21

Example 21-1. Ethyl (R)-1-(3-(3-(4-(1-(cyclopropanecarbonyl)piperidin-4-yl)-3-ethylbenzyl)-2,3-dihydro-1H-inden-4-yl)phenyl)-5-(methylamino)-1H-pyrazole-4-carboxylate

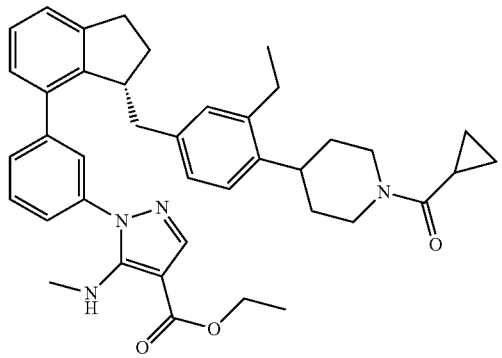 [SMILES: CCOC(=O)c1cnn(-c2cccc(-c3cccc4c3[C@@H](Cc3ccc(C5CCN(C(=O)C6CC6)CC5)c(CC)c3)CC4)c2)c1NC]

The title compound was synthesized by Boc deprotection as described for Intermediate 26, followed by an amide coupling as described in Example 20-1, starting with tert-butyl (R)-4-(4-((7-(3-(4-(ethoxycarbonyl)-5-(methylamino)-1H-pyrazol-1-yl)phenyl)-2,3-dihydro-1H-inden-1-yl)methyl)-2-ethylphenyl)piperidine-1-carboxylate (Intermediate 27). MS (ESI+) m/z 631.4 (M+H).

Example 21. (R)-1-(3-(3-(4-(1-(cyclopropanecarbonyl)piperidin-4-yl)-3-ethylbenzyl)-2,3-dihydro-1H-inden-4-yl)phenyl)-5-(methylamino)-1H-pyrazole-4-carboxylic acid

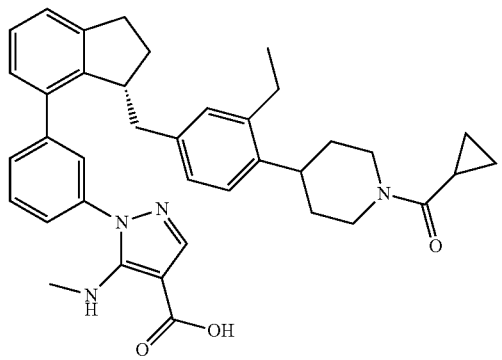 [SMILES: CCc1cc(C[C@H]2CCc3cccc(-c4cccc(-n5ncc(C(=O)O)c5NC)c4)c32)ccc1C1CCN(C(=O)C2CC2)CC1]

The title compound was saponofied as described for Example 20, starting with Example 21-1, and was purified by FCC (neutral aluminum oxide stationary phase (5% MeOH in DCM mobile phase) to obtain the title compound. $^1$H NMR (400 MHz, METHANOL-$d_4$) δ 7.79 (s, 1H), 7.53-7.69 (m, 4H), 7.18-7.31 (m, 2H), 7.15 (dd, J=1.2, 7.3 Hz, 1H), 6.96 (d, J=8.0 Hz, 1H), 6.68 (dd, J=1.7, 7.8 Hz, 1H), 6.60 (s, 1H), 4.58-4.71 (m, 1H), 4.40-4.51 (m, 1H), 3.77-3.91 (m, 1H), 3.20-3.29 (m, 1H), 2.95-3.09 (m, 1H), 2.79-2.87 (m, 2H), 2.68-2.78 (m, 1H), 2.51-2.64 (m, 5H), 2.45 (dd, J=3.7, 13.5 Hz, 1H), 2.15-2.26 (m, 1H), 1.95-2.14 (m, 2H), 1.84-1.94 (m, 1H), 1.47-1.83 (m, 4H), 1.11 (t, J=7.6 Hz, 3H), 0.76-0.98 (m, 4H). HRMS calcd. for $C_{38}H_{43}N_4O_3$ $(M+H)^+$ 603.3335, found 603.3336.

Example 22

Example 22-1. Ethyl 1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-(methylamino)-1H-pyrazole-4-carboxylate

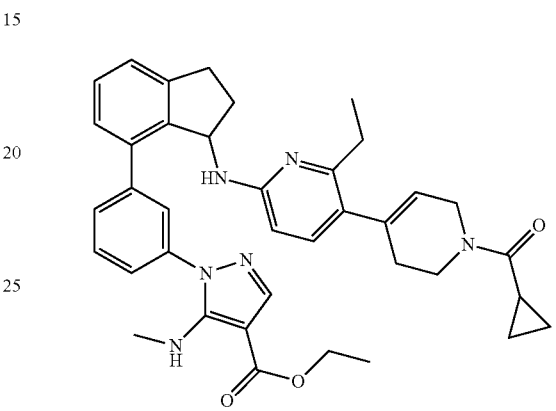

Pd(dppf)Cl$_2$·CH$_2$Cl$_2$ (57 mg, 0.07 mmol) was added to a mixture of Intermediate 4 (226 mg, 0.70 mmol), bis(pinacolato)diboron (204 mg, 0.80 mmol), and KOAc (158 mg, 1.61 mmol) in dioxane (3 mL) and the reaction mixture was stirred at 100° C. for 1 h. The reaction mixture was cooled to rt and Intermediate 29 (250 mg, 0.54 mmol) in dioxane (3 mL) was added, followed by K$_3$PO$_4$ (341 mg, 1.61 mmol), water (3 mL), and Pd(dppf)Cl$_2$·CH$_2$Cl$_2$ (57 mg, 0.07 mmol). The reaction mixture was again heated to 100° C. for 2 h. The reaction mixture was cooled, partitioned between EtOAc and water, and the aqueous layer was extracted with EtOAc. The combined the organic layers were concentrated and the residue was purified by FCC (0-40% EtOAc in DCM) to give the title compound. MS (ESI+) m/z 631.6 (M+H).

Example 22-2. 1-(3-(3-((1'-(Cyclopropanecarbonyl)-2-ethyl-1',2',3',6'-tetrahydro-[3,4'-bipyridin]-6-yl)amino)-2,3-dihydro-1H-inden-4-yl)phenyl)-5-(methylamino)-1H-pyrazole-4-carboxylic acid

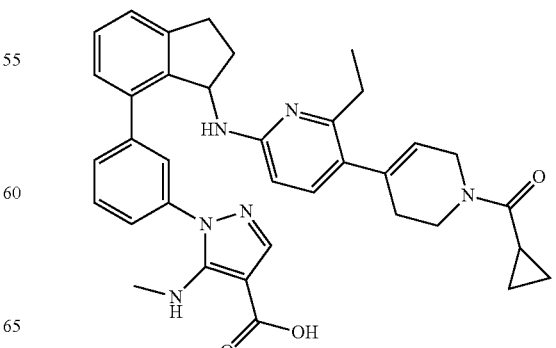

1M aq Lithium hydroxide (2.07 mL, 2.07 mmol) was added to a solution of Example 22-1 (290 mg, 0.46 mmol) in methanol (4 mL) and THF (2 mL). The reaction mixture was stirred at 50° C. for 16 h. The reaction mixture was cooled to rt and 1N aq HCl (2 mL) was added and resulting heterogeneous mixture was extracted with EtOAc. The combined the organic layers were concentrated and the residue was purified by RP-HPLC (stationary phase: Gemini® NX 5μ C18 110A 100×30 mm; mobile phase: gradient, water with 0.1% (28% ammonium hydroxide)/acetonitrile). The pooled and dried HPLC residue was further purified by recrystallization from ACN to give the title compound. MS (ESI+) m/z 603.4 (M+H).

Example 22-3. (−)-1-(3-(3-((1'-(Cyclopropanecarbonyl)-2-ethyl-1',2',3',6'-tetrahydro-[3,4'-bipyridin]-6-yl)amino)-2,3-dihydro-1H-inden-4-yl)phenyl)-5-(methylamino)-1H-pyrazole-4-carboxylic acid and (+)-1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-(methylamino)-1H-pyrazole-4-carboxylic acid Resolution of the enantiomers of 1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-(methylamino)-1H-pyrazole-4-carboxylic acid was achieved by chiral SFC using CHIRALPAK® IA column with a 5-55% (5 mM NH₄OH in MeOH) gradient in CO₂ to give (−)-1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-(methylamino)-1H-pyrazole-4-carboxylic acid ($t_r$=3.80 min) and (+)-1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-(methylamino)-1H-pyrazole-4-carboxylic acid ($t_r$=5.15 min).

Example 22A. (+)-1-(3-(3-((1'-(Cyclopropanecarbonyl)-2-ethyl-1',2',3',6'-tetrahydro-[3,4'-bipyridin]-6-yl)amino)-2,3-dihydro-1H-inden-4-yl)phenyl)-5-(methylamino)-1H-pyrazole-4-carboxylic acid

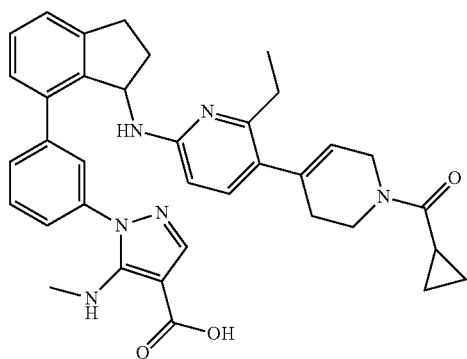 [SMILES: CCc1nc(NC2CCc3cccc(-c4cccc(-n5ncc(C(=O)O)c5NC)c4)c32)ccc1C1=CCN(C(=O)C2CC2)CC1]

(+)-1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-(methylamino)-1H-pyrazole-4-carboxylic acid ($t_r$=5.15 min; Example 22-3). ¹H NMR (400 MHz, Methanol-d₄) δ 7.75 (t, J=1.7 Hz, 1H), 7.65 (s, 1H), 7.54 (dt, J=7.5, 1.5 Hz, 1H), 7.43 (t, J=7.7 Hz, 1H), 7.40-7.32 (m, 3H), 7.29-7.25 (m, 1H), 7.09 (d, J=8.5 Hz, 1H), 6.21 (d, J=8.5 Hz, 1H), 5.60 (d, J=11.4 Hz, 1H), 5.48 (dd, J=6.5, 2.9 Hz, 1H), 4.41-4.35 (m, 1H), 4.17-4.12 (m, 1H), 3.94 (t, J=5.4 Hz, 1H), 3.78 (t, J=5.3 Hz, 1H), 3.20 (dt, J=15.9, 7.9 Hz, 1H), 2.93 (ddd, J=15.9, 8.4, 3.9 Hz, 1H), 2.61-2.49 (m, 2H), 2.45-2.36 (m, 2H), 2.34 (s, 3H), 2.32-2.26 (m, 1H), 2.11-1.92 (m, 2H), 1.13 (t, J=7.5 Hz, 3H), 0.95-0.89 (m, 2H), 0.88-0.82 (m, 2H). HRMS calcd for $C_{36}H_{39}N_6O_3$ (M+H)⁺ 603.3083, found 603.3113.

Example 22B. (−)-1-(3-(3-((1'-(Cyclopropanecarbonyl)-2-ethyl-1',2',3',6'-tetrahydro-[3,4'-bipyridin]-6-yl)amino)-2,3-dihydro-1H-inden-4-yl)phenyl)-5-(methylamino)-1H-pyrazole-4-carboxylic acid (−)-1-(3-(3-((1'-(cyclopropanecarbonyl)-2-ethyl-1',2',3', 6'-tetrahydro-[3,4'-bipyridin]-6-yl)amino)-2,3-dihydro-1H-inden-4-yl)phenyl)-5-(methylamino)-1H-pyrazole-4-carboxylic acid ($t_r$=3.80 min; Example 22-3). ¹H NMR and HRMS were substantially identical to Example 22A.

Example 23

Example 23-1. Ethyl (R)-5-amino-1-(6-(3-(4-(1-(cyclopropanecarbonyl)piperidin-4-yl)-3-ethylbenzyl)-2,3-dihydro-1H-inden-4-yl)pyridin-2-yl)-1H-pyrazole-4-carboxylate

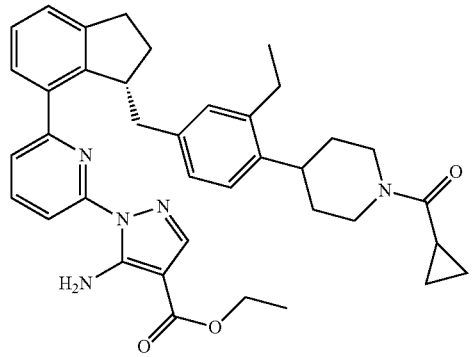 [SMILES: CCOC(=O)c1cnn(-c2cccc(-c3cccc4c3[C@@H](Cc3ccc(C5CCN(C(=O)C6CC6)CC5)c(CC)c3)CC4)n2)c1N]

The title compound was prepared as described for Example 20-1, starting with Intermediate 28 and cyclopropylcarboxylic acid. MS (ESI+) m/z 640.3 (M+Na).

Example 23. (R)-5-Amino-1-(6-(3-(4-(1-(cyclopropanecarbonyl)piperidin-4-yl)-3-ethylbenzyl)-2,3-dihydro-1H-inden-4-yl)pyridin-2-yl)-1H-pyrazole-4-carboxylic acid

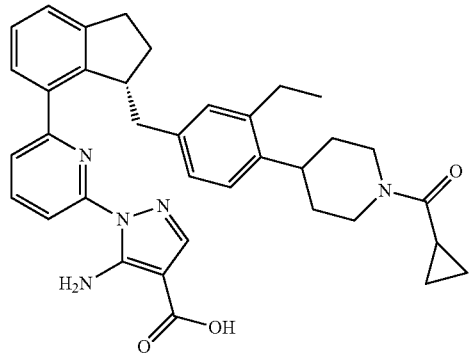 [SMILES: CCc1cc(C[C@H]2CCc3cccc(-c4cccc(-n5ncc(C(=O)O)c5N)n4)c32)ccc1C1CCN(C(=O)C2CC2)CC1]

The title compound was prepared as described for Example 20, starting with Example 23-1. $^1$H NMR (400 MHz, Methanol-d$_4$) δ 8.02-7.94 (m, 1H), 7.88-7.82 (m, 1H), 7.80 (s, 1H), 7.43 (d, J=7.5 Hz, 1H), 7.36 (dd, J=6.0, 2.8 Hz, 1H), 7.34-7.27 (m, 2H), 6.86 (d, J=6.6 Hz, 1H), 6.67-6.58 (m, 1H), 6.55 (d, J=6.3 Hz, 1H), 4.62 (d, J=12.0 Hz, 1H), 4.48-4.36 (m, 1H), 4.27-4.19 (m, 1H), 3.24-3.17 (m, 1H), 3.04-2.83 (m, 3H), 2.76-2.65 (m, 1H), 2.53-2.39 (m, 2H), 2.35 (dd, J=13.2, 5.2 Hz, 1H), 2.31-2.11 (m, 2H), 2.01-1.89 (m, 2H), 1.79-1.42 (m, 4H), 1.02 (t, J=7.5 Hz, 3H), 0.93-0.85 (m, 2H), 0.85-0.78 (m, 2H). HRMS calcd. for $C_{36}H_{40}N_5O_3$ (M+H)$^+$ 590.3131, found 590.3134.

Example 24

Example 24-1. Ethyl (R)-1-(6-(3-(3-ethyl-4-(1-((S)-2-hydroxypropanoyl)piperidin-4-yl)benzyl)-2,3-dihydro-1H-inden-4-yl)pyridin-2-yl)-5-methoxy-1H-pyrazole-4-carboxylate

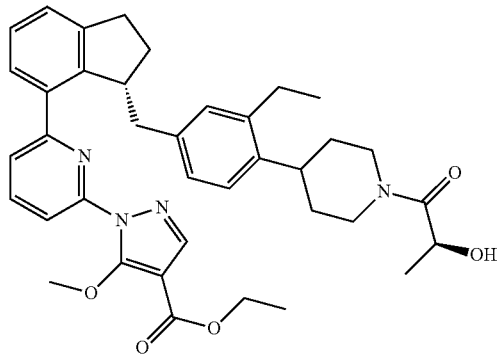 [SMILES: CCOC(=O)c1cnn(-c2cccc(-c3cccc4c3[C@@H](Cc3ccc(C5CCN(C(=O)[C@H](C)O)CC5)c(CC)c3)CC4)n2)c1OC]

The title compound was prepared as described in Example 2-1, starting with Intermediate 23 and L-(+)-lactic acid. MS (ESI+) m/z 637.3 (M+H).

Example 24. (+)-(R)-1-(6-(3-(3-Ethyl-4-(1-((S)-2-hydroxypropanoyl)piperidin-4-yl)benzyl)-2,3-dihydro-1H-inden-4-yl)pyridin-2-yl)-5-methoxy-1H-pyrazole-4-carboxylic acid

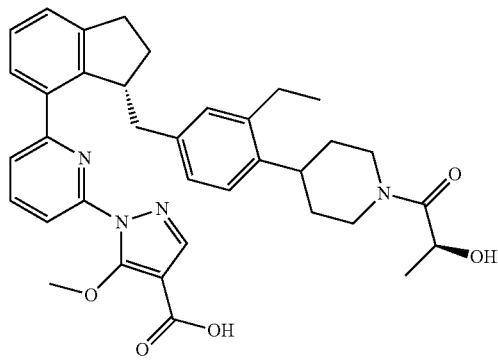 [SMILES: CCc1cc(C[C@H]2CCc3cccc(-c4cccc(-n5ncc(C(=O)O)c5OC)n4)c32)ccc1C1CCN(C(=O)[C@H](C)O)CC1]

The title compound was prepared as described in Example 2A, starting with Example 24-1. $^1$H NMR (400 MHz, Methanol-d$_4$) δ 8.03 (t, J=7.9 Hz, 1H), 7.98 (s, 1H), 7.63 (dd, J=7.9, 2.1 Hz, 2H), 7.45-7.39 (m, 1H), 7.31-7.25 (m, 2H), 6.88 (d, J=8.1 Hz, 1H), 6.64-6.58 (m, 2H), 4.69-4.56 (m, 2H), 4.40-4.31 (m, 1H), 4.17-4.06 (m, 4H), 3.23-3.14 (m, 1H), 3.04-2.89 (m, 2H), 2.87-2.70 (m, 2H), 2.58-2.45 (m, 3H), 2.24 (dd, J=13.3, 9.8 Hz, 1H), 2.13-2.01 (m, 1H), 1.94-1.86 (m, 1H), 1.80-1.50 (m, 4H), 1.35 (dd, J=19.1, 6.6 Hz, 3H), 1.07 (t, J=7.5 Hz, 3H). HRMS: calcd. for $C_{36}H_{41}N_4O_5$ (M+H)$^+$ 609.3076, found 609.3087.

Biological Example-1. CHO Cellular Assay

Chinese hamster ovary (CHO) cells overexpressing soluble guanylate cyclase were generated to test the effect of sGC activators in a cellular context. Human cDNAs for GUCYA3 (RefSeq: NM_000856.3) and GUCYB3 (RefSeq: NM_000857.1) were amplified by PCR from a HUVEC (Human Umbilical Vein Endothelial Cells) cDNA library and cloned into mammalian expression vectors. CHO K1 cells (ATCC CCL-61) were transfected using Lipofectamine 2000 following manufacturer's instructions and stably expressing clones were identified by antibiotic selection. CHO GUCY clone 8E10 was used for subsequent experiments.

Cells were seeded at a density of 3000 cells/well in white 384-well proxyplates (Perkin Elmer) and incubated overnight, then the medium was removed and cells were washed with assay buffer (HBSS, 0.1% BSA, 1 mM IBMX, 20 uM ODQ). sGC activators were serially diluted in DMSO, then diluted in assay buffer prior to adding to cells (10 ul/well, final DMSO concentration 0.5%). Cells were incubated with compounds for 1 h at room temperature, then assayed for cGMP production using Cisbio cGMP HTRF kit (62GM2PEC) according to manufacturer's instructions.

The EC50s are calculated based on the amount of cGMP interpolated from the standard curve, using a 4-parameter sigmoidal dose-response.

Compounds of invention are active on sGC activation. Data in Table 1 collected using the assay of Biological Example 1. The minimum EC$_{50}$ quantification limit of the assay is 0.0005 µM, therefore any compound listed as having an EC$_{50}$ value of ≤0.0005 µM has an actual EC$_{50}$ value equal to or below the quantification limit.

TABLE 1

| Example number | Mean EC$_{50}$ (µM) |
|---|---|
| 1A | <0.0006 |
| 1B | 0.016 |
| 2A | <0.0005 |
| 2B | 0.034 |
| 3A | <0.0005 |
| 3B | 0.029 |
| 4A | <0.0005 |
| 4B | 0.11 |
| 5 | <0.0005 |
| 6 | <0.0005 |
| 7A | <0.0005 |
| 7B | 0.002 |
| 8A | <0.0005 |
| 8B | 0.086 |
| 9A | 0.004 |
| 9B | 0.058 |
| 10A | <0.0005 |
| 10B | 0.149 |
| 11A | 0.036 |
| 11B | 0.0014 |
| 12A | 0.053 |
| 12B | <0.0005 |
| Example 13 | <0.0005 |
| Example 14 | <0.0005 |
| Example 15 | 0.001 |

TABLE 1-continued

| Example number | Mean EC$_{50}$ (µM) |
| --- | --- |
| Example 16A | <0.0005 |
| Example 16B | 0.279 |
| Example 17A | 0.071 |
| Example 17B | 0.0035 |
| Example 18A | 0.007 |
| Example 18B | 0.031 |
| Example 19 | 0.003 |
| Example 20 | <0.0005 |
| Example 21 | <0.0005 |
| Example 22A | <0.0005 |
| Example 22B | 0.0404 |
| Example 23 | <0.0005 |
| Example 24 | <0.0005 |

Biological Example-2. Measuring Pharmacokinetic Clearance in Intravenously Dosed Rats Sprague-Daley rats were administered sGC activators intravenously to assess the systemic clearance rates of the compounds from blood by non-compartmental analysis. Compounds with high clearance rates may be less prone to exert unwanted systemic (non-local) pharmocoligcal effects, which may be a benefical property for a compound intended to be dosed via topical ocular administration with the aim of exerting a pharmacological reponse locally in the eye.

In order to assess the pharmacokinetic parameters, male Sprague-Dawley rats were given 1 mL/Kg of the dosing solution (delineated in the table below) containing a test article (0.5 mg/kg) per kg of body weight via slow intravenous injection into an indwelling jugular vein catheter in a discrete PK study. Alternatively, male Sprague-Dawley rats were given 1 mL/Kg of the dosing solution containing three test articles (0.5 mg/kg each, 1.5 mg/kg total) per kg of body weight via slow intravenous injection into an indwelling jugular vein catheter in a cassette PK study. Diet and water was provided ad libitum without exception. At specified time following a single intravenous bolus injection, approximately 100 µL of whole blood was collected from indwelling catheter in jugular vein. The blood was stored frozen at −20° C. before an LC-MS/MS method was used to quantitate drug levels in the blood. All pharmacokinetic (PK) parameters were derived from concentration-time data by non-compartmental analyses using WinNonlin Phoenix version 6.4 (Certara, St. Louis, Mo.). For the intravenous dose, the concentration of unchanged compound at time 0 was calculated based on a log-linear regression of first two data points to back-extrapolate C(0). The area under the concentration-time curve was calculated using the linear trapezoidal rule.

Data in Table 2 collected using the assay of Biological Example 2 compares compounds from the present invention to other sGC activators previously disclosed PCT/IB2015/055006 filed Jul. 2, 2015 which exhibit lower clearance values than the compounds of this invention.

| Example # or comparator IUPAC name | EC50 from biological Example #1 (µM) | Mean Rat Clearance value (mL/min/Kg) | Study and Dosing Solution Type |
| --- | --- | --- | --- |
| Example 1A | <0.0006 | >100 | Discrete - A |
| Example 3A | <0.0005 | >100 | Discrete - B |
| Example 4A | <0.0005 | >100 | Discrete - C |
| Example 5 | <0.0005 | 89 | Discrete - D |
| Example 18A | 0.007 | 98 | Discrete - D |
| (+)-1-(6-(3-(4-(1-(cyclopropanecarbonyl)piperidin-4-yl)-2-methylbenzyl)-2,3-dihydro-1H-inden-4-yl)pyridin-2-yl)-5-methyl-1H-pyrazole-4-carboxylic acid | <0.0005 | 25.6<br>97.2 | Discrete - D<br>Cassette - E |
| (+)-1-(3-(3-((4-(1-(cyclopropanecarbonyl)piperidin-4-yl)-2-methylphenyl)amino)-2,3-dihydro-1H-inden-4-yl)phenyl)-5-methyl-1H-pyrazole-4-carboxylic acid | <0.0005 | 24.9 | Cassette - F |
| (+)-1-(6-(3-((4-(1-((S)-2-hydroxypropanoyl)piperidin-4-yl)-2-methylphenyl)amino)-2,3-dihydro-1H-inden-4-yl)pyridin-2-yl)-5-methyl-1H-pyrazole-4-carboxylic acid | <0.0005 | 48.3 | Cassette - E |
| (+)-1-(6-(3-((4-(1-(cyclopropanecarbonyl)-1,2,3,6-tetrahydropyridin-4-yl)-3-ethylphenyl)amino)-2,3-dihydro-1H-inden-4-yl)pyridin-2-yl)-5-ethyl-1H-pyrazole-4-carboxylic acid | <0.0005 | 38 | Discrete - D |
| (+)-1-(6-(3-(4-(1-(cyclopropanecarbonyl)piperidin-4-yl)-3-ethylphenoxy)-2,3-dihydro-1H-inden-4-yl)pyridin-2-yl)-5-ethyl-1H-pyrazole-4-carboxylic acid | <0.0005 | 14<br>6.6 | Discrete - G<br>Cassette - E |

| Dosing Solution Code | Dosing Solution |
| --- | --- |
| A | Discrete study: 10% propylene glycol, 1 molar equivalent of 1N NaOH, 25% of a 20% aqueous solution of Solutol HS15 , and qs with PBS buffer to arrive at a concentration of test article at 0.5 mg/mL |
| B | Discrete study: 20% PEG 300, 1 molar equivalent of 1N NaOH, 10% Solutol HS15 (neat), and qs with PBS buffer to arrive at a concentration of test article at 0.5 mg/mL |

| | |
|---|---|
| C | Discrete study: 20% PEG 300, 10% Solutol HS15 (neat), and qs with PBS buffer to arrive at a concentration of test article at 0.5 mg/mL |
| D | Discrete study: 10% propylene glycol, 10% Solutol HS15 (neat), and qs with PBS buffer to arrive at a concentration of test article at 0.5 mg/mL |
| E | Cassette study: 10% propylene glycol, 10% Solutol HS15 (neat), and qs with PBS buffer to arrive at a concentration of an individual test article at 0.5 mg/mL |
| F | Cassette study: 20% propylene glycol, 10% Solutol HS15 (neat), and qs with PBS buffer to arrive at a concentration of an individual test article at 0.5 mg/mL |
| G | Discrete study: 20% propylene glycol, 50% of a 20% aqueous solution of Solutol HS15, and qs with water to arrive at a concentration of test article at 0.5 mg/mL |

What is claimed is:

1. A compound according to Formula (I):

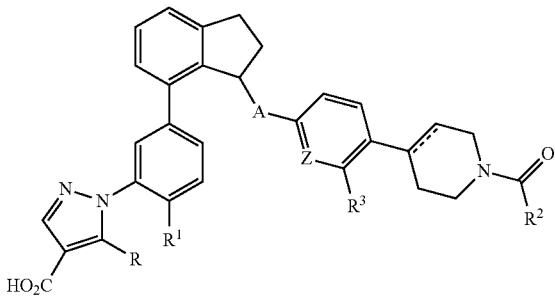

or a pharmaceutically acceptable salt thereof, wherein
X is CH or N;
⌇ is a single bond or a double bond;
A is $CH_2$, O or N(H);
Z is $CR^4$ or N with the proviso that A is not O when Z is N;
When X is CH then R is $C_1$-$C_4$alkoxy, amino, $C_1$-$C_4$alkylamino or di-$C_1$-$C_4$alkylamino; or
When X is N then R is $C_1$-$C_4$alkoxy or amino with the proviso that R is not $C_1$-$C_4$alkoxy, when A is NH and Z is CH;
$R^1$ is hydrogen, $C_1$-$C_4$alkyl or $C_1$-$C_4$alkoxy;
$R^2$ is $C_3$-$C_5$cycloalkyl, $C_1$-$C_4$alkyl or hydroxy$C_1$-$C_4$alkyl;
$R^3$ is hydrogen, halogen or $C_1$-$C_4$alkyl; and
$R^4$ is hydrogen, methyl or ethyl.

2. A compound according to Formula (Ia)

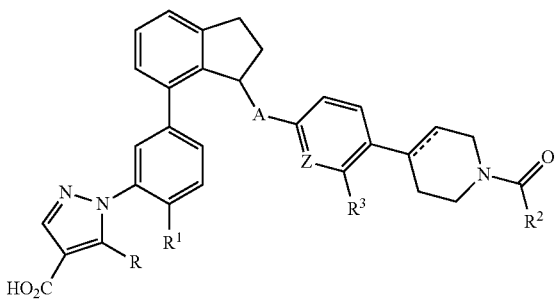

or a pharmaceutically acceptable salt thereof, wherein the ⌇ bond is a single or double bond;
A is $CH_2$, O or N(H);
Z is $CR^4$ or N with the proviso that A is not O when Z is N;
R is $C_1$-$C_4$alkoxy, amino, $C_1$-$C_4$alkylamino or di$C_1$-$C_4$alkylamino;
$R^1$ is hydrogen, $C_1$-$C_4$alkyl or $C_1$-$C_4$alkoxy;
$R^2$ is $C_3$-$C_5$cycloalkyl, $C_1$-$C_4$alkyl or hydroxy$C_1$-$C_4$alkyl;
$R^3$ is hydrogen, halogen or $C_1$-$C_4$alkyl; and
$R^4$ is hydrogen, methyl or ethyl.

3. The compound of claim 2, wherein R is methoxy or amino.

4. The compound claim 2, wherein $R^1$ is hydrogen, methyl or methoxy.

5. The compound according to claim 2, wherein Z is N; and A is $CH_2$ or N(H).

6. The compound according to claim 2, wherein $R^2$ is cyclopropyl or 1-hydroxyethyl.

7. The compound according to claim 2, wherein $R^3$ is ethyl.

8. The compound of claim 2, or a pharmaceutically acceptable salt thereof, wherein the compound is selected from the group consisting of:
 (+)-(R)-1-(3-(3-(4-(1-(cyclopropanecarbonyl)piperidin-4-yl)-3-ethylbenzyl)-2,3-dihydro-1H-inden-4-yl)phenyl)-5-methoxy-1H-pyrazole-4-carboxylic acid;
 (+)-1-(3-((R)-3-(3-ethyl-4-(1-((S)-2-hydroxypropanoyl)piperidin-4-yl)benzyl)-2,3-dihydro-1H-inden-4-yl)phenyl)-5-methoxy-1H-pyrazole-4-carboxylic acid;
 (+)-(S)-1-(3-(3-((4-(1-(cyclopropanecarbonyl)piperidin-4-yl)-3-ethyl phenyl)amino)-2,3-dihydro-1H-inden-4-yl)phenyl)-5-methoxy-1H-pyrazole-4-carboxylic acid;
 (+)-1-(3-(3-((3-ethyl-4-(1-((S)-2-hydroxypropanoyl)piperidin-4-yl)phenyl)amino)-2,3-dihydro-1H-inden-4-yl)phenyl)-5-methoxy-1H-pyrazole-4-carboxylic acid;
 (+)-(S)-1-(3-(3-(4-(1-(cyclopropanecarbonyl)piperidin-4-yl)-3-ethylphenoxy)-2,3-dihydro-1H-inden-4-yl)phenyl)-5-methoxy-1H-pyrazole-4-carboxylic acid;
 1-(3-((S)-3-(3-ethyl-4-(1-((S)-2-hydroxypropanoyl)piperidin-4-yl)phenoxy)-2,3-dihydro-1H-inden-4-yl)phenyl)-5-methoxy-1H-pyrazole-4-carboxylic acid;
 (+)-1-(5-(3-((4-(1-(cyclopropanecarbonyl)piperidin-4-yl)-3-ethylphenyl)amino)-2,3-dihydro-1H-inden-4-yl)-2-methylphenyl)-5-methoxy-1H-pyrazole-4-carboxylic acid;
 (+)-1-(5-(3-((4-(1-(cyclopropanecarbonyl)piperidin-4-yl)-3-ethylphenyl)amino)-2,3-dihydro-1H-inden-4-yl)-2-methoxyphenyl)-5-methoxy-1H-pyrazole-4-carboxylic acid;
 (+)-5-amino-1-(3-(3-((4-(1-(cyclopropanecarbonyl)piperidin-4-yl)-3-ethylphenyl)amino)-2,3-dihydro-1H-inden-4-yl)phenyl)-1H-pyrazole-4-carboxylic acid;

(+)-1-(3-(3-((1'-(cyclopropanecarbonyl)-2-ethyl-1',2',3',6'-tetrahydro-[3,4'-bipyridin]-6-yl)amino)-2,3-dihydro-1H-inden-4-yl)phenyl)-5-methoxy-1H-pyrazole-4-carboxylic acid; and (enantiomer-2)-1-(3-(3-((4-(1-(Cyclopropanecarbonyl)piperidin-4-yl)-3-ethylphenyl)amino)-2,3-dihydro-1H-inden-4-yl)phenyl)-5-(methylamino)-1H-pyrazole-4-carboxylic acid.

9. A compound according to Formula (I)

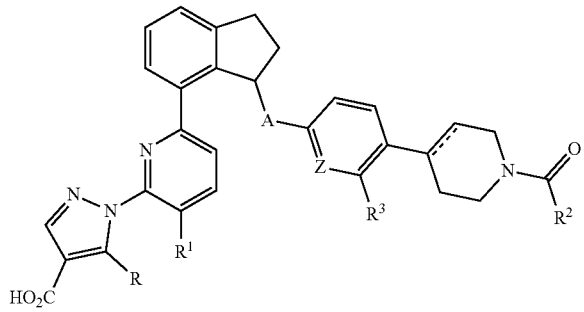

(I)

or a pharmaceutically acceptable salt thereof, wherein
⸌ is a single or double bond;
A is $CH_2$, O or N(H);
Z is $CR^4$ or N, with the proviso that A is not O when Z is N;
R is $C_1$-$C_4$alkoxy or amino with the proviso that R is not $C_1$-$C_4$alkoxy, when A is NH and Z is CH;
$R^1$ is hydrogen, $C_1$-$C_4$alkyl or $C_1$-$C_4$alkoxy;
$R^2$ is $C_3$-$C_5$cycloalkyl, $C_1$-$C_4$alkyl or hydroxy$C_1$-$C_4$alkyl; and
$R^3$ is hydrogen, halogen or $C_1$-$C_4$alkyl; and
$R^4$ is hydrogen, methyl or ethyl.

10. The compound of claim 9, or a pharmaceutically acceptable salt thereof, wherein the compound is selected from the group consisting of:

(+)-1-(6-(3-(4-(1-(cyclopropanecarbonyl)piperidin-4-yl)-3-ethylbenzyl)-2,3-dihydro-1H-inden-4-yl)pyridin-2-yl)-5-methoxy-1H-pyrazole-4-carboxylic acid;

(S)-1-(6-(3-(4-(1-(cyclopropanecarbonyl)piperidin-4-yl)-3-ethylphenoxy)-2,3-dihydro-1H-inden-4-yl)pyridin-2-yl)-5-methoxy-1H-pyrazole-4-carboxylic acid;

1-(6-((S)-3-(3-ethyl-4-(1-((S)-2-hydroxypropanoyl)piperidin-4-yl)phenoxy)-2,3-dihydro-1H-inden-4-yl)pyridin-2-yl)-5-methoxy-1H-pyrazole-4-carboxylic acid;

(+)-5-amino-1-(6-(3-((4-(1-(cyclopropanecarbonyl)piperidin-4-yl)-3-ethylphenyl)amino)-2,3-dihydro-1H-inden-4-yl)pyridin-2-yl)-1H-pyrazole-4-carboxylic acid;

(S)-5-amino-1-(6-(3-(4-(1-(cyclopropanecarbonyl)piperidin-4-yl)-3-ethylphenoxy)-2,3-dihydro-1H-inden-4-yl)pyridin-2-yl)-1H-pyrazole-4-carboxylic acid;

(+)-1-(6-(3-((1'-(cyclopropanecarbonyl)-2-ethyl-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylic acid; and 1-(6-((S or R)-3-((2-ethyl-1'-((S)-2-hydroxypropanoyl)-1',2',3',6'-tetrahydro-[3,4'-bipyridin]-6-yl)amino)-2,3-dihydro-1H-inden-4-yl)pyridin-2-yl)-5-methoxy-1H-pyrazole-4-carboxylic acid.

11. A pharmaceutical composition comprising a compound of claim 1, or a salt thereof, and a pharmaceutically acceptable excipient.

12. A method of treating glaucoma and controlling intraocular pressure comprising: applying a therapeutically effective amount of a pharmaceutical composition comprising a compound of claim 1, or a pharmaceutically acceptable salt thereof to an affected eye of a patient.

13. The method of claim 12, wherein said applying comprises applying using a technique selected from the group consisting of: topical ocular administration, periocular injection, sub-conjunctival injection, sub-tenon injection, intracameral injection, intravitreal injection, intracanalicular injection, implanting delivery device in the cul-de-sac, implanting delivery device adjacent to the sclera, implanting delivery device within the eye, oral administration, intravenous administration, subcutaneous administration, intramuscular administration, parenteral administration, dermal administration, and nasal administration.

14. The method of claim 12 wherein method further comprises administering to the affected eye of the patient a glaucoma treatment agent selected from the group consisting of beta-blockers, prostaglandin analogs, sGC stimulators, nitric oxide precursors, carbonic anhydrase inhibitors, α2 agonists, miotics, and neuroprotectants.

15. The method of claim 12, wherein the method further comprises administering to the affected eye of the patient a PDE-V inhibitor.

16. The method of claim 15 wherein the method PDE-V inhibitor is selected from sildenafil, tadalafil and vardenafil.

17. A pharmaceutical composition comprising a compound of claim 1, or a salt thereof, another therapeutic agent, and a pharmaceutically acceptable excipient.

18. A pharmaceutical composition of claim 17 wherein the other therapeutic agents is selected from the group consisting of beta-blockers, prostaglandin analogs, sGC stimulators, nitric oxide precursors, carbonic anhydrase inhibitors, α2 agonists, miotics, and neuroprotectants.

* * * * *